US008609095B2

(12) United States Patent (10) Patent No.: US 8,609,095 B2
Pedersen et al. (45) Date of Patent: Dec. 17, 2013

(54) ANTI-HER2 ANTIBODIES AND COMPOSITIONS

(75) Inventors: Mikkel Wandahl Pedersen, Alleroed (DK); Allan Jensen, Aberdeen (GB); Per-Johan Meijer, Lyngby (DK)

(73) Assignee: Symphogen A/S, Lyngby (DK)

( * ) Notice: Subject to any disclaimer, the term of this patent is extended or adjusted under 35 U.S.C. 154(b) by 80 days.

(21) Appl. No.: 13/040,029

(22) Filed: Mar. 3, 2011

(65) Prior Publication Data

US 2011/0217305 A1 Sep. 8, 2011

Related U.S. Application Data

(60) Provisional application No. 61/310,552, filed on Mar. 4, 2010, provisional application No. 61/354,133, filed on Jun. 11, 2010, provisional application No. 61/428,014, filed on Dec. 29, 2010.

(51) Int. Cl.
*A61K 39/395* (2006.01)

(52) U.S. Cl.
USPC .................. 424/138.1; 424/155.1; 424/174.1

(58) Field of Classification Search
None
See application file for complete search history.

(56) References Cited

U.S. PATENT DOCUMENTS

| | | | |
|---|---|---|---|
| 6,949,245 B1 | 9/2005 | Sliwkowski | |
| 7,041,292 B1 | 5/2006 | Sliwkowski | |
| 7,485,302 B2 | 2/2009 | Adams et al. | |
| 7,498,142 B2 | 3/2009 | Yarden et al. | |
| 7,501,122 B2 | 3/2009 | Adams et al. | |
| 7,537,931 B2 | 5/2009 | Adams et al. | |
| 7,618,631 B2 | 11/2009 | Sliwkowski | |
| 2006/0188509 A1 | 8/2006 | Derynck et al. | |
| 2007/0020261 A1 | 1/2007 | Sliwkowski et al. | |
| 2007/0178102 A1 | 8/2007 | Yarden et al. | |
| 2008/0102069 A1 | 5/2008 | Friess et al. | |
| 2009/0202546 A1 | 8/2009 | Harris et al. | |
| 2009/0214541 A1 | 8/2009 | Gillies et al. | |
| 2009/0317387 A1 | 12/2009 | Paton et al. | |

FOREIGN PATENT DOCUMENTS

| | | |
|---|---|---|
| WO | WO 99/55367 A1 | 11/1999 |
| WO | WO 99/56129 A1 | 11/1999 |
| WO | WO 01/00245 A2 | 1/2001 |
| WO | WO 2004/048525 | 6/2004 |
| WO | WO 2006/087637 A2 | 8/2006 |
| WO | WO 2008/104183 A2 | 9/2008 |
| WO | WO 2009/151356 A1 | 12/2009 |
| WO | WO 2010/022736 A2 | 3/2010 |
| WO | WO 2010/029534 A1 | 3/2010 |

OTHER PUBLICATIONS

Arteaga, C.L., "Epidermal Growth Factor Receptor Dependence in Human Tumors: More Than Just Expression?," *Oncologist* 7 (*Suppl. 4*):31-39, AlphaMed Press, United States (2002).
Badache, A. and Hynes, N.E., "A new therapeutic antibody masks ErbB2 to its partners," *Cancer Cell* 5:299-301, Elsevier Inc., United States (2004).
Baselga, J., "Why the Epidermal Growth Factor Receptor? The Rationale for Cancer Therapy," *Oncologist* 7(*Suppl. 4*):2-8, AlphaMed Press, United States (2002).
Baselga, J. and Albanell, J., "Mechanism of action of anti-HER2 monoclonal antibodies," *Ann. Oncol.12* (*Suppl. 1*):S35-S41, Kluwer Academic Publishers, Netherlands (2001).
Ben-Kasus, T., et al., "Persistent elimination of ErbB-2/HER2-overexpressing tumors using combinations of monoclonal antibodies: Relevance of receptor endocytosis," *Proc. Natl. Acad. Sci.* 106:3294-3299, National Academy of Sciences, United States (Mar. 2009).
Bodey, B., et al., "Clinical and Prognostic Significance of the Expression of the *c-erbB-2* and *c-erbB-3* Oncoproteins in Primary and Metastatic Malignant Melanomas and Breast Carcinomas," *Anticancer Res.* 17:1319-1330, J.G. Delinassios, Greece (1997).
Citri, A. and Yarden, Y., "EGF-ERBB signalling: towards the systems level," *Nat. Rev. Mol. Cell Biol.* 7:505-516, Nature Publishing Group, United Kingdom (2006).
De Potter, C. R., "The *neu*-Oncogene: More Than a Prognostic Indicator?" *Hum. Pathol.* 25:1264-1268, W.B. Saunders Company, United States (1994).
Drebin, J.A., et al., "Monoclonal antibodies reactive with distinct domains of the neu oncogene-encoded p185 molecule exert synergistic anti-tumor effects in vivo," [Abstract] *Oncogene* 2:273-277, Nature Publishing Group, United Kingdom (1988).
Ferguson, K.M., "Structure-Based View of Epidermal Growth Factor Receptor Regulation," *Annu. Rev. Biophys.* 37:353-373, Annual Reviews, United States (2008).
Franklin, M.C., et al., "Insights into ErbB signaling from the structure of the ErbB2-pertuzumab complex," *Cancer Cell* 5:317-328, Elsevier Inc., United States (2004).
Freudenberg, J.A., et al., "The role of HER2 in early breast cancer metastasis and the origins of resistance to HER2-targeted therapies," *Exp. Mol. Pathol.* 87:1-11, Elsevier Inc., Netherlands (May 2009).
Friedländer, E., et al., "ErbB-directed immunotherapy: Antibodies in current practice and promising new agents," *Immunol. Lett.* 116:126-140, Elsevier B.V., Netherlands (2007).
Friedman, L.M., et al., "Synergistic down-regulation of receptor tyrosine kinases by combinations of mAbs: Implications for cancer immunotherapy," *Proc. Natl. Acad. Sci. USA* 102:1915-1920, National Academy of Sciences, United States (2005).
Graus-Porta, D., et al., "ErbB-2, the preferred heterodimerization partner of all ErbB receptors, is a mediator of lateral signaling," *EMBO J.* 16:1647-1655, Oxford University Press, United Kingdom (1997).
Guy, P.M., et al., "Insect cell-expressed p180$^{erbB3}$ possesses an impaired tyrosine kinase activity," *Proc. Natl. Acad. Sci. USA* 91:8132-8136, National Academy of Sciences, United States (1994).
Hommelgaard, A.M., et al., "Association with Membrane Protrusions Makes ErbB2 an Internalization-resistant Receptor," *Mol. Biol. Cell* 15:1557-1567, The American Society for Cell Biology, United States (2004).

(Continued)

*Primary Examiner* — Laura B Goddard
(74) *Attorney, Agent, or Firm* — Ropes & Gray LLP

(57) ABSTRACT

The present invention relates to novel therapeutic antibodies directed against HER2 (ErbB2), as well as recombinant polyclonal anti-HER2 antibody compositions comprising at least two of said recombinant anti-HER2 antibodies, and use of the antibodies and antibody compositions for treatment of cancer.

13 Claims, 26 Drawing Sheets

(56) References Cited

OTHER PUBLICATIONS

Kasprzyk, P.G., et al., "Therapy of an Animal Model of Human Gastric Cancer Using a Combination of Anti-erbB-2 Monoclonal Antibodies," *Cancer Res.* 52:2771-2776, American Association for Cancer Research, United States (1992).

King, C.R., et al., "EGF binding to its receptor triggers a rapid tyrosine phosphorylation of the erbB-2 protein in the mammary tumor cell lines SK-BR-3," *EMBO J.* 7:1647-1651, IRL Press Limited, United Kingdom (1988).

Klapper, L.N, et al., "A subclass of tumor-inhibitory monoclonal antibodies to ErbB-2/HER2 blocks crosstalk with growth factor receptors," *Oncogene* 14:2099-2109, Stockton Press, United States (1997).

Klapper, L.N., et al., "The ErbB-2/HER2 oncoprotein of human carcinomas may function solely as a shared coreceptor for multiple stroma-derived growth factors," *Proc. Natl. Acad. Sci. USA* 96:4995-5000, National Academy of Sciences, United States (1999).

Muthuswamy, S.K., et al., "ErbB2, but not ErbB1, reinitiates proliferation and induces luminal repopulation in epithelial acini," *Nat. Cell Biol.* 3:785-792, Macmillan Magazines Ltd., United States (2001).

Pao, W., et al., "Acquired Resistance of Lung Adenocarcinomas to Gefitnib or Erlotinib Is Associated with a Second Mutation in the EGFR Kinase Doman," *PLoS Med.* 2:0225-0235, PLoS Biology, United States (2005).

Pedersen, M.W., et al., "Sym004: A Novel Synergistic Anti-Epidermal Growth Factor Receptor Antibody Mixture with Superior Anticancer Efficacy," *Cancer Res.* 70:588-597, American Association for Cancer Research, United States (Jan. 2010).

Pedersen, N.M., et al., "Expression of Epidermal Growth Factor Receptor or ErbB3 Facilitates Geldanamycin-Induced Down-Regulation of ErbB2," *Mol. Cancer Res.* 7:275-284, American Association for Cancer Research, United States (Feb. 2009).

Pinkas-Kramarski, R., et al., "Diversification of Neu differentiation factor and epidermal growth factor signaling by combinatorial receptor interactions," *EMBO J.* 15:2452-2467, Oxford University Press, United Kingdom (1996).

Rajkumar, T., et al., "Expression of the Type 1 Tyrosine Kinase Growth Factor Receptors EGF Receptor, c-erbB2 and c-erbB3 in Bladder Cancer," *J. Pathol.* 179:381-385, John Wiley & Sons, Ltd., United Kingdom (1996).

Ravdin, P.M. and Chamness, G.C., "The c-*erbB*-2 proto-oncogene as a prognostic and predictive marker in breast cancer: a paradigm for the development of other macromolecular markers—a review," *Gene* 159:19-27, Elsevier Science B.V., Netherlands (1995).

Rohrer, T., "Antibody drug conjugates: Potent weapons for the oncology arsenal," *Chemistry Today* 27:56-60, Teknoscienze Srl, Italy (Sep.-Oct. 2009).

Schrama, D., et al., "Antibody targeted drugs as cancer therapeutics," *Nat. Rev. Drug Discov.* 5:147-159, Nature Publishing Group, United Kingdom (2006).

Slamon, D.J., et al., "Human Breast Cancer: Correlation of Relapse and Survival with Amplification of HER-2/*neu* Oncogene," *Science* 235:177-182, American Association for the Advancement of Science, United States (1987).

Slamon, D.J., et al., "Use of Chemotherapy Plus a Monoclonal Antibody Against HER2 for Metastatic Breast Cancer That Overexpresses HER2," *N. Engl. J. Med.* 344:783-792, Massachusetts Medical Society, United States (2001).

Spector, N., et al., "HER2 therapy: Small molecule HER-2 tyrosine kinase inhibitors," *Breast Cancer Res.* 9:205-212, BioMed Central Ltd., United States (2007).

Spiridon, C.I., et al., "A Comparison of the *in Vitro* and *in Vivo* Activities of IgG and F(ab')$_2$ Fragments of a Mixture of Three Monoclonal Anti-Her-2 Antibodies," *Clin. Cancer Res.* 10:3542-3551, American Association for Cancer Research, United States (2004).

Troyer, K.L. and Lee, D.C., "Regulation of Mouse Mammary Gland Development and Tumorigenesis by the ERBB Signaling Network," *J. Mammary Gland Biol. Neoplasia* 6:7-21, Plenum Publishing Corporation, United States (2001).

Tvorogov, D., et al., "Effective Suppression of Vascular Network Formation by Combination of Antibodies Blocking VEGFR Ligand Binding and Receptor Dimerization," *Cancer Cell* 18:1-11, Elsevier Inc., United States (Dec. 2010).

Tvorogov, D., et al., "Supplemental Information: Effective Suppression of Vascular Network Formation by Combination of Antibodies Blocking VEGFR Ligand Binding and Receptor Dimerization," *Cancer Cell* 18:630-640, Elsevier Inc., United States (Dec. 2010).

Tzahar, E., et al., "A Hierarchical Network of Interreceptor Interactions Determines Signal Transduction by Neu Differentiation Factor/Neuregulin and Epidermal Growth Factor," *Mol. Cell Biol.* 16:5276-5287, American Society for Microbiology, United States (1996).

Wu, A.M. and Senter, P.D., "Arming Antibodies: prospects and challenges for immunoconjugates," *Nat. Biotechnol.* 23:1137-1146, Nature American Publishing, United States (2005).

Yamamoto, T., et al., "Similarity of protein encoded by the human *c-erb-B-2* gene to epidermal growth factor receptor," *Nature* 319:230-234, Nature Publishing Group, United Kingdom (1986).

Yarden, Y. and Sliwkowski, M.X., "Untangling the ErbB Signalling Network," *Nat. Rev. Mol. Cell Biol.* 2:127-137, Macmillan Magazines Ltd., United States (2001).

Zhu, W., et al., "Controlled Internalization of Her-2/*neu* Receptors by Cross-linking for Targeted Delivery," *Cancer Biol. Ther.* 6:1960-1966, Landes Bioscience, United States (2007).

Coyne et al., "Dual potency anti-HER2/neu and anti-EGFR anthracycline immunoconjugates in chemotherapeutic-resistant mammary carcinoma combined with cyclosporin A and verapamil P-glycoprotein inhibition," *Journal of Drug Targeting* 17(6):474-489 (2009).

Huhalov et al., "MM-111, an ErbB2/ErbB3 bispecific antibody with potent activity in ErbB2-overexpressing cells, positively combines with trastuzumab to inhibit growth of breast cancer cells driven by the ErbB2/ErbB3 oncogenic unit," *American Association for Cancer Research, Proceedings of the Annual Meeting* 51:845-846 (2010).

Nahta et al., "The HER-2-Targeting Antibodies Trastuzumab and Pertuzumab Synergistically Inhibit the Survival of Breast Cancer Cells," *Cancer Research* 64:2343-2346 (2004).

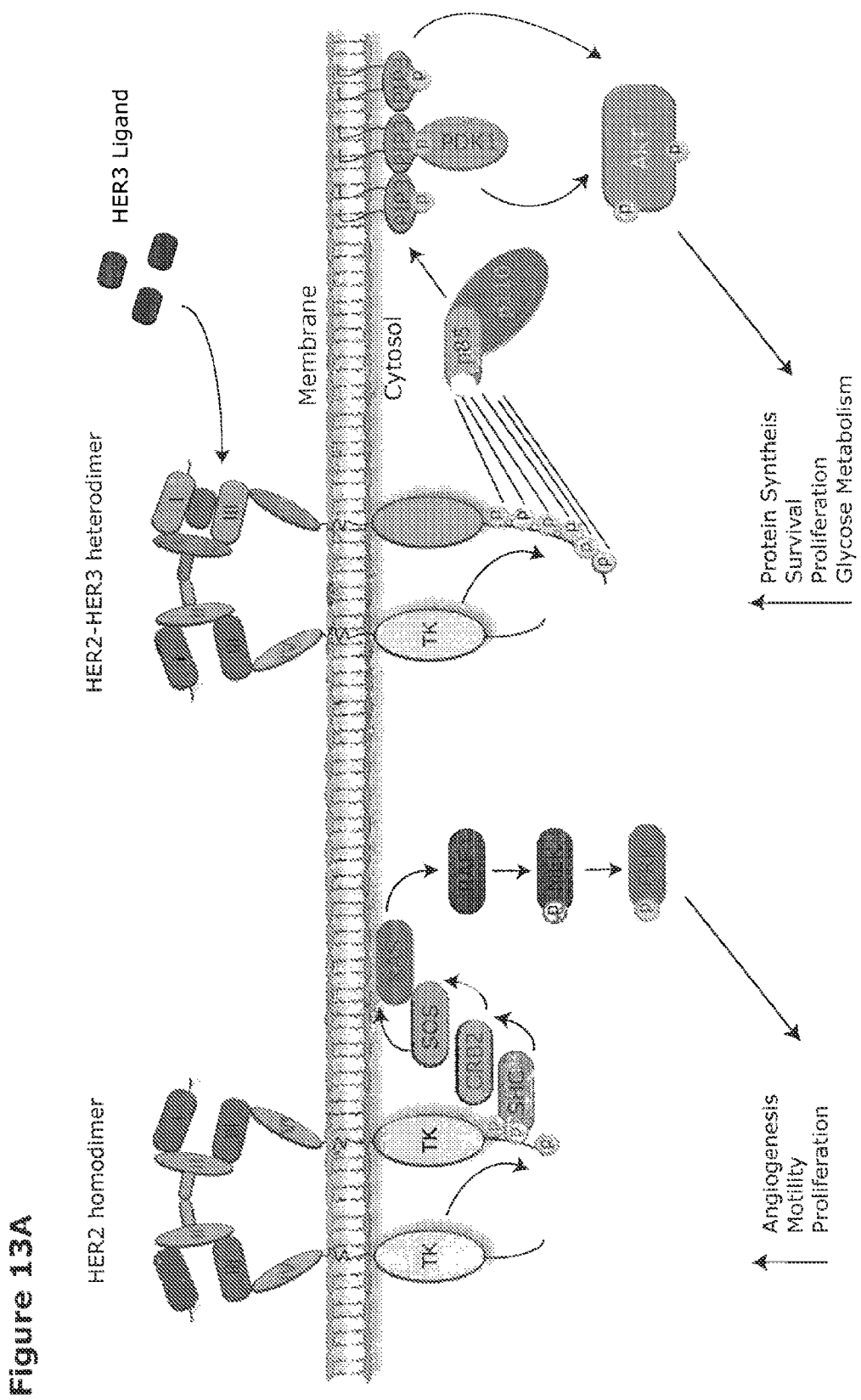

ANTI-HER2 ANTIBODIES AND COMPOSITIONS

CROSS-REFERENCE TO RELATED APPLICATIONS

This application claims the benefit of the filing date of U.S. Provisional Appl. No. 61/310,552, filed Mar. 4, 2010, U.S. Provisional Appl. No. 61/354,133, filed Jun. 11, 2010, and U.S. Provisional Appl. No. 61/428,014, filed Dec. 29, 2010, all of which are incorporated by reference in their entireties.

REFERENCE TO SEQUENCE LISTING SUBMITTED ELECTRONICALLY VIA EFS-WEB

The content of the electronically submitted sequence listing in ASCII text file (Name: 24880260003_SequenceListing.txt; Size: 73,527 bytes; and Date of Creation: Mar. 3, 2011) filed with the application is incorporated herein by reference in its entirety.

BACKGROUND OF THE INVENTION

1. Field of the Invention

The present invention relates to novel recombinant antibodies targeting the HER2 receptor and compositions comprising two or more of these antibodies for use in human cancer therapy.

2. Background of the Invention

The epidermal growth factor receptor (EGFR) family (also known as the ErbB family) is a subgroup of the receptor tyrosine kinases (RTKs) and consists of four members: EGFR/ErbB, HER2/ErbB2, HER3/ErbB3 and HER4/ErbB4. The members of the EGFR family are closely related single-chain modular glycoproteins with an extracellular ligand binding region, a single transmembrane domain and an intracellular tyrosine kinase (reviewed in Ferguson (2008) *Annu Rev Biophys.* 37: 353-373). In normal physiological settings the ErbB family regulates key events in coordination of cell growth, differentiation and migration (Citri et al. (2006) *Nat Rev Mol Cell Biol.* 7: 505-516). EGFR, HER2 and HER3 are believed to play crucial roles in the malignant transformation of normal cells and in the continued growth of cancer cells. EGFR and HER2 have been found to be overexpressed by many epithelial cancers (Slamon et al. (1987) *Science,* 235: 177-182; Arteaga (2002) *Oncologist* 7 Suppl 4: 31-39; Bodey et al. (1997) *Anticancer Res.* 17: 1319-1330; Rajkumar et al. (1996) *J Pathol.* 179: 381-385). Overexpression of EGFR and HER2 has furthermore been linked to disease progression, reduced survival, poor response and chemotherapy resistance in several human epithelial cancers (Slamon et al. (1987) supra; Baselga et al. (2002) *Oncologist* 7 Suppl 4: 2-8).

Human epidermal growth factor receptor 2 (HER2, also known as ErbB2 or Neu; UniProtKB/Swiss-Prot No. P04626) consists of 1233 amino acids and is structurally similar to EGFR with an extracellular domain consisting of four subdomains I-IV, a transmembrane domain, a juxtamembrane domain, an intracellular cytoplasmic tyrosine kinase and a regulatory C-terminal domain (Yamamoto et al. (1986) *Nature* 319: 230-234).

HER2 is the only member of the ErbB family that does not bind known ligands (Klapper et al. (1999) *Proc Natl Acad Sci USA* 96: 4995-5000). HER2 is instead activated via formation of heteromeric complexes with other ErbB family members and thereby indirectly regulated by EGFR and HER3 ligands (reviewed in Yarden et al. (2001) *Nat Rev Mol Cell Biol.* 2: 127-137). HER2 is the preferred heterodimerization partner of the three other ErbB receptors (Graus-Porta et al. (1997) *EMBO J* 16: 1647-1655; Tzahar et al. (1996) *Mol Cell Biol.* 16: 5276-5287), enhancing the affinity of the other ErbB receptors for their ligands by slowing down the rate of ligand-receptor complex dissociation, whereby HER2 enhances and prolongs signaling (Pedersen et al. (2009) *Mol Cancer Res.* 7: 275-284). Heterodimerization of HER2 and another ligand-bound receptor of the ErbB family induces cross-phosphorylation, leading to phosphorylation of the C-terminal amino acids. These in turns serve as scaffolds for signaling molecules (King et al. (1988) *EMBO J* 7:1647-1651). The most active HER2 heterodimer is the HER2-HER3 complex (Pinkas-Kramarski et al. (1996) *EMBO J* 15: 2452-2467), where HER2 complements the kinase-deficient HER3 by providing an active kinase (Guy et al. (1994) *Proc Natl Acad Sci USA* 91: 8132-8136.). In contrast to EGFR, HER2 is internalization resistant (Hommelgaard et al. (2004) *Mol Biol Cell* 15: 1557-1567), escaping lysosomal degradation and thereby remaining at the plasma membrane.

The primary role of HER2 in normal tissues appears to be modulation of signaling initiated through a ligand-bound ErbB receptor. Like EGFR, HER2 is primarily expressed by epithelial cells (reviewed in Freudenberg et al. (2009) *Exp Mol. Pathol.* 87: 1-11) and has been found to have a non-oncogenic role in regulating growth, differentiation, apoptosis and remodeling in normal mammary gland development (Troyer et al. (2001) *J Mammary Gland Biol Neoplasia* 6: 7-21). As it is the case for EGFR, an excess of HER2 on the cell surface causes transformation of epithelial cells from multiple tissues (Freudenberg et al. (2009) supra). HER2 amplification and overexpression have been reported in a range of human tumors, including 20-30% of invasive ductal carcinomas, and is a well recognized predictor of poor clinical outcome with reduced overall survival rates (Slamon et al. (1987) supra; Ravdin et al. (1995) *Gene* 159: 19-27). High levels of HER2 can be readily detected in human breast tissues that show early signs of transformation but have not yet fully transformed, indicating the important role of HER2 in the early malignant transformation (Freudenberg et al. (2009) supra). High levels of HER2 have also been implicated in other epithelial cancers such as colorectal, ovarian, pancreatic, lung, and urothelial cancers (Freudenberg et al. (2009) supra). HER2 activation induces uncontrolled proliferation, protects against apoptosis, and disrupts normal epithelial organization (Muthuswamy et al. (2001) *Nat Cell Biol.* 3: 785-792). Furthermore, HER2 is expressed by metastatic cells and may play a role in cancer cell motility (De Potter (1994) *Hum Pathol.* 25: 1264-1268).

EGFR and HER2 are validated cancer targets and both monoclonal antibodies and small molecule inhibitors targeting these receptors have been approved for the treatment of various cancers. However, patients who initially respond to these therapies often relapse due to evolvement of acquired resistance (Pao et al. (2005) *PLoS Med* 2: e73). The monoclonal antibody trastuzumab (marketed as Herceptin®) targets HER2 and is used for treatment of breast cancer in which the HER2 receptor is overexpressed. In January 2010 Herceptin was approved in the European Union in combination with chemotherapy for use in patients with HER2-positive metastatic stomach (gastric) cancer. Another monoclonal antibody directed in part against the HER2 receptor, pertuzumab, is currently in various clinical trials. In contrast to trastuzumab, which acts by binding to HER2 and thereby blocking its function, pertuzumab is a HER dimerization inhibitor which inhibits dimerization of HER2 to HER3 and the other EGFR receptors.

Since pertuzumab is still in clinical trials, the extent to which it may ultimately prove to be clinically beneficial is still unknown. For trastuzumab, while it has shown clinical benefits in terms of e.g. prolonged survival in connection with chemotherapy compared to chemotherapy alone, a majority of HER2 positive breast cancer patients were nevertheless found to be non-responders (45% overall response rate for Herceptin+chemotherapy vs. 29% for chemotherapy alone; Prescribing Information for Herceptin, Genentech, March 2009). Similar results are described by Slamon et al. in *N Engl J Med* (2001), 344(11):783-92, who also describe that the combination of Herceptin and chemotherapy resulted in a lower rate of death at 1 year compared to chemotherapy alone (22% vs. 33%, P=0.008) and a longer median survival (25.1 vs. 20.3 months, P=0.046). Thus, while monoclonal antibody therapy directed against HER2 has been shown to provide improved treatment in e.g. metastatic breast cancers that overexpress HER2, there is still considerable room for improvement.

BRIEF SUMMARY OF THE INVENTION

The present invention is directed to novel recombinant antibodies targeting the HER2 receptor as well as compositions comprising two or more of these antibodies and use of the antibodies and compositions for human cancer therapy, e.g. for the treatment of breast cancer, ovarian cancer, gastric cancer and other cancers that overexpress HER2. Compared to the currently available treatments for such cancers, including available monoclonal antibodies directed against HER2 or other receptors of the EGFR family, it is contemplated that the antibodies of the invention may provide a superior clinical response either alone or, preferably, in a composition comprising two or more such antibodies, and optionally in combination with other treatments such as chemotherapy.

In one aspect, the invention relates to novel recombinant anti-HER2 antibodies based on the antibodies referred to herein as antibodies 4380/4381, 4382, 4383, 4384, 4385, 4386, 4387, 4517, 4518 and 4519, as well as humanized variants thereof. In one embodiment, this aspect of the invention relates to a recombinant anti-HER2 antibody molecule comprising the heavy chain CDR3 sequence of any one of the antibodies referred to herein as antibodies 4380/4381, 4382, 4383, 4384, 4385, 4386, 4387, 4517, 4518 and 4519.

Further embodiments of this aspect of the invention include: a recombinant anti-HER2 antibody molecule comprising the heavy chain CDR3 sequence and the light chain CDR3 sequence of any one of antibodies 4380/4381, 4382, 4383, 4384, 4385, 4386, 4387, 4517, 4518 and 4519; a recombinant anti-HER2 antibody molecule comprising the heavy chain CDR1, CDR2 and CDR3 sequences and light chain CDR1, CDR2 and CDR3 sequences of any one of these antibodies; and a recombinant anti-HER2 antibody comprising the heavy chain variable region sequence and the light chain variable region sequence of any one of these antibodies, or comprising a heavy chain variable region sequence and a light chain variable region sequence each having at least 80%, 85%, 90% or 95% sequence identity, such as at least 96%, 97%, 98% or 99% sequence identity, with the heavy chain and light chain variable region sequences, respectively, of any one of these antibodies.

Another aspect of the invention relates to a recombinant antibody composition, comprising at least first and second recombinant anti-HER2 antibodies, wherein the first and second antibodies bind distinct epitopes of HER2, and wherein one or both of the first and second antibodies are selected from the group of antibodies outlined above.

A further aspect of the invention relates to a recombinant polyclonal anti-HER2 antibody composition comprising at least first, second and third recombinant anti-HER2 antibodies that bind distinct epitopes of HER2, wherein binding of the first and second antibodies to HER2 results in HER2 receptor internalization, and wherein binding of the third antibody to HER2 results in inhibition of ligand-induced phosphorylation of HER3.

A further aspect of the invention relates to an immunoconjugate comprising a recombinant anti-HER2 antibody of the invention conjugated to an anti-cancer agent. A related aspect relates to compositions comprising at least first and second recombinant anti-HER2 antibodies of the invention, wherein at least one anti-HER2 antibody in said composition is an immunoconjugate.

A further aspect of the invention relates to a nucleic acid molecule having a nucleotide sequence that encodes an anti-HER2 antibody of the invention, as well as expression vectors comprising such a polynucleotide and host cells that have been transfected with such an expression vector.

A still further aspect of the invention relates to methods for producing antibodies and polyclonal antibody compositions of the invention.

A still further aspect of the invention relates to methods for treating a disease in a human or animal subject, in particular treatment of cancer in humans, by administering an anti-HER2 antibody or composition of the invention to said subject. A related aspect is the use of one or more anti-HER2 antibodies of the invention for preparation of a medicament for use in treating a disease in a human or animal, in particular for the treatment of cancer in humans.

A still further aspect of the invention relates to a method for inducing internalization of HER2 on the surface of cells that overexpress HER2, the method comprising contacting the cells with a recombinant anti-HER2 antibody or immunoconjugate or a recombinant anti-HER2 antibody composition of the invention.

Additional aspects of the invention and particular embodiments will be apparent from the description and examples below.

BRIEF DESCRIPTION OF DRAWINGS

FIG. 13A shows the distinct but interrelated roles of HER2 homodimers and HER2/HER3 heterodimers in oncogenic signaling in human cancers.

DETAILED DESCRIPTION OF THE INVENTION

Definitions

Figure 1:
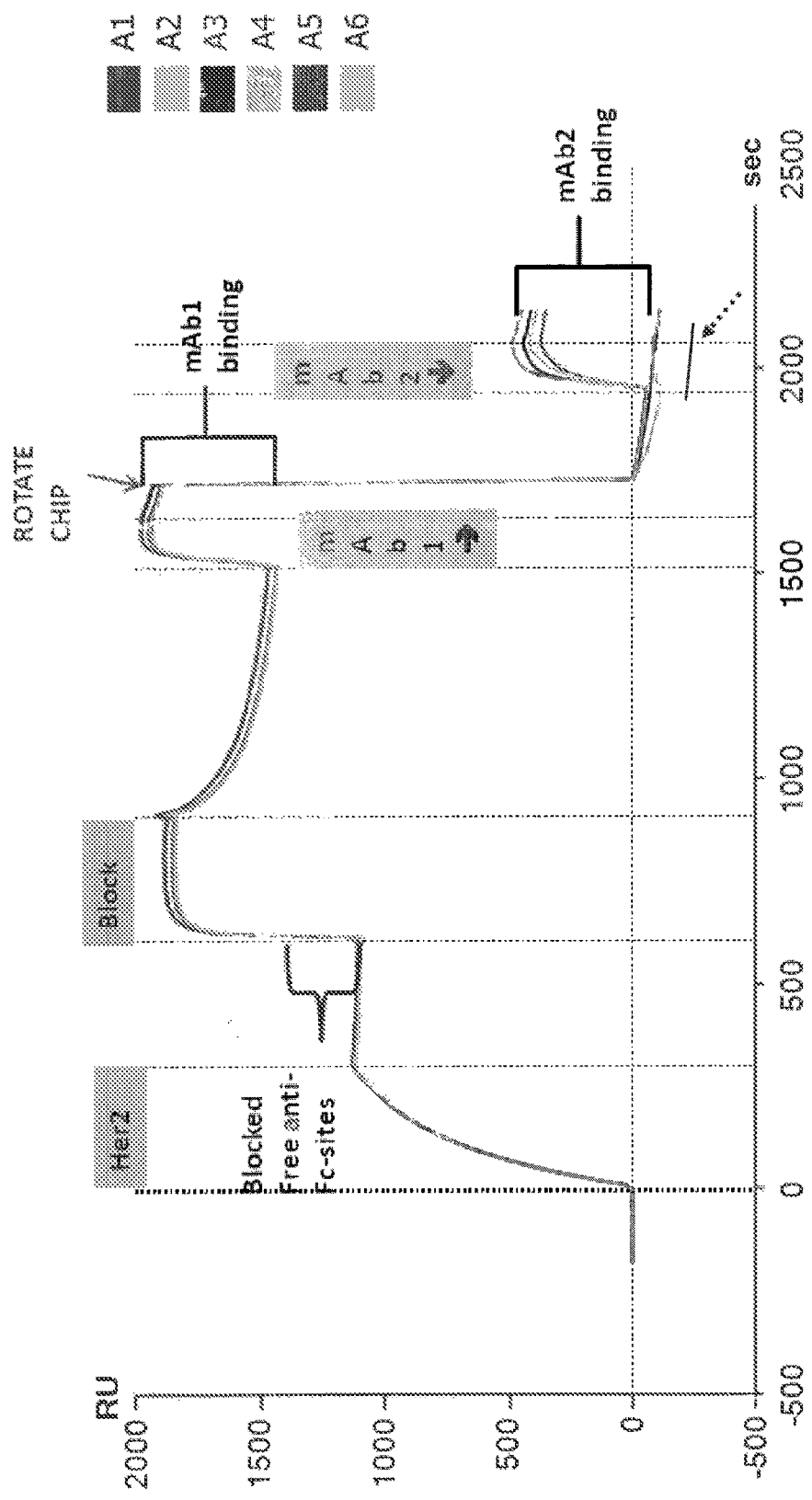
FIG. 1 illustrates the results from a representative epitope binning of anti-HER2 antibodies of the invention.
Figure 2A:
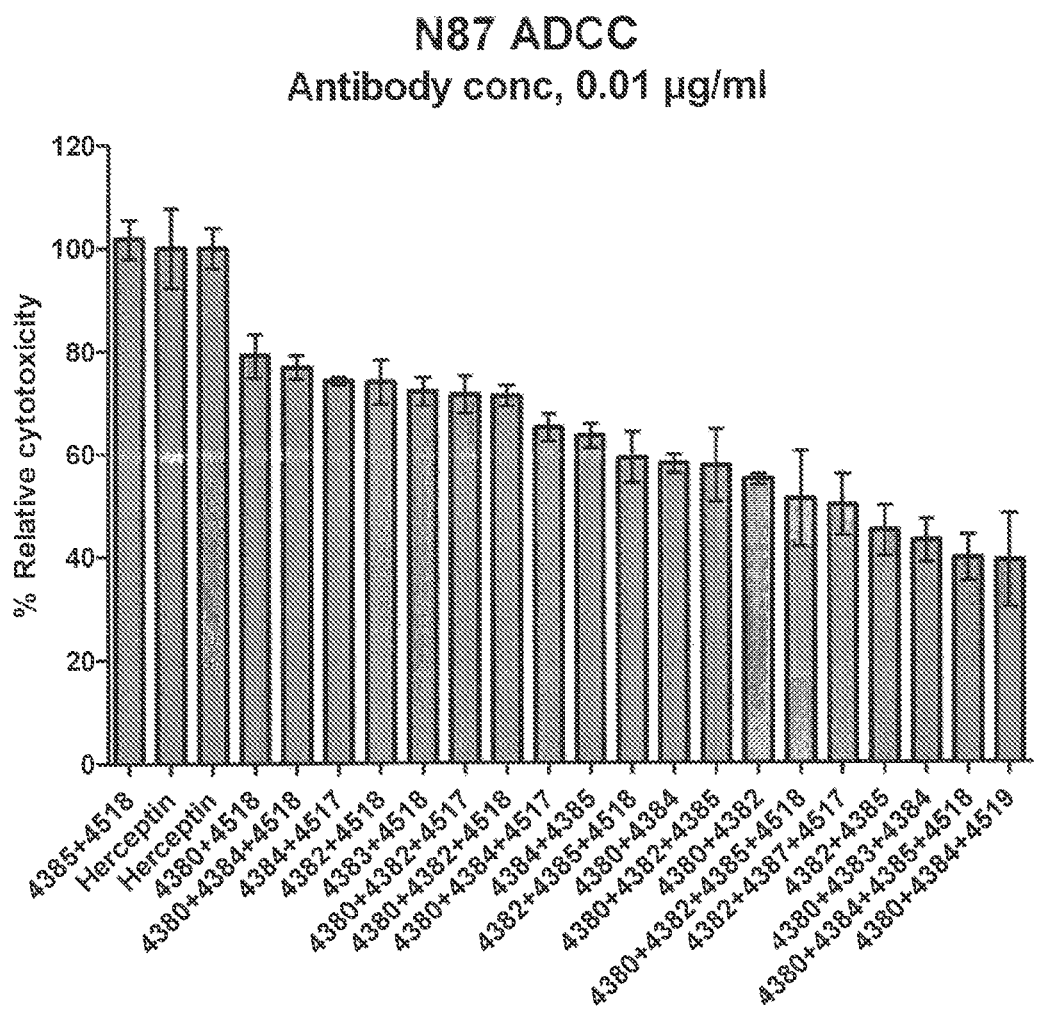
FIGS. 2A, 2B, 2C and 2D show the percent relative ADCC at two different antibody concentrations in N87 and SKBR3 cancer cell lines induced by antibody mixtures containing two, three or four anti-HER2 antibodies of the invention.
Figure 2B:
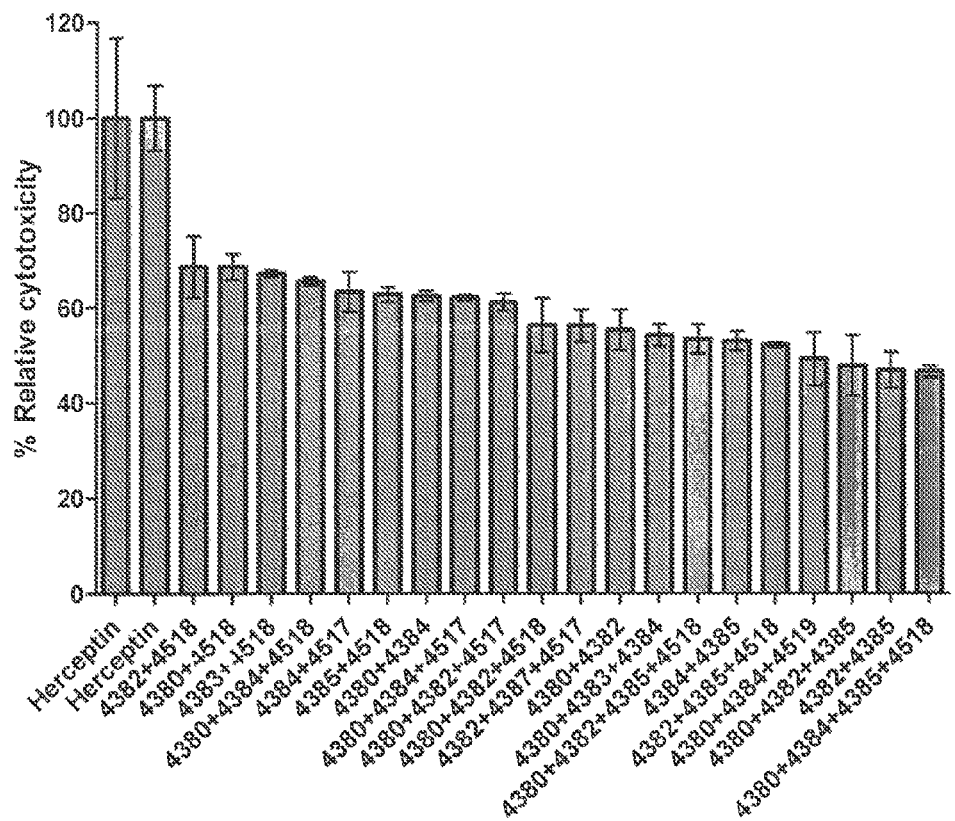
Figure 2C:
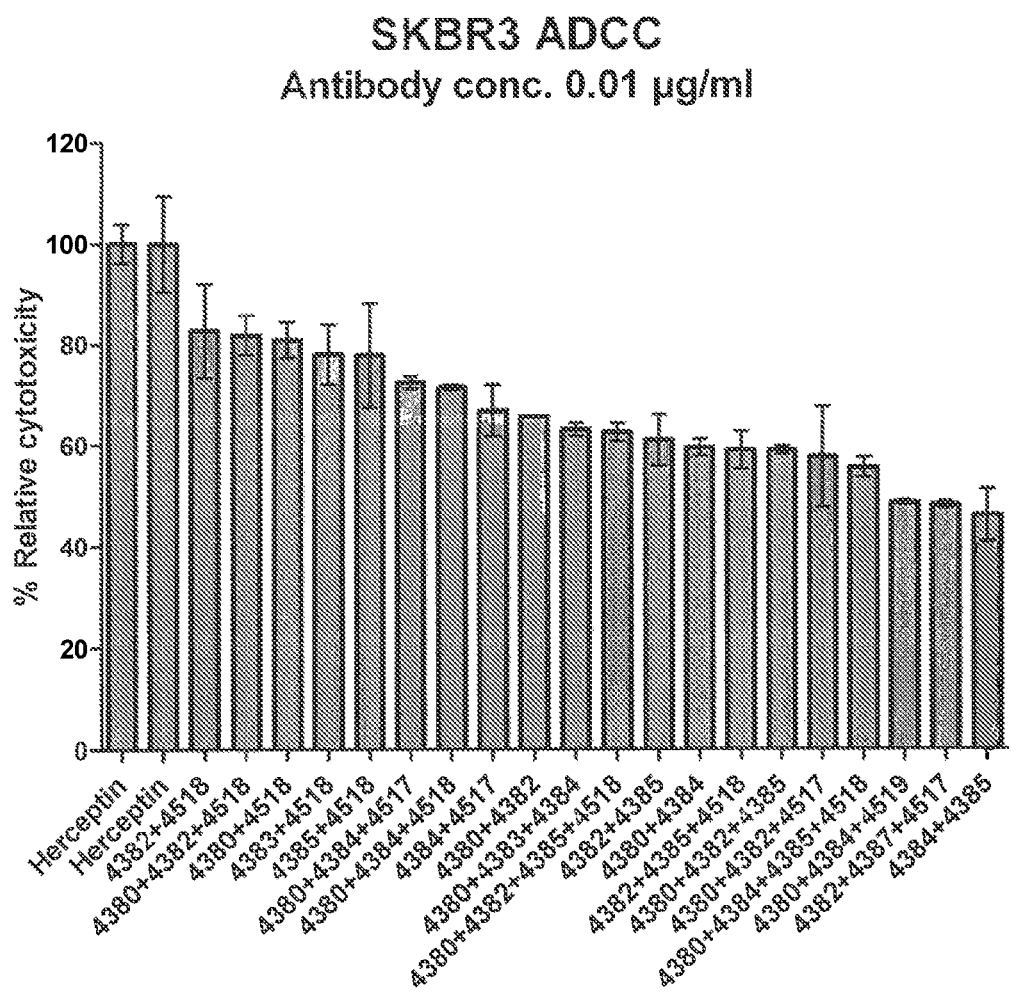
Figure 2D:
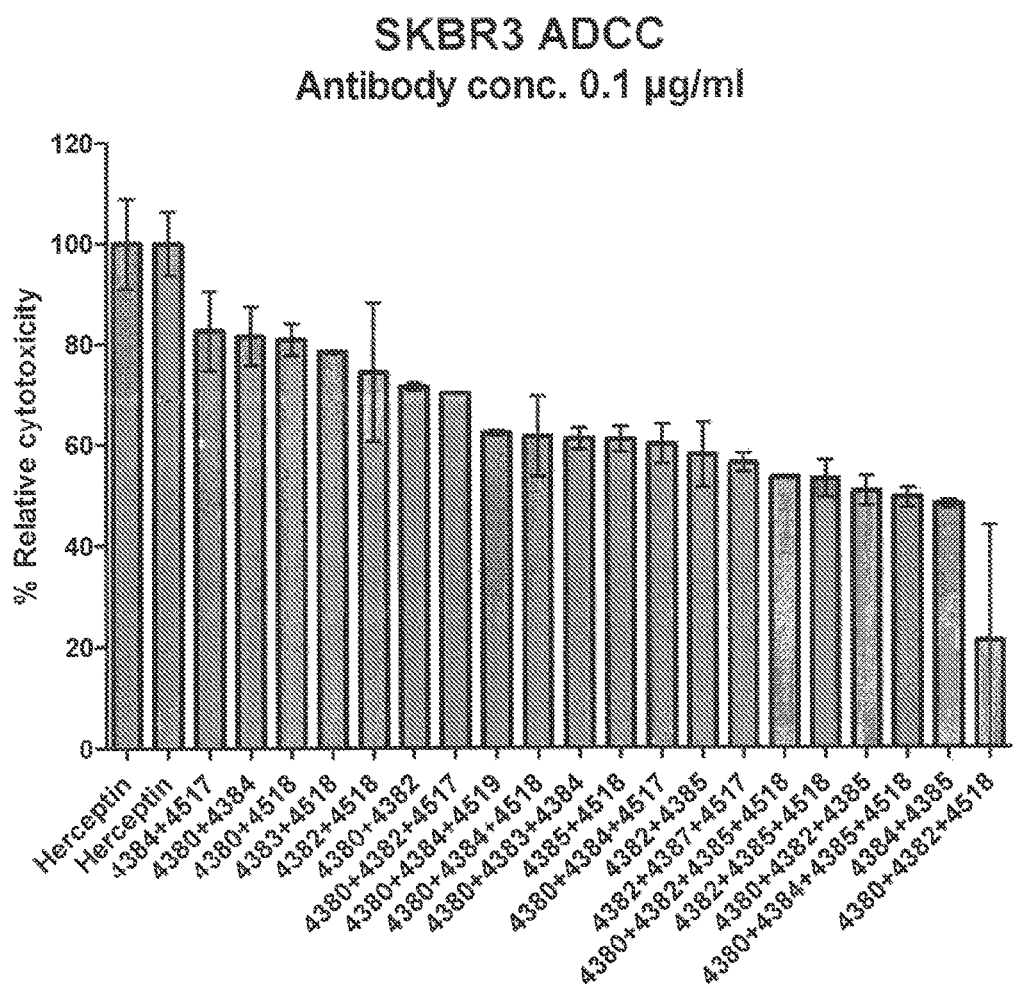
Figure 3A:
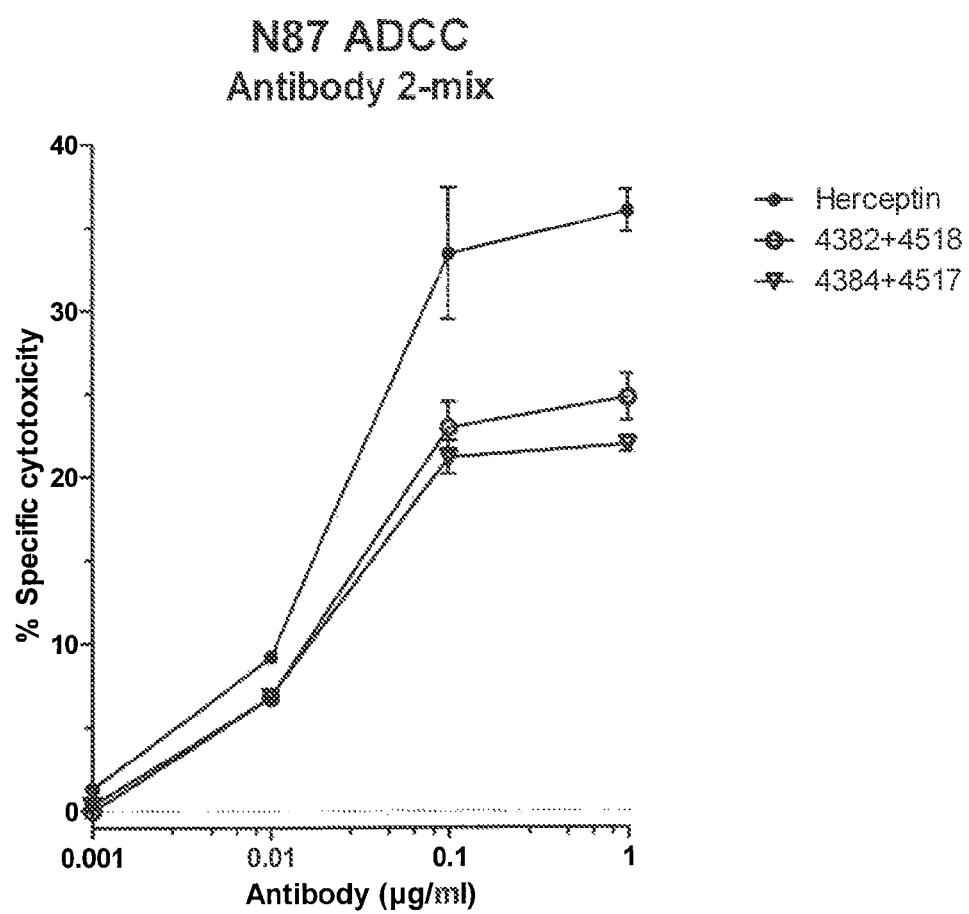
FIGS. 3A, 3B, 3C and 3D show measurements of ADCC in N87 and SKBR3 cells using mixtures of two or three anti-HER2 antibodies of the invention.
Figure 3B:
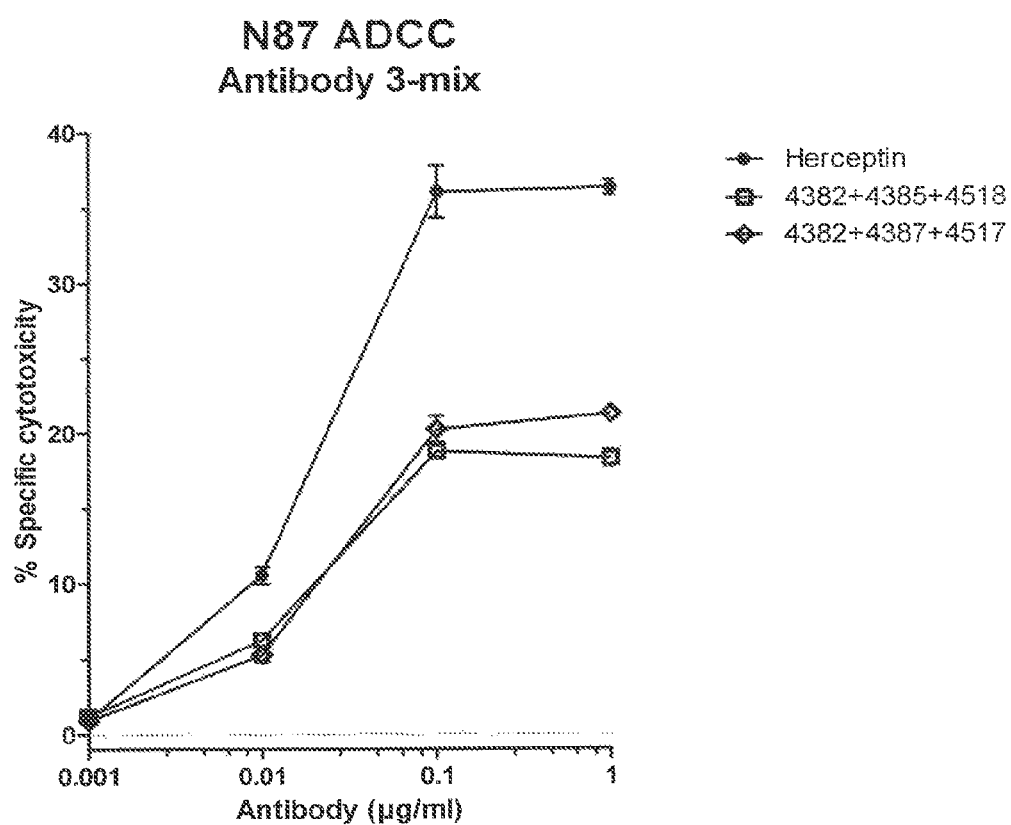
Figure 3C:
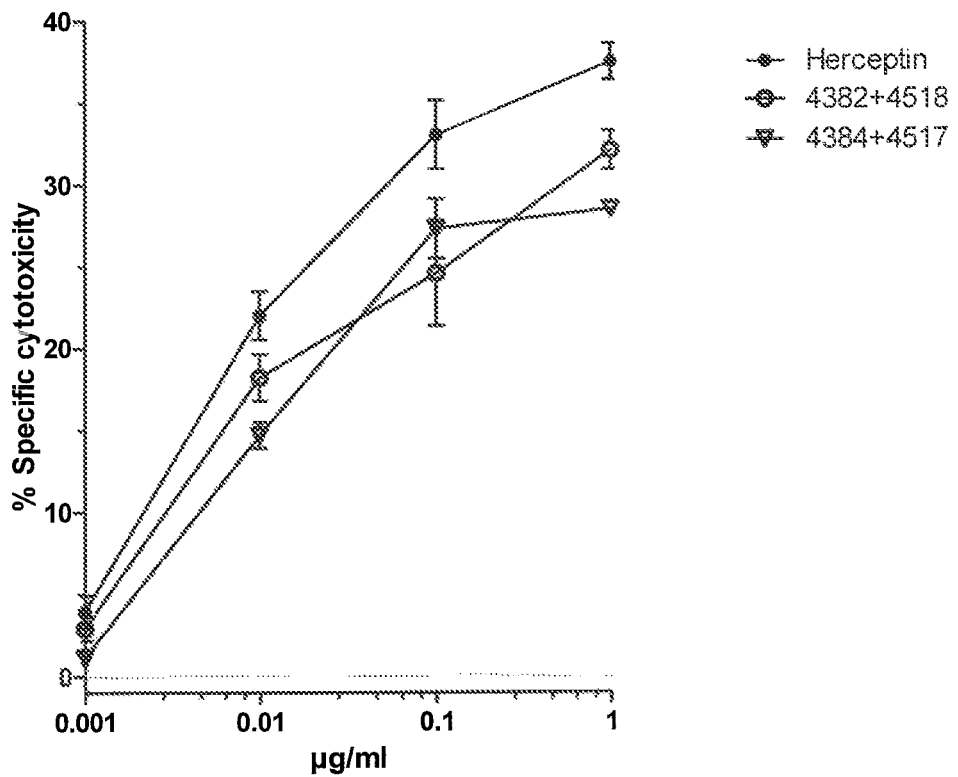
Figure 3D:
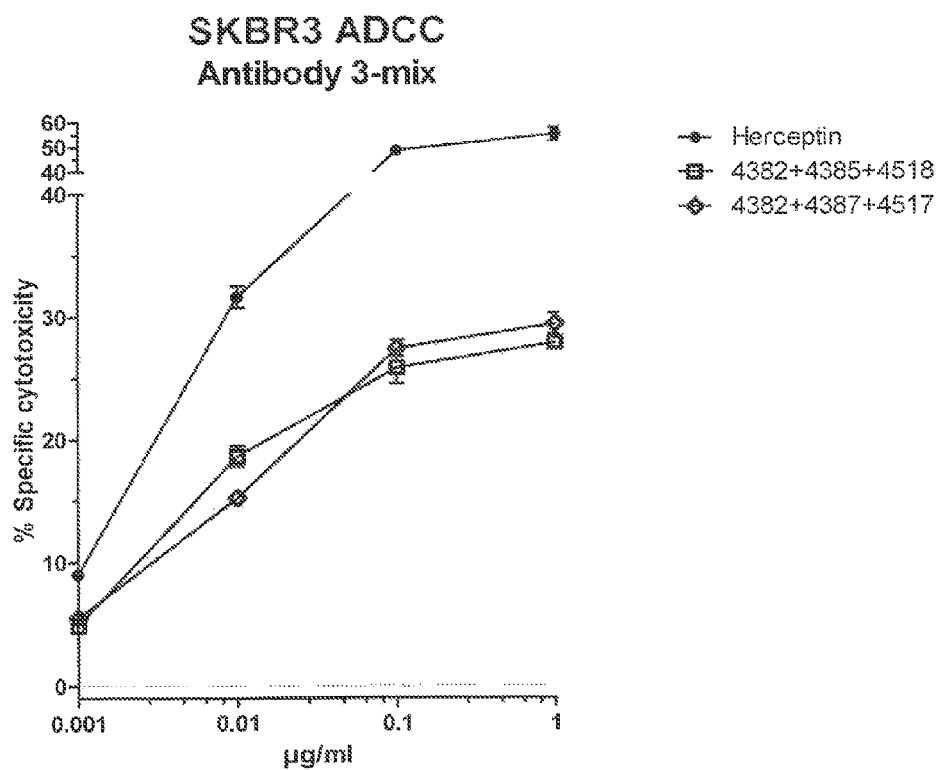

The term "antibody" or "antibody molecule" describes a functional component of serum and is often referred to either as a collection of molecules (antibodies or immunoglobulin) or as one molecule (the antibody molecule or immunoglobulin molecule). An antibody is capable of binding to or reacting with a specific antigenic determinant (the antigen or the antigenic epitope), which in turn may lead to induction of immunological effector mechanisms. An individual antibody is usually regarded as monospecific, and a composition of antibodies may be monoclonal (i.e., consisting of identical antibody molecules) or polyclonal (i.e., consisting of two or more different antibodies reacting with the same or different epitopes on the same antigen or even on distinct, different antigens). Each antibody has a unique structure that enables it to bind specifically to its corresponding antigen, and all natural antibodies have the same overall basic structure of two identical light chains and two identical heavy chains. Antibodies are also known collectively as immunoglobulins.

The terms "antibody" or "antibodies" as used herein are also intended to include chimeric and single chain antibodies, as well as binding fragments of antibodies, such as Fab, Fv fragments or single chain Fv (scFv) fragments, as well as multimeric forms such as dimeric IgA molecules or pentavalent IgM. An antibody may be of human or non-human origin, for example a murine or other rodent-derived antibody, or a chimeric, humanized or reshaped antibody based e.g. on a murine antibody.

Each heavy chain of an antibody typically includes a heavy chain variable region (VH) and a heavy chain constant region. The heavy chain constant region typically includes three domains, referred to as CH1, CH2 and CH3. Each antibody light chain typically includes a light chain variable region (VL) and a light chain constant region. The light chain constant region typically includes a single domain, referred to as CL. The VH and VL regions may be further subdivided into regions of hypervariability ("hypervariable regions", which may be hypervariable in sequence and/or in structurally defined loops). These are also referred to as complementarity determining regions (CDRs), which are interspersed with regions that are more conserved, termed framework regions (FRs). Each VH and VL typically includes three CDRs and four FRs, arranged from the amino terminus to the carboxy terminus in the following order: FR1, CDR1, FR2, CDR2, FR3, CDR3, FR4. The amino acid residues in the variable regions are often numbered using a standardized numbering method known as the Kabat numbering scheme (Kabat et al. (1991) Sequences of Proteins of Immunological Interest, 5th Ed. Public Health Service, National Institutes of Health, Bethesda, Md., USA).

In the appended sequence listing, the light chain (LC) DNA and amino acid sequences include both the light chain variable region (VL) sequence and the human kappa constant region sequence. As mentioned below in Example 1, the human kappa constant region starts with the amino acids -TVAAP- (Thr Val Ala Ala Pro) and ends at the C-terminal with the amino acids -NRGEC (Asn Arg Gly Glu Cys). Therefore, as used herein, the terms "light chain variable region sequence" or "VL" are understood to refer to the N-terminal part of a light chain sequence in the sequence listing before the start of the human kappa constant region (i.e. before the amino acids TVAAP).

The antibody numbers used herein in the context of whole antibodies, e.g. "antibody 4517", refer to the specific antibodies described in the examples and defined in the appended sequence listing. For example, antibody 4517 is an antibody with a heavy chain comprising the heavy chain variable region set forth in SEQ ID NO:2 and the IGHG1 heavy chain constant region set forth in SEQ ID NO:44, and a light chain with the sequence set forth in SEQ ID NO:4, where the light chain sequence as explained above includes both the light chain variable region sequence (residues 1-110 in SEQ ID NO:4) and the human kappa constant region sequence (residues 111-216 in SEQ ID NO:4).

When an antibody is said to be "derived from" or "based on" a specified antibody described herein, this means that the "derived" antibody comprises, depending on the particular context, one of the following: the heavy chain CDR3 sequence of said specified antibody; the heavy chain CDR3 sequence and the light chain CDR3 sequence of said specified antibody; the heavy chain CDR1, CDR2 and CDR3 sequences and light chain CDR1, CDR2 and CDR3 sequences of said specified antibody; or the heavy chain variable region sequence and the light chain variable region sequence of said specified antibody, or a humanized variant of said heavy chain variable region sequence and/or light chain variable region sequence, or a heavy chain and/or light chain variable region sequence having at least 80%, 85%, 90% or 95% sequence identity, such as at least 96%, 97%, 98% or 99% sequence identity, with the respective heavy chain and light chain variable region sequences. An antibody that is derived from or based on a specified antibody described herein will generally bind the same HER2 epitope as said specified antibody and will preferably exhibit substantially the same activity as said specified antibody.

The specificity of an antibody's interaction with a target antigen resides primarily in the amino acid residues located in the six CDRs of the heavy and light chain. The amino acid sequences within CDRs are therefore much more variable between individual antibodies than sequences outside of CDRs. Because CDR sequences are responsible for most antibody-antigen interactions, it is possible to express recombinant antibodies that mimic the properties of a specific naturally occurring antibody, or more generally any specific antibody with a given amino acid sequence, by constructing expression vectors that express CDR sequences from the specific antibody grafted into framework sequences from a different antibody. As a result, it is possible to "humanize" a non-human antibody and still substantially maintain the binding specificity and affinity of the original antibody. A more detailed discussion of humanization is provided below.

A "chimeric antibody" refers in its broadest sense to an antibody that contains one or more regions from one antibody and one or more regions from one or more other antibodies. As used herein, a "chimeric antibody" is generally an antibody that is partially of human origin and partially of non-human origin, i.e. derived in part from a non-human animal, for example a mouse or other rodent, or an avian such as a chicken. Chimeric antibodies are preferred over non-human antibodies in order to reduce the risk of a human anti-antibody response, e.g. a human anti-mouse antibody response in the case of a murine antibody. An example of a typical chimeric antibody is one in which the variable region sequences are murine sequences derived from immunization of a mouse, while the constant region sequences are human. In the case of a chimeric antibody, the non-human parts, i.e. typically the framework regions of the variable region sequences, may be subjected to further alteration in order to humanize the antibody.

The term "humanize" refers to the fact that where an antibody is wholly or partially of non-human origin, for example a murine antibody obtained from immunization of mice with an antigen of interest or a chimeric antibody based on such a murine antibody, it is possible to replace certain amino acids, in particular in the framework regions and constant domains of the heavy and light chains, in order to avoid or minimize an immune response in humans. It is known that all antibodies have the potential for eliciting a human anti-antibody response, which correlates to some extent with the degree of "humanness" of the antibody in question. Although it is not possible to precisely predict the immunogenicity and thereby the human anti-antibody response of a particular antibody, non-human antibodies tend to be more immunogenic than human antibodies. Chimeric antibodies, where the foreign (usually rodent) constant regions have been replaced with sequences of human origin, have been shown to be generally less immunogenic than antibodies of fully foreign origin, and the trend in therapeutic antibodies is towards humanized or fully human antibodies. For chimeric antibodies or other antibodies of non-human origin, it is therefore preferred that they be humanized to reduce the risk of a human anti-antibody response. For chimeric antibodies, humanization typically involves modification of the framework regions of the variable region sequences. Amino acid residues that are part of a complementarity determining region (CDR) will typically not be altered in connection with humanization, although in certain cases it may be desirable to alter individual CDR amino acid residues, for example to remove a glycosylation site, a deamidation site or an undesired cysteine residue.

Numerous methods for humanization of an antibody sequence are known in the art; see e.g. the review by Almagro & Fransson (2008) Front Biosci. 13: 1619-1633. One commonly used method is CDR grafting, which for e.g. a murine-derived chimeric antibody involves identification of human germline gene counterparts to the murine variable region genes and grafting of the murine CDR sequences into this framework. CDR grafting may be based on the Kabat CDR definitions, although a recent publication (Magdelaine-Beuzelin et al. (2007) Crit. Rev. Oncol Hematol. 64: 210-225) has suggested that the IMGT definition (www.imgt.org) may improve the result of the humanization. Since CDR grafting may reduce the binding specificity and affinity, and thus the biological activity, of a CDR grafted non-human antibody, back mutations may be introduced at selected positions of the CDR grafted antibody in order to retain the binding specificity and affinity of the parent antibody. Identification of positions for possible back mutations can be performed using information available in the literature and in antibody databases. Amino acid residues that are candidates for back mutations are typically those that are located at the surface of an antibody molecule, while residues that are buried or that have a low degree of surface exposure will not normally be altered. An alternative humanization technique to CDR grafting and back mutation is resurfacing, in which non-surface exposed residues of non-human origin are retained, while surface residues are altered to human residues.

As noted above, the present invention encompasses humanized antibodies, i.e. antibodies as otherwise described that have been subjected to humanization. These may also be referred to as "humanized variants" of an antibody of the invention. In particular, the terms "heavy chain variable region sequence" and "light chain variable region sequence" as used herein with reference to any specific amino acid sequence are intended to encompass not only that specific sequence but also any humanized variant thereof.

As used herein, a reference to a heavy chain variable region sequence or a light chain variable region sequence with a particular minimum level of sequence identity compared to a specified heavy chain or light chain variable region sequence, e.g. having at least 80%, 85%, 90% or 95% sequence identity with the reference sequence, such as at least 96%, 97%, 98% or 99% sequence identity, is intended to include, but not to be limited to, humanized variants of such reference sequence.

The term "recombinant antibody" refers to an antibody that is expressed from a cell or cell line transfected with an expression vector (or possibly more than one expression vector, typically two expression vectors) comprising the coding sequence of the antibody, where said coding sequence is not naturally associated with the cell.

The term "vector" refers to a nucleic acid molecule into which a nucleic acid sequence can be inserted for transport between different genetic environments and/or for expression in a host cell. A vector that carries regulatory elements for transcription of the nucleic acid sequence (at least a suitable promoter) is referred to as an "an expression vector". The terms "plasmid" and "vector" may be used interchangeably. Expression vectors used in the context of the present invention may be of any suitable type known in the art, e.g. a plasmid or a viral vector.

The term "polyclonal antibody" refers to a composition of two or more different antibody molecules which are capable of binding to or reacting with different specific antigenic determinants on the same or on different antigens. In the context of the present invention, the individual antibodies of a polyclonal antibody bind to different antigenic determinants of HER2. Preferably the individual antibodies of a polyclonal antibody of the invention bind to different epitopes of HER2, more preferably distinct and substantially non-overlapping epitopes. The variability of a polyclonal antibody is generally thought to be located in the variable regions of the antibody molecules. A "recombinant polyclonal anti-HER2 antibody composition" is a composition comprising a mixture of two or more monoclonal antibodies that bind HER2.

It is well-known in the art that antibodies exist as different isotypes, such as the human isotypes IgG1, IgG2, IgG3, IgG4, IgA1 and IgA2, or the murine isotypes IgG1, IgG2a, IgG2b, IgG3 and IgA. An antibody of the invention may be of any isotype. Although it is possible for the individual antibodies of a polyclonal antibody composition of the invention to include antibodies of more than one isotype, they are preferably all of the same isotype.

A recombinant antibody composition comprising "at least first and second recombinant anti-HER2 antibodies" will comprise at least two of the specified antibodies, but may include more than two of the anti-HER2 antibodies described herein. In certain cases such a recombinant antibody composition may include a relatively large number of individual anti-HER2 antibodies, e.g. up to 10 or more, such as up to 15 or 20, but will normally include less than 10 different anti-HER2 antibodies, i.e. 2, 3, 4, 5, 6, 7, 8 or 9 antibodies. Recombinant antibody compositions of the invention will more typically include not more than about 6 different anti-HER2 antibodies, and in many cases they will include not more than 4 different anti-HER2 antibodies. In preferred embodiments, a recombinant antibody composition of the invention will therefore include 2, 3 or 4 different anti-HER2 antibodies, typically 2 or 3 different anti-HER2 antibodies.

The term "CDR" or "complementarity determining region" refers to the "hypervariable" regions found in the variable domains of an antibody that are primarily responsible for determining the antibody's binding specificity. See the definition in Lefranc et al (2003), IMGT unique numbering for immunoglobulin and T cell receptor variable domains and Ig superfamily V-like domains, Dev. Comp Immunol. 27, 55-77. Each of the heavy and light chains of an antibody contain three CDR regions, referred to as CDR1, CDR2 and CDR3, of which CDR3 shows the greatest variability.

The term "epitope" is used to describe a part of a larger molecule (e.g. antigen or antigenic site) having antigenic or immunogenic activity in an animal. An epitope having immunogenic activity is a portion of a larger molecule that elicits an antibody response in an animal. An epitope having antigenic activity is a portion of a larger molecule to which an antibody immunospecifically binds as determined by any method known in the art. Antigenic epitopes are not necessarily immunogenic. An antigen is a substance to which an antibody or antibody fragment immunospecifically binds, e.g. a toxin, virus, bacteria, protein or DNA. An antigen or antigenic site often has more than one epitope, unless it is very small, and is often capable of stimulating an immune response. Epitopes may be linear or conformational. A linear epitope generally consists of about 6 to 10 adjacent amino acids on a protein molecule that are recognized by an antibody. In contrast, a conformational epitope consists of amino acids that are not arranged sequentially, but where an antibody recognizes a particular three-dimensional structure. When a protein molecule folds into a three-dimensional structure, the amino acids forming the epitope are juxtaposed, enabling the antibody to recognize the conformational epitope. In a denatured protein only linear epitopes are recognized. A conformational epitope, by definition, must be on the outside of the folded protein.

The term "distinct epitopes" refers to the fact that when two different antibodies of the invention bind distinct epitopes, there is less than 100% competition for antigen binding, preferably less than 80% competition for antigen binding, more preferably less than 50% competition for antigen binding, and most preferably as little competition as possible, such as less than about 25% competition for antigen binding. Antibodies capable of competing with each other for binding to the same antigen may bind the same or overlapping epitopes or may have a binding site in the close vicinity of one another, so that competition is mainly caused by steric hindrance. An analysis for "distinct epitopes" of antibody pairs may be performed by methods known in the art, for example by way of binding experiments under saturating antibody conditions using either FACS (fluorescence activated cell sorting) or other flow cytometry analysis on cells expressing HER2 and individual fluorescent labeled antibodies, or by Surface Plasmon Resonance (SPR) using HER2 antigen captured or conjugated to a flow cell surface. A method for determining competition between antibodies using SPR is described in the examples.

The distinct epitopes are preferably "non-overlapping" in the sense that two different anti-HER2 antibodies in a composition of the invention have a sufficiently low competition for antigen binding that the two antibodies are able to bind their respective epitopes simultaneously. It will be understood by persons skilled in the that there can be different degrees of overlap, and that distinct epitopes can be considered to be "non-overlapping" in spite of the presence of some degree of overlap, as long as the respective antibodies are able to substantially bind their epitopes. This is generally considered to be the case when the competition for antigen binding between two antibodies is less than about 50%.

Antibodies binding to different epitopes on the same antigen can have varying effects on the activity of the antigen to which they bind, depending on the location of the epitope. An antibody binding to an epitope in an active site of the antigen may block the function of the antigen completely, whereas another antibody binding at a different epitope may have no or little effect on the activity of the antigen alone. Such antibodies may, however, still activate complement and thereby result in the elimination of the antigen, and may result in synergistic effects when combined with one or more antibodies binding at different epitopes on the same antigen. In the context of the present invention, the epitope is preferably a portion of the extracellular domain of HER2. Antigens of the present invention are preferably extracellular domain HER2 proteins, polypeptides or fragments thereof to which an antibody or antibody fragment immunospecifically binds. A HER2 associated antigen may also be an analog or derivative of the extracellular domain of HER2 polypeptide or fragment thereof to which an antibody or antibody fragment immunospecifically binds.

The term "immunoglobulin" is commonly used as a collective designation of the mixture of antibodies found in blood or serum, but may also be used to designate a mixture of antibodies derived from other sources.

The term "cognate $V_H$ and $V_L$ coding pair" describes an original pair of $V_H$ and $V_L$ coding sequences contained within or derived from the same antibody-producing cell. Thus, a cognate $V_H$ and $V_L$ pair represents the $V_H$ and $V_L$ pairing originally present in the donor from which such a cell is derived. The term "an antibody expressed from a $V_H$ and $V_L$ coding pair" indicates that an antibody or an antibody fragment is produced from a vector, plasmid or other polynucleotide containing the $V_H$ and $V_L$ coding sequence. When a cognate $V_H$ and $V_L$ coding pair is expressed, either as a complete antibody or as a stable fragment thereof, they preserve the binding affinity and specificity of the antibody originally expressed from the cell they are derived from. A library of cognate pairs is also termed a repertoire or collection of cognate pairs, and may be kept individually or pooled.

By "protein" or "polypeptide" is meant any chain of amino acids, regardless of length or post-translational modification. Proteins can exist as monomers or multimers, comprising two or more assembled polypeptide chains, fragments of proteins, polypeptides, oligopeptides, or peptides.

The term "head-to-head promoters" refers to a promoter pair being placed in close proximity so that transcription of two gene fragments driven by the promoters occurs in opposite directions. Head-to-head promoters are also known as bi-directional promoters.

The term "transfection" is herein used as a broad term for introducing foreign DNA into a cell. The term is also meant to cover other functional equivalent methods for introducing foreign DNA into a cell, such as e.g., transformation, infection, transduction or fusion of a donor cell and an acceptor cell.

The term "HER2" (also known as HER2/neu and ErbB-2) stands for "Human Epidermal growth factor Receptor 2" as described above in the "Background of the invention" section. As used herein, it is intended to include variants, isoforms and species homologs of HER2. Preferably, binding of an antibody of the invention to HER2 inhibits the growth of cells expressing HER2 (i.e. typically tumor cells) by inhibiting formation of heteromeric complexes between HER2 and other ErbB family members, e.g. heterodimerization with EGFR or HER3.

As used herein, the term "inhibits growth" (e.g., referring to cells) is intended to include any measurable decrease in the proliferation (increase in number of cells) or metabolism of a cell when contacted with an anti-HER2 antibody as compared to the growth of the same cells in the absence of an anti-HER2 antibody, e.g. inhibition of growth of a cell culture by at least about 10%, and preferably more, such as at least about 20% or 30%, more preferably at least about 40% or 50%, such as at least about 60%, 70%, 80%, 90%, 99% or even 100%.

As used herein, the terms "inhibits dimerization" or "inhibits dimer formation" refer to any measurable reduction in the ability of HER2 to form dimers with e.g. EGFR, HER3 or HER4 as a result of binding of an anti-HER2 antibody compared to dimer formation in the absence of an anti-HER2 antibody.

The term "treatment" as used herein refers to administration of an anti-HER2 antibody or antibody composition of the invention in a sufficient amount to ease, reduce, ameliorate or eradicate (cure) symptoms or disease states. Administration of two or more anti-HER2 antibodies of the invention will generally be by way of simultaneous administration of the antibodies, preferably in the form of a composition containing all of the anti-HER2 antibodies to be used for treatment. However, it is also possible to administer two or more anti-HER2 antibodies of the invention separately. References herein to e.g. administration of a recombinant antibody composition comprising at least two anti-HER2 antibodies should therefore be understood as encompassing not only administration of a composition comprising the at least two antibodies as such, but also separate administration of the antibodies. Combinations of two or more anti-HER2 antibodies of the invention can thus be administered simultaneously, sequentially or separately.

The percent identity between two sequences, e.g. variable region sequences, refers to the number of identical positions shared by the sequences (calculated as # of identical positions/total # of positions×100), taking into account gaps that must be introduced for optimal alignment of the two sequences. The comparison of sequences and determination of percent identity between two sequences may be accomplished using readily available software. Suitable software programs are available from various sources, both for online use and for download, and for alignment of both protein and nucleotide sequences. One suitable program is ClustalW (Thompson et al. (1994) Nucleic Acids Res. 11; 22(22):4673-80), available from www.clustal.org, or alternatively e.g. from the European Bioinformatics Institute (www.ebi.ac.uk), which also provides various other protein and nucleotide informatics tools.

Particular Embodiments

One aspect of the invention relates to various novel anti-HER2 antibodies. In one embodiment, the invention thus relates to a recombinant anti-HER2 antibody comprising the heavy chain CDR3 sequence of any one of the antibodies referred to herein as antibodies 4380/4381, 4382, 4383, 4384, 4385, 4386, 4387, 4517, 4518 and 4519.

In another embodiment, the invention relates to a recombinant anti-HER2 antibody comprising the heavy chain CDR3 sequence and the light chain CDR3 sequence of any one of antibodies 4380/4381, 4382, 4383, 4384, 4385, 4386, 4387, 4517, 4518 and 4519.

In another embodiment, the invention relates to a recombinant anti-HER2 antibody comprising the heavy chain CDR1, CDR2 and CDR3 sequences and light chain CDR1, CDR2 and CDR3 sequences of any one of antibodies 4380/4381, 4382, 4383, 4384, 4385, 4386, 4387, 4517, 4518 and 4519.

In a further embodiment, the invention relates to a recombinant anti-HER2 antibody comprising the heavy chain variable region sequence and the light chain variable region sequence of any one of antibodies 4380/4381, 4382, 4383, 4384, 4385, 4386, 4387, 4517, 4518 and 4519, or comprising a humanized variant of said heavy chain and/or light chain variable region sequence, or comprising a heavy chain variable region sequence and a light chain variable region sequence each having at least 80%, 85%, 90% or 95% sequence identity with said heavy chain and light chain variable region sequences, such as at least 96%, 97%, 98% or 99% sequence identity with said sequences.

In a further embodiment, the invention relates to a recombinant anti-HER2 antibody that binds the same epitope as and which competes for binding with any of the antibodies defined above, as well as antibody compositions comprising one or more of such antibodies, preferably comprising at least two such antibodies, e.g. two or three such antibodies as described elsewhere herein.

Table 1 below shows the sequence ID numbers, as set forth in the appended sequence listing, for the DNA and amino acid sequences of the heavy chain variable regions (VH) and the light chains (LC) of antibodies 4380/4381, 4382, 4383, 4384, 4385, 4386, 4387, 4517, 4518 and 4519. As explained above, the light chain DNA and amino acid sequences in the sequence listing include both the light chain variable region (VL) sequence and the human kappa constant region sequence.

TABLE 1

Sequence ID numbers for the DNA and amino acid sequences of the heavy chain variable regions and light chains of selected anti-HER2 antibodies.

| Antibody No. | VH DNA seq. | VH protein seq. | LC DNA seq. | LC protein seq. |
|---|---|---|---|---|
| 4517 | 1 | 2 | 3 | 4 |
| 4518 | 5 | 6 | 7 | 8 |
| 4380/4381 | 9 | 10 | 11 | 12 |
| 4382 | 13 | 14 | 15 | 16 |
| 4383 | 17 | 18 | 19 | 20 |
| 4384 | 21 | 22 | 23 | 24 |
| 4385 | 25 | 26 | 27 | 28 |
| 4386 | 29 | 30 | 31 | 32 |
| 4387 | 33 | 34 | 35 | 36 |
| 4519 | 37 | 38 | 39 | 40 |

One particular embodiment of the invention is a recombinant anti-HER2 antibody comprising the heavy chain CDR3 sequence of antibody 4517, preferably comprising the heavy and light chain CDR3 sequences of antibody 4517, e.g. comprising the heavy and light chain CDR1, CDR2 and CDR3 sequences of antibody 4517, or comprising the heavy chain variable region sequence or a humanized variant thereof and the light chain variable region sequence or a humanized variant thereof of antibody 4517, or comprising a heavy chain variable region sequence and a light chain variable region sequence each having at least 80%, 85%, 90% or 95% sequence identity with the heavy chain and light chain variable region sequences, respectively, of antibody 4517.

Another particular embodiment of the invention is a recombinant anti-HER2 antibody comprising the heavy chain CDR3 sequence of antibody 4518, preferably comprising the heavy and light chain CDR3 sequences of antibody 4518, e.g. comprising the heavy and light chain CDR1, CDR2 and CDR3 sequences of antibody 4518, or comprising the heavy chain variable region sequence or a humanized variant thereof and the light chain variable region sequence or a humanized variant thereof of antibody 4518, or comprising a heavy chain variable region sequence and a light chain variable region sequence each having at least 80%, 85%, 90% or 95% sequence identity with the heavy chain and light chain variable region sequences, respectively, of antibody 4518.

Another particular embodiment of the invention is a recombinant anti-HER2 antibody comprising the heavy chain CDR3 sequence of antibody 4380/4381, preferably comprising the heavy and light chain CDR3 sequences of antibody 4380/4381, e.g. comprising the heavy and light chain CDR1, CDR2 and CDR3 sequences of antibody 4380/4381, or comprising the heavy chain variable region sequence or a humanized variant thereof and the light chain variable region sequence or a humanized variant thereof of antibody 4380/4381, or comprising a heavy chain variable region sequence and a light chain variable region sequence each having at least 80%, 85%, 90% or 95% sequence identity with the heavy chain and light chain variable region sequences, respectively, of antibody 4380/4381. In this embodiment, 4380 is preferred.

Antibody "4380/4381" refers to an antibody with the VH and LC amino acid sequences set forth in SEQ ID NO:10 and 12, respectively. As indicated in SEQ ID NO:12, the amino acid residue in position 40 can be Tyr or Thr. The only difference between antibodies 4380 and 4381 is that in antibody 4380 the residue in position 40 of the LC sequence is Tyr, while in antibody 4381 the residue in this position is Thr. In the original murine antibody there was a free Cys in this position. Among these two antibodies, 4380 is generally preferred.

Another particular embodiment of the invention is a recombinant anti-HER2 antibody comprising the heavy chain CDR3 sequence of antibody 4382, preferably comprising the heavy and light chain CDR3 sequences of antibody 4382, e.g. comprising the heavy and light chain CDR1, CDR2 and CDR3 sequences of antibody 4382, or comprising the heavy chain variable region sequence or a humanized variant thereof and the light chain variable region sequence or a humanized variant thereof of antibody 4382, or comprising a heavy chain variable region sequence and a light chain variable region sequence each having at least 80%, 85%, 90% or 95% sequence identity with the heavy chain and light chain variable region sequences, respectively, of antibody 4382.

Another particular embodiment of the invention is a recombinant anti-HER2 antibody comprising the heavy chain CDR3 sequence of antibody 4383, preferably comprising the heavy and light chain CDR3 sequences of antibody 4383, e.g. comprising the heavy and light chain CDR1, CDR2 and CDR3 sequences of antibody 4383, or comprising the heavy chain variable region sequence or a humanized variant thereof and the light chain variable region sequence or a humanized variant thereof of antibody 4383, or comprising a heavy chain variable region sequence and a light chain variable region sequence each having at least 80%, 85%, 90% or 95% sequence identity with the heavy chain and light chain variable region sequences, respectively, of antibody 4383.

Another particular embodiment of the invention is a recombinant anti-HER2 antibody comprising the heavy chain CDR3 sequence of antibody 4384, preferably comprising the heavy and light chain CDR3 sequences of antibody 4384, e.g. comprising the heavy and light chain CDR1, CDR2 and CDR3 sequences of antibody 4384, or comprising the heavy chain variable region sequence or a humanized variant thereof and the light chain variable region sequence or a humanized variant thereof of antibody 4384, or comprising a heavy chain variable region sequence and a light chain variable region sequence each having at least 80%, 85%, 90% or 95% sequence identity with the heavy chain and light chain variable region sequences, respectively, of antibody 4384.

Another particular embodiment of the invention is a recombinant anti-HER2 antibody comprising the heavy chain CDR3 sequence of antibody 4385, preferably comprising the heavy and light chain CDR3 sequences of antibody 4385, e.g. comprising the heavy and light chain CDR1, CDR2 and CDR3 sequences of antibody 4385, or comprising the heavy chain variable region sequence or a humanized variant thereof and the light chain variable region sequence or a humanized variant thereof of antibody 4385, or comprising a heavy chain variable region sequence and a light chain variable region sequence each having at least 80%, 85%, 90% or 95% sequence identity with the heavy chain and light chain variable region sequences, respectively, of antibody 4385.

Another particular embodiment of the invention is a recombinant anti-HER2 antibody comprising the heavy chain CDR3 sequence of antibody 4386, preferably comprising the heavy and light chain CDR3 sequences of antibody 4386, e.g. comprising the heavy and light chain CDR1, CDR2 and CDR3 sequences of antibody 4386, or comprising the heavy chain variable region sequence or a humanized variant thereof and the light chain variable region sequence or a humanized variant thereof of antibody 4386, or comprising a heavy chain variable region sequence and a light chain variable region sequence each having at least 80%, 85%, 90% or 95% sequence identity with the heavy chain and light chain variable region sequences, respectively, of antibody 4386.

Another particular embodiment of the invention is a recombinant anti-HER2 antibody comprising the heavy chain CDR3 sequence of antibody 4387, preferably comprising the heavy and light chain CDR3 sequences of antibody 4387, e.g. comprising the heavy and light chain CDR1, CDR2 and CDR3 sequences of antibody 4387, or comprising the heavy chain variable region sequence or a humanized variant thereof and the light chain variable region sequence or a humanized variant thereof of antibody 4387, or comprising a heavy chain variable region sequence and a light chain variable region sequence each having at least 80%, 85%, 90% or 95% sequence identity with the heavy chain and light chain variable region sequences, respectively, of antibody 4387.

Another particular embodiment of the invention is a recombinant anti-HER2 antibody comprising the heavy chain CDR3 sequence of antibody 4519, preferably comprising the heavy and light chain CDR3 sequences of antibody 4519, e.g. comprising the heavy and light chain CDR1, CDR2 and CDR3 sequences of antibody 4519, or comprising the heavy chain variable region sequence or a humanized variant thereof and the light chain variable region sequence or a humanized variant thereof of antibody 4519, or comprising a heavy chain variable region sequence and a light chain variable region sequence each having at least 80%, 85%, 90% or 95% sequence identity with the heavy chain and light chain variable region sequences, respectively, of antibody 4519.

In another aspect, the invention relates to a recombinant antibody composition comprising at least first and second recombinant anti-HER2 antibodies, wherein the first and second antibodies bind distinct epitopes of HER2, and wherein each of the first and second antibodies are selected from the group of antibodies outlined above. One embodiment of this aspect of the invention thus relates to a recombinant antibody composition comprising at least first and second recombinant anti-HER2 antibodies, wherein the first and second antibodies bind distinct epitopes of HER2, and wherein each of the first and second antibodies comprise the heavy chain CDR3 sequence of an antibody selected from the group consisting of antibodies 4380/4381, 4382, 4383, 4384, 4385, 4386, 4387, 4517, 4518 and 4519.

Another embodiment of this aspect of the invention relates to a recombinant antibody composition comprising at least first and second recombinant anti-HER2 antibodies, wherein the first and second antibodies bind distinct epitopes of HER2, and wherein each of the first and second antibodies comprise the heavy chain and light chain CDR3 sequences of an antibody selected from the group consisting of antibodies 4380/4381, 4382, 4383, 4384, 4385, 4386, 4387, 4517, 4518 and 4519.

A further embodiment of this aspect of the invention relates to a recombinant antibody composition comprising at least first and second recombinant anti-HER2 antibodies, wherein the first and second antibodies bind distinct epitopes of HER2, and wherein each of the first and second antibodies comprise the heavy chain and light chain CDR1, CDR2 and CDR3 sequences of an antibody selected from the group consisting of antibodies 4380/4381, 4382, 4383, 4384, 4385, 4386, 4387, 4517, 4518 and 4519.

A further embodiment of this aspect of the invention is a recombinant antibody composition comprising at least first and second recombinant anti-HER2 antibodies, wherein the first and second antibodies bind distinct epitopes of HER2, and wherein each of the first and second antibodies comprise the heavy chain variable region sequence or a humanized variant thereof and the light chain variable region sequence or a humanized variant thereof of an antibody selected from the group consisting of antibodies 4380/4381, 4382, 4383, 4384, 4385, 4386, 4387, 4517, 4518 and 4519; or wherein each of the first and second antibodies comprise a heavy chain variable region sequence and a light chain variable region sequence each having at least 80%, 85%, 90% or 95% sequence identity with the heavy chain and light chain variable region sequences, respectively, of an antibody selected from the group consisting of antibodies 4380/4381, 4382, 4383, 4384, 4385, 4386, 4387, 4517, 4518 and 4519.

A still further embodiment of this aspect of the invention is a recombinant antibody composition comprising at least first and second recombinant anti-HER2 antibodies, wherein the first and second antibodies bind distinct epitopes of HER2, and wherein the first and second antibodies are selected from the group consisting of antibodies 4380/4381, 4382, 4383, 4384, 4385, 4386, 4387, 4517, 4518 and 4519, or humanized variants thereof.

A still further embodiment of this aspect of the invention is a recombinant antibody composition comprising at least first and second recombinant anti-HER2 antibodies, wherein the first and second antibodies bind distinct epitopes of HER2, and wherein the first and second antibodies are selected from the group consisting of antibodies that bind to the same epitope as and compete for binding with antibodies 4380/4381, 4382, 4383, 4384, 4385, 4386, 4387, 4517, 4518 and 4519.

A further embodiment of the invention is an antibody composition comprising at least first and second recombinant anti-HER2 antibodies that bind distinct epitopes of HER2, wherein at least one of said antibodies is selected from the group consisting of:

(a) an antibody comprising the heavy chain CDR3 sequence (SEQ ID NO: 56) and the light chain CDR3 sequence (SEQ ID NO: 82) of antibody 4382;

(b) an antibody comprising the heavy chain CDR3 sequence (SEQ ID NO: 59) and the light chain CDR3 sequence (SEQ ID NO: 84) of antibody 4383;

(c) an antibody comprising the heavy chain CDR3 sequence (SEQ ID NO: 62) and the light chain CDR3 sequence (SEQ ID NO: 86) of antibody 4384;

(d) an antibody comprising the heavy chain CDR3 sequence (SEQ ID NO: 65) and the light chain CDR3 sequence (SEQ ID NO: 88) of antibody 4385;

(e) an antibody comprising the heavy chain CDR3 sequence (SEQ ID NO: 68) and the light chain CDR3 sequence (SEQ ID NO: 90) of antibody 4386;

(f) an antibody comprising the heavy chain CDR3 sequence (SEQ ID NO: 71) and the light chain CDR3 sequence (SEQ ID NO: 92) of antibody 4387;

(g) an antibody comprising the heavy chain CDR3 sequence (SEQ ID NO: 47) and the light chain CDR3 sequence (SEQ ID NO: 76) of antibody 4517;

(h) an antibody comprising the heavy chain CDR3 sequence (SEQ ID NO: 50) and the light chain CDR3 sequence (SEQ ID NO: 78) of antibody 4518;

(i) an antibody comprising the heavy chain CDR3 sequence (SEQ ID NO: 74) and the light chain CDR3 sequence (SEQ ID NO: 93) of antibody 4519; and (j) an antibody comprising the heavy chain CDR3 sequence (SEQ ID NO: 53) and the light chain CDR3 sequence (SEQ ID NO: 80) of antibody 4380.

Preferably, both of said first and second recombinant anti-HER2 antibodies are selected from antibodies (a)-(j) set forth above. The composition may also comprise at least a third recombinant anti-HER2 antibody, preferably an antibody selected from antibodies (a)-(j) above. In another embodiment, the antibody composition may comprise at least first and second recombinant anti-HER2 antibodies that bind distinct epitopes of HER2, wherein each of said first and second antibodies binds the same epitope as and competes for binding with one of antibodies (a)-(j) set forth above.

A still further embodiment of the invention is an antibody composition comprising at least first and second recombinant anti-HER2 antibodies that bind distinct epitopes of HER2, wherein at least one of said antibodies is selected from the group consisting of:

(A) an antibody comprising CDR1, CDR2 and CDR3 of the heavy chain variable region (SEQ ID NO: 14) and CDR1, CDR2 and CDR3 of the light chain variable region (SEQ ID NO: 16) of antibody 4382;

(B) an antibody comprising CDR1, CDR2 and CDR3 of the heavy chain variable region (SEQ ID NO: 18) and CDR1, CDR2 and CDR3 of the light chain variable region (SEQ ID NO: 20) of antibody 4383;

(C) an antibody comprising CDR1, CDR2 and CDR3 of the heavy chain variable region (SEQ ID NO: 22) and CDR1, CDR2 and CDR3 of the light chain variable region (SEQ ID NO: 24) of antibody 4384;

(D) an antibody comprising CDR1, CDR2 and CDR3 of the heavy chain variable region (SEQ ID NO: 26) and CDR1, CDR2 and CDR3 of the light chain variable region (SEQ ID NO: 28) of antibody 4385;

(E) an antibody comprising CDR1, CDR2 and CDR3 of the heavy chain variable region (SEQ ID NO: 30) and CDR1, CDR2 and CDR3 of the light chain variable region (SEQ ID NO: 32) of antibody 4386;

(F) an antibody comprising CDR1, CDR2 and CDR3 of the heavy chain variable region (SEQ ID NO: 34) and CDR1, CDR2 and CDR3 of the light chain variable region (SEQ ID NO: 36) of antibody 4387;

(G) an antibody comprising CDR1, CDR2 and CDR3 of the heavy chain variable region (SEQ ID NO: 2) and CDR1, CDR2 and CDR3 of the light chain variable region (SEQ ID NO: 4) of antibody 4517;

(H) an antibody comprising CDR1, CDR2 and CDR3 of the heavy chain variable region (SEQ ID NO: 6) and CDR1, CDR2 and CDR3 of the light chain variable region (SEQ ID NO: 8) of antibody 4518;

(I) an antibody comprising CDR1, CDR2 and CDR3 of the heavy chain variable region (SEQ ID NO: 38) and CDR1, CDR2 and CDR3 of the light chain variable region (SEQ ID NO: 40) of antibody 4519; and (J) an antibody comprising CDR1, CDR2 and CDR3 of the heavy chain variable region (SEQ ID NO: 10) and CDR1, CDR2 and CDR3 of the light chain variable region (SEQ ID NO: 12) of antibody 4380.

In this embodiment, both of said first and second recombinant anti-HER2 antibodies are preferably selected from antibodies (A)-(J) set forth above. The composition may also comprise at least a third recombinant anti-HER2 antibody, preferably an antibody selected from antibodies (A)-(J) above. In another embodiment, the antibody composition may comprise at least first and second recombinant anti-HER2 antibodies that bind distinct epitopes of HER2, wherein each of said first and second antibodies binds the same epitope as and competes for binding with one of antibodies (A)-(J) set forth above.

One particular embodiment of this aspect of the invention relates to a recombinant antibody composition comprising at least first and second recombinant antibodies, wherein the first and second antibodies are:

antibodies 4380 and 4382, or humanized variants thereof;

an antibody comprising the heavy chain CDR3 sequence of antibody 4380, and an antibody comprising the heavy chain CDR3 sequence of antibody 4382;

an antibody comprising the heavy and light chain CDR3 sequences of antibody 4380, and an antibody comprising the heavy and light chain CDR3 sequences of antibody 4382;

an antibody comprising the heavy and light chain CDR1, CDR2 and CDR3 sequences of antibody 4380, and an antibody comprising the heavy and light chain CDR1, CDR2 and CDR3 sequences of antibody 4382;

an antibody comprising the heavy and light chain variable region sequences of antibody 4380, and an antibody comprising the heavy and light chain variable region sequences of antibody 4382; or an antibody comprising heavy and light chain variable region sequences each having at least 80%, 85%, 90% or 95% sequence identity with the heavy and light chain variable region sequences, respectively, of antibody 4380, and an antibody comprising heavy and light chain variable region sequences each having at least 80%, 85%, 90% or 95% sequence identity with the heavy and light chain variable region sequences, respectively, of antibody 4382.

Further embodiments of this aspect of the invention relate to compositions based on antibodies 4380 and 4382, and comprising at least one additional antibody, in particular selected from antibodies based on 4385, 4517 and 4518. One such embodiment relates to a recombinant antibody composition comprising first, second and third recombinant antibodies, wherein the first, second and third antibodies are:

antibodies 4380, 4382 and 4385, or humanized variants thereof;

an antibody comprising the heavy chain CDR3 sequence of antibody 4380, an antibody comprising the heavy chain CDR3 sequence of antibody 4382, and an antibody comprising the heavy chain CDR3 sequence of antibody 4385;

an antibody comprising the heavy and light chain CDR3 sequences of antibody 4380, an antibody comprising the heavy and light chain CDR3 sequences of antibody 4382, and an antibody comprising the heavy and light chain CDR3 sequences of antibody 4385;

an antibody comprising the heavy and light chain CDR1, CDR2 and CDR3 sequences of antibody 4380, an antibody comprising the heavy and light chain CDR1, CDR2 and CDR3 sequences of antibody 4382, and an antibody comprising the heavy and light chain CDR1, CDR2 and CDR3 sequences of antibody 4385;

an antibody comprising the heavy and light chain variable region sequences of antibody 4380, an antibody comprising the heavy and light chain variable region sequences of antibody 4382, and an antibody comprising the heavy and light chain variable region sequences of antibody 4385; or an antibody comprising heavy and light chain variable region sequences each having at least 80%, 85%, 90% or 95% sequence identity with the heavy and light chain variable region sequences, respectively, of antibody 4380, an antibody comprising heavy and light chain variable region sequences each having at least 80%, 85%, 90% or 95% sequence identity with the heavy and light chain variable region sequences, respectively, of antibody 4382, and an antibody comprising heavy and light chain variable region sequences each having at least 80%, 85%, 90% or 95% sequence identity with the heavy and light chain variable region sequences, respectively, of antibody 4385.

Another such embodiment relates to a recombinant antibody composition comprising first, second and third recombinant antibodies, wherein the first, second and third antibodies are:

antibodies 4380, 4382 and 4517, or humanized variants thereof;

an antibody comprising the heavy chain CDR3 sequence of antibody 4380, an antibody comprising the heavy chain CDR3 sequence of antibody 4382, and an antibody comprising the heavy chain CDR3 sequence of antibody 4517;

an antibody comprising the heavy and light chain CDR3 sequences of antibody 4380, an antibody comprising the heavy and light chain CDR3 sequences of antibody 4382, and an antibody comprising the heavy and light chain CDR3 sequences of antibody 4517;

an antibody comprising the heavy and light chain CDR1, CDR2 and CDR3 sequences of antibody 4380, an antibody comprising the heavy and light chain CDR1, CDR2 and CDR3 sequences of antibody 4382, and an antibody comprising the heavy and light chain CDR1, CDR2 and CDR3 sequences of antibody 4517;

an antibody comprising the heavy and light chain variable region sequences of antibody 4380, an antibody comprising the heavy and light chain variable region sequences of antibody 4382, and an antibody comprising the heavy and light chain variable region sequences of antibody 4517; or an antibody comprising heavy and light chain variable region sequences each having at least 80%, 85%, 90% or 95% sequence identity with the heavy and light chain variable region sequences, respectively, of antibody 4380, an antibody comprising heavy and light chain variable region sequences each having at least 80%, 85%, 90% or 95% sequence identity with the heavy and light chain variable region sequences, respectively, of antibody 4382, and an antibody comprising heavy and light chain variable region sequences each having at least 80%, 85%, 90% or 95% sequence identity with the heavy and light chain variable region sequences, respectively, of antibody 4517.

Another such embodiment relates to a recombinant antibody composition comprising first, second and third recombinant antibodies, wherein the first, second and third antibodies are:

antibodies 4380, 4382 and 4518, or humanized variants thereof;

an antibody comprising the heavy chain CDR3 sequence of antibody 4380, an antibody comprising the heavy chain CDR3 sequence of antibody 4382, and an antibody comprising the heavy chain CDR3 sequence of antibody 4518;

an antibody comprising the heavy and light chain CDR3 sequences of antibody 4380, an antibody comprising the heavy and light chain CDR3 sequences of antibody 4382, and an antibody comprising the heavy and light chain CDR3 sequences of antibody 4518;

an antibody comprising the heavy and light chain CDR1, CDR2 and CDR3 sequences of antibody 4380, an antibody comprising the heavy and light chain CDR1, CDR2 and CDR3 sequences of antibody 4382, and an antibody comprising the heavy and light chain CDR1, CDR2 and CDR3 sequences of antibody 4518;

an antibody comprising the heavy and light chain variable region sequences of antibody 4380, an antibody comprising the heavy and light chain variable region sequences of antibody 4382, and an antibody comprising the heavy and light chain variable region sequences of antibody 4518; or an antibody comprising heavy and light chain variable region sequences each having at least 80%, 85%, 90% or 95% sequence identity with the heavy and light chain variable region sequences, respectively, of antibody 4380, an antibody comprising heavy and light chain variable region sequences each having at least 80%, 85%, 90% or 95% sequence identity with the heavy and light chain variable region sequences, respectively, of antibody 4382, and an antibody comprising heavy and light chain variable region sequences each having at least 80%, 85%, 90% or 95% sequence identity with the heavy and light chain variable region sequences, respectively, of antibody 4518.

A still further embodiment relates to a recombinant antibody composition comprising first, second, third and fourth recombinant antibodies, wherein the first, second, third and fourth antibodies are:

antibodies 4380, 4382, 4385 and 4518, or humanized variants thereof;

an antibody comprising the heavy chain CDR3 sequence of antibody 4380, an antibody comprising the heavy chain CDR3 sequence of antibody 4382, an antibody comprising the heavy chain CDR3 sequence of antibody 4385, and an antibody comprising the heavy chain CDR3 sequence of antibody 4518;

an antibody comprising the heavy and light chain CDR3 sequences of antibody 4380, an antibody comprising the heavy and light chain CDR3 sequences of antibody 4382, an antibody comprising the heavy and light chain CDR3 sequences of antibody 4385, and an antibody comprising the heavy and light chain CDR3 sequences of antibody 4518;

an antibody comprising the heavy and light chain CDR1, CDR2 and CDR3 sequences of antibody 4380, an antibody comprising the heavy and light chain CDR1, CDR2 and CDR3 sequences of antibody 4382, an antibody comprising the heavy and light chain CDR1, CDR2 and CDR3 sequences of antibody 4385, and an antibody comprising the heavy and light chain CDR1, CDR2 and CDR3 sequences of antibody 4518; or an antibody comprising the heavy and light chain variable region sequences of antibody 4380, an antibody comprising the heavy and light chain variable region sequences of antibody 4382, an antibody comprising the heavy and light chain variable region sequences of antibody 4385, and an antibody comprising the heavy and light chain variable region sequences of antibody 4518;

an antibody comprising heavy and light chain variable region sequences each having at least 80%, 85%, 90% or 95% sequence identity with the heavy and light chain variable region sequences, respectively, of antibody 4380, an antibody comprising heavy and light chain variable region sequences each having at least 80%, 85%, 90% or 95% sequence identity with the heavy and light chain variable region sequences, respectively, of antibody 4382, an antibody comprising heavy and light chain variable region sequences each having at least 80%, 85%, 90% or 95% sequence identity with the heavy and light chain variable region sequences, respectively, of antibody 4385, and an antibody comprising heavy and light chain variable region sequences each having at least 80%, 85%, 90% or 95% sequence identity with the heavy and light chain variable region sequences, respectively, of antibody 4518.

Another embodiment of this aspect of the invention relates to a recombinant antibody composition comprising at least first and second recombinant antibodies, wherein the first and second antibodies are:

antibodies 4380 and 4383, or humanized variants thereof;

an antibody comprising the heavy chain CDR3 sequence of antibody 4380, and an antibody comprising the heavy chain CDR3 sequence of antibody 4383;

an antibody comprising the heavy and light chain CDR3 sequences of antibody 4380, and an antibody comprising the heavy and light chain CDR3 sequences of antibody 4383;

an antibody comprising the heavy and light chain CDR1, CDR2 and CDR3 sequences of antibody 4380, and an antibody comprising the heavy and light chain CDR1, CDR2 and CDR3 sequences of antibody 4383;

an antibody comprising the heavy and light chain variable region sequences of antibody 4380, and an antibody comprising the heavy and light chain variable region sequences of antibody 4383; or an antibody comprising heavy and light chain variable region sequences each having at least 80%, 85%, 90% or 95% sequence identity with the heavy and light chain variable region sequences, respectively, of antibody 4380, and an antibody comprising heavy and light chain variable region sequences each having at least 80%, 85%, 90% or 95% sequence identity with the heavy and light chain variable region sequences, respectively, of antibody 4383.

A further embodiment of this aspect of the invention relates to compositions based on antibodies 4380 and 4383, and comprising at least one additional antibody. One such embodiment relates to a recombinant antibody composition comprising first, second and third recombinant antibodies, wherein the first, second and third antibodies are:

antibodies 4380, 4383 and 4384, or humanized variants thereof;

an antibody comprising the heavy chain CDR3 sequence of antibody 4380, an antibody comprising the heavy chain CDR3 sequence of antibody 4383, and an antibody comprising the heavy chain CDR3 sequence of antibody 4384;

an antibody comprising the heavy and light chain CDR3 sequences of antibody 4380, an antibody comprising the heavy and light chain CDR3 sequences of antibody 4383, and an antibody comprising the heavy and light chain CDR3 sequences of antibody 4384;

an antibody comprising the heavy and light chain CDR1, CDR2 and CDR3 sequences of antibody 4380, an antibody comprising the heavy and light chain CDR1, CDR2 and CDR3 sequences of antibody 4383, and an antibody comprising the heavy and light chain CDR1, CDR2 and CDR3 sequences of antibody 4384;

an antibody comprising the heavy and light chain variable region sequences of antibody 4380, an antibody comprising the heavy and light chain variable region sequences of antibody 4383, and an antibody comprising the heavy and light chain variable region sequences of antibody 4384; or an antibody comprising heavy and light chain variable region sequences each having at least 80%, 85%, 90% or 95% sequence identity with the heavy and light chain variable region sequences, respectively, of antibody 4380, an antibody comprising heavy and light chain variable region sequences each having at least 80%, 85%, 90% or 95% sequence identity with the heavy and light chain variable region sequences, respectively, of antibody 4383, and an antibody comprising heavy and light chain variable region sequences each having at least 80%, 85%, 90% or 95% sequence identity with the heavy and light chain variable region sequences, respectively, of antibody 4384.

Another embodiment of this aspect of the invention relates to a recombinant antibody composition comprising at least first and second recombinant antibodies, wherein the first and second antibodies are:

antibodies 4380 and 4384, or humanized variants thereof;

an antibody comprising the heavy chain CDR3 sequence of antibody 4380, and an antibody comprising the heavy chain CDR3 sequence of antibody 4384;

an antibody comprising the heavy and light chain CDR3 sequences of antibody 4380, and an antibody comprising the heavy and light chain CDR3 sequences of antibody 4384;

an antibody comprising the heavy and light chain CDR1, CDR2 and CDR3 sequences of antibody 4380, and an antibody comprising the heavy and light chain CDR1, CDR2 and CDR3 sequences of antibody 4384;

an antibody comprising the heavy and light chain variable region sequences of antibody 4380, and an antibody comprising the heavy and light chain variable region sequences of antibody 4384; or an antibody comprising heavy and light chain variable region sequences each having at least 80%, 85%, 90% or 95% sequence identity with the heavy and light chain variable region sequences, respectively, of antibody 4380, and an antibody comprising heavy and light chain variable region sequences each having at least 80%, 85%, 90% or 95% sequence identity with the heavy and light chain variable region sequences, respectively, of antibody 4384.

Further embodiments of this aspect of the invention relate to compositions based on antibodies 4380 and 4384, and comprising at least one additional antibody, in particular selected from antibodies based on 4385, 4517, 4518 and 4519. One such embodiment relates to a recombinant antibody composition comprising first, second and third recombinant antibodies, wherein the first, second and third antibodies are:

antibodies 4380, 4384 and 4517, or humanized variants thereof;

an antibody comprising the heavy chain CDR3 sequence of antibody 4380, an antibody comprising the heavy chain CDR3 sequence of antibody 4380, and an antibody comprising the heavy chain CDR3 sequence of antibody 4517;

an antibody comprising the heavy and light chain CDR3 sequences of antibody 4380, an antibody comprising the heavy, and light chain CDR3 sequences of antibody 4384, and an antibody comprising the heavy and light chain CDR3 sequences of antibody 4517;

an antibody comprising the heavy and light chain CDR1, CDR2 and CDR3 sequences of antibody 4380, an antibody comprising the heavy and light chain CDR1, CDR2 and CDR3 sequences of antibody 4384, and an antibody comprising the heavy and light chain CDR1, CDR2 and CDR3 sequences of antibody 4517;

an antibody comprising the heavy and light chain variable region sequences of antibody 4380, an antibody comprising the heavy and light chain variable region sequences of antibody 4384, and an antibody comprising the heavy and light chain variable region sequences of antibody 4517; or an antibody comprising heavy and light chain variable region sequences each having at least 80%, 85%, 90% or 95% sequence identity with the heavy and light chain variable region sequences, respectively, of antibody 4380, an antibody comprising heavy and light chain variable region sequences each having at least 80%, 85%, 90% or 95% sequence identity with the heavy and light chain variable region sequences, respectively, of antibody 4384, and an antibody comprising heavy and light chain variable region sequences each having at least 80%, 85%, 90% or 95% sequence identity with the heavy and light chain variable region sequences, respectively, of antibody 4517.

Another such embodiment relates to a recombinant antibody composition comprising first, second and third recombinant antibodies, wherein the first, second and third antibodies are:

antibodies 4380, 4384 and 4518, or humanized variants thereof;

an antibody comprising the heavy chain CDR3 sequence of antibody 4380, an antibody comprising the heavy chain CDR3 sequence of antibody 4380, and an antibody comprising the heavy chain CDR3 sequence of antibody 4518;

an antibody comprising the heavy and light chain CDR3 sequences of antibody 4380, an antibody comprising the heavy and light chain CDR3 sequences of antibody 4384, and an antibody comprising the heavy and light chain CDR3 sequences of antibody 4518;

an antibody comprising the heavy and light chain CDR1, CDR2 and CDR3 sequences of antibody 4380, an antibody comprising the heavy and light chain CDR1, CDR2 and CDR3 sequences of antibody 4384, and an antibody comprising the heavy and light chain CDR1, CDR2 and CDR3 sequences of antibody 4518;

an antibody comprising the heavy and light chain variable region sequences of antibody 4380, an antibody comprising the heavy and light chain variable region sequences of antibody 4384, and an antibody comprising the heavy and light chain variable region sequences of antibody 4518; or an antibody comprising heavy and light chain variable region sequences each having at least 80%, 85%, 90% or 95% sequence identity with the heavy and light chain variable region sequences, respectively, of antibody 4380, an antibody comprising heavy and light chain variable region sequences each having at least 80%, 85%, 90% or 95% sequence identity with the heavy and light chain variable region sequences, respectively, of antibody 4384, and an antibody comprising heavy and light chain variable region sequences each having at least 80%, 85%, 90% or 95% sequence identity with the heavy and light chain variable region sequences, respectively, of antibody 4518.

Another such embodiment relates to a recombinant antibody composition comprising first, second and third recombinant antibodies, wherein the first, second and third antibodies are:

antibodies 4380, 4384 and 4519, or humanized variants thereof;

an antibody comprising the heavy chain CDR3 sequence of antibody 4380, an antibody comprising the heavy chain CDR3 sequence of antibody 4380, and an antibody comprising the heavy chain CDR3 sequence of antibody 4519;

an antibody comprising the heavy and light chain CDR3 sequences of antibody 4380, an antibody comprising the heavy and light chain CDR3 sequences of antibody 4384, and an antibody comprising the heavy and light chain CDR3 sequences of antibody 4519;

an antibody comprising the heavy and light chain CDR1, CDR2 and CDR3 sequences of antibody 4380, an antibody comprising the heavy and light chain CDR1, CDR2 and CDR3 sequences of antibody 4384, and an antibody comprising the heavy and light chain CDR1, CDR2 and CDR3 sequences of antibody 4519;

an antibody comprising the heavy and light chain variable region sequences of antibody 4380, an antibody comprising the heavy and light chain variable region sequences of antibody 4384, and an antibody comprising the heavy and light chain variable region sequences of antibody 4519; or an antibody comprising heavy and light chain variable region sequences each having at least 80%, 85%, 90% or 95% sequence identity with the heavy and light chain variable region sequences, respectively, of antibody 4380, an antibody comprising heavy and light chain variable region sequences each having at least 80%, 85%, 90% or 95% sequence identity with the heavy and light chain variable region sequences, respectively, of antibody 4384, and an antibody comprising heavy and light chain variable region sequences each having at least 80%, 85%, 90% or 95% sequence identity with the heavy and light chain variable region sequences, respectively, of antibody 4519.

A still further embodiment relates to a recombinant antibody composition comprising first, second, third and fourth recombinant antibodies, wherein the first, second, third and fourth antibodies are:

antibodies 4380, 4384, 4385 and 4518, or humanized variants thereof;

an antibody comprising the heavy chain CDR3 sequence of antibody 4380, an antibody comprising the heavy chain CDR3 sequence of antibody 4384, an antibody comprising the heavy chain CDR3 sequence of antibody 4385, and an antibody comprising the heavy chain CDR3 sequence of antibody 4518;

an antibody comprising the heavy and light chain CDR3 sequences of antibody 4380, an antibody comprising the heavy and light chain CDR3 sequences of antibody 4384, an antibody comprising the heavy and light chain CDR3 sequences of antibody 4385, and an antibody comprising the heavy and light chain CDR3 sequences of antibody 4518;

an antibody comprising the heavy and light chain CDR1, CDR2 and CDR3 sequences of antibody 4380, an antibody comprising the heavy and light chain CDR1, CDR2 and CDR3 sequences of antibody 4384, an antibody comprising the heavy and light chain CDR1, CDR2 and CDR3 sequences of antibody 4385, and an antibody comprising the heavy and light chain CDR1, CDR2 and CDR3 sequences of antibody 4518;

an antibody comprising the heavy and light chain variable region sequences of antibody 4380, an antibody comprising the heavy and light chain variable region sequences of antibody 4384, an antibody comprising the heavy and light chain variable region sequences of antibody 4385, and an antibody comprising the heavy and light chain variable region sequences of antibody 4518; or an antibody comprising heavy and light chain variable region sequences each having at least 80%, 85%, 90% or 95% sequence identity with the heavy and light chain variable region sequences, respectively, of antibody 4380, an antibody comprising heavy and light chain variable region sequences each having at least 80%, 85%, 90% or 95% sequence identity with the heavy and light chain variable region sequences, respectively, of antibody 4384, an antibody comprising heavy and light chain variable region sequences each having at least 80%, 85%, 90% or 95% sequence identity with the heavy and light chain variable region sequences, respectively, of antibody 4385, and an antibody comprising heavy and light chain variable region sequences each having at least 80%, 85%, 90% or 95% sequence identity with the heavy and light chain variable region sequences, respectively, of antibody 4518.

Another embodiment of this aspect of the invention relates to a recombinant antibody composition comprising at least first and second recombinant antibodies, wherein the first and second antibodies are:

antibodies 4380 and 4385, or humanized variants thereof;

an antibody comprising the heavy chain CDR3 sequence of antibody 4380, and an antibody comprising the heavy chain CDR3 sequence of antibody 4385;

an antibody comprising the heavy and light chain CDR3 sequences of antibody 4380, and an antibody comprising the heavy and light chain CDR3 sequences of antibody 4385;

an antibody comprising the heavy and light chain CDR1, CDR2 and CDR3 sequences of antibody 4380, and an antibody comprising the heavy and light chain CDR1, CDR2 and CDR3 sequences of antibody 4385;

an antibody comprising the heavy and light chain variable region sequences of antibody 4380, and an antibody comprising the heavy and light chain variable region sequences of antibody 4385; or an antibody comprising heavy and light chain variable region sequences each having at least 80%, 85%, 90% or 95% sequence identity with the heavy and light chain variable region sequences, respectively, of antibody 4380, and an antibody comprising heavy and light chain variable region sequences each having at least 80%, 85%, 90% or 95% sequence identity with the heavy and light chain variable region sequences, respectively, of antibody 4385.

Another embodiment of this aspect of the invention relates to a recombinant antibody composition comprising at least first and second recombinant antibodies, wherein the first and second antibodies are:

antibodies 4380 and 4386, or humanized variants thereof;

an antibody comprising the heavy chain CDR3 sequence of antibody 4380, and an antibody comprising the heavy chain CDR3 sequence of antibody 4386;

an antibody comprising the heavy and light chain CDR3 sequences of antibody 4380, and an antibody comprising the heavy and light chain CDR3 sequences of antibody 4386;

an antibody comprising the heavy and light chain CDR1, CDR2 and CDR3 sequences of antibody 4380, and an antibody comprising the heavy and light chain CDR1, CDR2 and CDR3 sequences of antibody 4386;

an antibody comprising the heavy and light chain variable region sequences of antibody 4380, and an antibody comprising the heavy and light chain variable region sequences of antibody 4386; or an antibody comprising heavy and light chain variable region sequences each having at least 80%, 85%, 90% or 95% sequence identity with the heavy and light chain variable region sequences, respectively, of antibody 4380, and an antibody comprising heavy and light chain variable region sequences each having at least 80%, 85%, 90% or 95% sequence identity with the heavy and light chain variable region sequences, respectively, of antibody 4386.

Another embodiment of this aspect of the invention relates to a recombinant antibody composition comprising at least first and second recombinant antibodies, wherein the first and second antibodies are:

antibodies 4380 and 4387, or humanized variants thereof;

an antibody comprising the heavy chain CDR3 sequence of antibody 4380, and an antibody comprising the heavy chain CDR3 sequence of antibody 4387;

an antibody comprising the heavy and light chain CDR3 sequences of antibody 4380, and an antibody comprising the heavy and light chain CDR3 sequences of antibody 4387;

an antibody comprising the heavy and light chain CDR1, CDR2 and CDR3 sequences of antibody 4380, and an antibody comprising the heavy and light chain CDR1, CDR2 and CDR3 sequences of antibody 4387;

an antibody comprising the heavy and light chain variable region sequences of antibody 4380, and an antibody comprising the heavy and light chain variable region sequences of antibody 4387; or an antibody comprising heavy and light chain variable region sequences each having at least 80%, 85%, 90% or 95% sequence identity with the heavy and light chain variable region sequences, respectively, of antibody 4380, and an antibody comprising heavy and light chain variable region sequences each having at least 80%, 85%, 90% or 95% sequence identity with the heavy and light chain variable region sequences, respectively, of antibody 4387.

Another embodiment of this aspect of the invention relates to a recombinant antibody composition comprising at least first and second recombinant antibodies, wherein the first and second antibodies are:

antibodies 4380 and 4517, or humanized variants thereof;

an antibody comprising the heavy chain CDR3 sequence of antibody 4380, and an antibody comprising the heavy chain CDR3 sequence of antibody 4517;

an antibody comprising the heavy and light chain CDR3 sequences of antibody 4380, and an antibody comprising the heavy and light chain CDR3 sequences of antibody 4517;

an antibody comprising the heavy and light chain CDR1, CDR2 and CDR3 sequences of antibody 4380, and an antibody comprising the heavy and light chain CDR1, CDR2 and CDR3 sequences of antibody 4517;

an antibody comprising the heavy and light chain variable region sequences of antibody 4380, and an antibody comprising the heavy and light chain variable region sequences of antibody 4517; or an antibody comprising heavy and light chain variable region sequences each having at least 80%, 85%, 90% or 95% sequence identity with the heavy and light chain variable region sequences, respectively, of antibody 4380, and an antibody comprising heavy and light chain variable region sequences each having at least 80%, 85%, 90% or 95% sequence identity with the heavy and light chain variable region sequences, respectively, of antibody 4517.

Another embodiment of this aspect of the invention relates to a recombinant antibody composition comprising at least first and second recombinant antibodies, wherein the first and second antibodies are:

antibodies 4380 and 4518, or humanized variants thereof;

an antibody comprising the heavy chain CDR3 sequence of antibody 4380, and an antibody comprising the heavy chain CDR3 sequence of antibody 4518;

an antibody comprising the heavy and light chain CDR3 sequences of antibody 4380, and an antibody comprising the heavy and light chain CDR3 sequences of antibody 4518;

an antibody comprising the heavy and light chain CDR1, CDR2 and CDR3 sequences of antibody 4380, and an antibody comprising the heavy and light chain CDR1, CDR2 and CDR3 sequences of antibody 4518;

an antibody comprising the heavy and light chain variable region sequences of antibody 4380, and an antibody comprising the heavy and light chain variable region sequences of antibody 4518; or an antibody comprising heavy and light chain variable region sequences each having at least 80%, 85%, 90% or 95% sequence identity with the heavy and light chain variable region sequences, respectively, of antibody 4380, and an antibody comprising heavy and light chain variable region sequences each having at least 80%, 85%, 90% or 95% sequence identity with the heavy and light chain variable region sequences, respectively, of antibody 4518.

Another embodiment of this aspect of the invention relates to a recombinant antibody composition comprising at least first and second recombinant antibodies, wherein the first and second antibodies are:

antibodies 4380 and 4519, or humanized variants thereof;

an antibody comprising the heavy chain CDR3 sequence of antibody 4380, and an antibody comprising the heavy chain CDR3 sequence of antibody 4519;

an antibody comprising the heavy and light chain CDR3 sequences of antibody 4380, and an antibody comprising the heavy and light chain CDR3 sequences of antibody 4519;

an antibody comprising the heavy and light chain CDR1, CDR2 and CDR3 sequences of antibody 4380, and an antibody comprising the heavy and light chain CDR1, CDR2 and CDR3 sequences of antibody 4519;

an antibody comprising the heavy and light chain variable region sequences of antibody 4380, and an antibody comprising the heavy and light chain variable region sequences of antibody 4519; or an antibody comprising heavy and light chain variable region sequences each having at least 80%, 85%, 90% or 95% sequence identity with the heavy and light chain variable region sequences, respectively, of antibody 4380, and an antibody comprising heavy and light chain variable region sequences each having at least 80%, 85%, 90% or 95% sequence identity with the heavy and light chain variable region sequences, respectively, of antibody 4519.

Another embodiment of this aspect of the invention relates to a recombinant antibody composition comprising at least first and second recombinant antibodies, wherein the first and second antibodies are:

antibodies 4382 and 4384, or humanized variants thereof;

an antibody comprising the heavy chain CDR3 sequence of antibody 4382, and an antibody comprising the heavy chain CDR3 sequence of antibody 4384;

an antibody comprising the heavy and light chain CDR3 sequences of antibody 4382, and an antibody comprising the heavy and light chain CDR3 sequences of antibody 4384;

an antibody comprising the heavy and light chain CDR1, CDR2 and CDR3 sequences of antibody 4382, and an antibody comprising the heavy and light chain CDR1, CDR2 and CDR3 sequences of antibody 4384;

an antibody comprising the heavy and light chain variable region sequences of antibody 4382, and an antibody comprising the heavy and light chain variable region sequences of antibody 4384; or an antibody comprising heavy and light chain variable region sequences each having at least 80%, 85%, 90% or 95% sequence identity with the heavy and light chain variable region sequences, respectively, of antibody 4382, and an antibody comprising heavy and light chain variable region sequences each having at least 80%, 85%, 90% or 95% sequence identity with the heavy and light chain variable region sequences, respectively, of antibody 4384.

Another embodiment of this aspect of the invention relates to a recombinant antibody composition comprising at least first and second recombinant antibodies, wherein the first and second antibodies are:

antibodies 4382 and 4385, or humanized variants thereof;

an antibody comprising the heavy chain CDR3 sequence of antibody 4382, and an antibody comprising the heavy chain CDR3 sequence of antibody 4385;

an antibody comprising the heavy and light chain CDR3 sequences of antibody 4382, and an antibody comprising the heavy and light chain CDR3 sequences of antibody 4385;

an antibody comprising the heavy and light chain CDR1, CDR2 and CDR3 sequences of antibody 4382, and an antibody comprising the heavy and light chain CDR1, CDR2 and CDR3 sequences of antibody 4385;

an antibody comprising the heavy, and light chain variable region sequences of antibody 4382, and an antibody comprising the heavy and light chain variable region sequences of antibody 4385; or an antibody comprising heavy and light chain variable region sequences each having at least 80%, 85%, 90% or 95% sequence identity with the heavy and light chain variable region sequences, respectively, of antibody 4382, and an antibody comprising heavy and light chain variable region sequences each having at least 80%, 85%, 90% or 95% sequence identity with the heavy and light chain variable region sequences, respectively, of antibody 4385.

A further embodiment of this aspect of the invention relates to compositions based on antibodies 4382 and 4385, and comprising at least one additional antibody. One such embodiment relates to a recombinant antibody composition comprising first, second and third recombinant antibodies, wherein the first, second and third antibodies are:

antibodies 4382, 4385 and 4518, or humanized variants thereof;

an antibody comprising the heavy chain CDR3 sequence of antibody 4382, an antibody comprising the heavy chain CDR3 sequence of antibody 4385, and an antibody comprising the heavy chain CDR3 sequence of antibody 4518;

an antibody comprising the heavy and light chain CDR3 sequences of antibody 4382, an antibody comprising the heavy and light chain CDR3 sequences of antibody 4385, and an antibody comprising the heavy and light chain CDR3 sequences of antibody 4518;

an antibody comprising the heavy and light chain CDR1, CDR2 and CDR3 sequences of antibody 4382, an antibody comprising the heavy and light chain CDR1, CDR2 and CDR3 sequences of antibody 4385, and an antibody comprising the heavy and light chain CDR1, CDR2 and CDR3 sequences of antibody 4518;

an antibody comprising the heavy and light chain variable region sequences of antibody 4382, an antibody comprising the heavy and light chain variable region sequences of antibody 4385, and an antibody comprising the heavy and light chain variable region sequences of antibody 4518;

an antibody comprising heavy and light chain variable region sequences each having at least 80%, 85%, 90% or 95% sequence identity with the heavy and light chain variable region sequences, respectively, of antibody 4382, an antibody comprising heavy and light chain variable region sequences each having at least 80%, 85%, 90% or 95% sequence identity with the heavy and light chain variable region sequences, respectively, of antibody 4385, and an antibody comprising heavy and light chain variable region sequences each having at least 80%, 85%, 90% or 95% sequence identity with the heavy and light chain variable region sequences, respectively, of antibody 4518.

Another embodiment of this aspect of the invention relates to a recombinant antibody composition comprising at least first and second recombinant antibodies, wherein the first and second antibodies are:

antibodies 4382 and 4386, or humanized variants thereof;

an antibody comprising the heavy chain CDR3 sequence of antibody 4382, and an antibody comprising the heavy chain CDR3 sequence of antibody 4386;

an antibody comprising the heavy and light chain CDR3 sequences of antibody 4382, and an antibody comprising the heavy and light chain CDR3 sequences of antibody 4386;

an antibody comprising the heavy and light chain CDR1, CDR2 and CDR3 sequences of antibody 4382, and an antibody comprising the heavy and light chain CDR1, CDR2 and CDR3 sequences of antibody 4386;

an antibody comprising the heavy and light chain variable region sequences of antibody 4382, and an antibody comprising the heavy and light chain variable region sequences of antibody 4386; or an antibody comprising heavy and light chain variable region sequences each having at least 80%, 85%, 90% or 95% sequence identity with the heavy and light chain variable region sequences, respectively, of antibody 4382, and an antibody comprising heavy and light chain variable region sequences each having at least 80%, 85%, 90% or 95% sequence identity with the heavy and light chain variable region sequences, respectively, of antibody 4386.

Another embodiment of this aspect of the invention relates to a recombinant antibody composition comprising at least first and second recombinant antibodies, wherein the first and second antibodies are:

antibodies 4382 and 4387, or humanized variants thereof;

an antibody comprising the heavy chain CDR3 sequence of antibody 4382, and an antibody comprising the heavy chain CDR3 sequence of antibody 4387;

an antibody comprising the heavy and light chain CDR3 sequences of antibody 4382, and an antibody comprising the heavy and light chain CDR3 sequences of antibody 4387;

an antibody comprising the heavy and light chain CDR1, CDR2 and CDR3 sequences of antibody 4382, and an antibody comprising the heavy and light chain CDR1, CDR2 and CDR3 sequences of antibody 4387;

an antibody comprising the heavy and light chain variable region sequences of antibody 4382, and an antibody comprising the heavy and light chain variable region sequences of antibody 4387; or an antibody comprising heavy and light chain variable region sequences each having at least 80%, 85%, 90% or 95% sequence identity with the heavy and light chain variable region sequences, respectively, of antibody 4382, and an antibody comprising heavy and light chain variable region sequences each having at least 80%, 85%, 90% or 95% sequence identity with the heavy and light chain variable region sequences, respectively, of antibody 4387.

A further embodiment of this aspect of the invention relates to compositions based on antibodies 4382 and 4387, and comprising at least one additional antibody. One such embodiment relates to a recombinant antibody composition comprising first, second and third recombinant antibodies, wherein the first, second and third antibodies are:

antibodies 4382, 4387 and 4517, or humanized variants thereof;

an antibody comprising the heavy chain CDR3 sequence of antibody 4382, an antibody comprising the heavy chain CDR3 sequence of antibody 4387, and an antibody comprising the heavy chain CDR3 sequence of antibody 4517;

an antibody comprising the heavy and light chain CDR3 sequences of antibody 4382, an antibody comprising the heavy and light chain CDR3 sequences of antibody 4387, and an antibody comprising the heavy and light chain CDR3 sequences of antibody 4517;

an antibody comprising the heavy and light chain CDR1, CDR2 and CDR3 sequences of antibody 4382, an antibody comprising the heavy and light chain CDR1, CDR2 and CDR3 sequences of antibody 4387, and an antibody comprising the heavy and light chain CDR1, CDR2 and CDR3 sequences of antibody 4517;

an antibody comprising the heavy and light chain variable region sequences of antibody 4382, an antibody comprising the heavy and light chain variable region sequences of antibody 4387, and an antibody comprising the heavy and light chain variable region sequences of antibody 4517; or an antibody comprising heavy and light chain variable region sequences each having at least 80%, 85%, 90% or 95% sequence identity with the heavy and light chain variable region sequences, respectively, of antibody 4382, an antibody comprising heavy and light chain variable region sequences each having at least 80%, 85%, 90% or 95% sequence identity with the heavy and light chain variable region sequences, respectively, of antibody 4387, and an antibody comprising heavy and light chain variable region sequences each having at least 80%, 85%, 90% or 95% sequence identity with the heavy and light chain variable region sequences, respectively, of antibody 4517.

Another embodiment of this aspect of the invention relates to a recombinant antibody composition comprising at least first and second recombinant antibodies, wherein the first and second antibodies are:

antibodies 4382 and 4517, or humanized variants thereof;

an antibody comprising the heavy chain CDR3 sequence of antibody 4382, and an antibody comprising the heavy chain CDR3 sequence of antibody 4517;

an antibody comprising the heavy and light chain CDR3 sequences of antibody 4382, and an antibody comprising the heavy and light chain CDR3 sequences of antibody 4517;

an antibody comprising the heavy and light chain CDR1, CDR2 and CDR3 sequences of antibody 4382, and an antibody comprising the heavy and light chain CDR1, CDR2 and CDR3 sequences of antibody 4517;

an antibody comprising the heavy and light chain variable region sequences of antibody 4382, and an antibody comprising the heavy and light chain variable region sequences of antibody 4517; or an antibody comprising heavy and light chain variable region sequences each having at least 80%, 85%, 90% or 95% sequence identity with the heavy and light chain variable region sequences, respectively, of antibody 4382, and an antibody comprising heavy and light chain variable region sequences each having at least 80%, 85%, 90% or 95% sequence identity with the heavy and light chain variable region sequences, respectively, of antibody 4517.

Another embodiment of this aspect of the invention relates to a recombinant antibody composition comprising at least first and second recombinant antibodies, wherein the first and second antibodies are:

antibodies 4382 and 4518, or humanized variants thereof;

an antibody comprising the heavy chain CDR3 sequence of antibody 4382, and an antibody comprising the heavy chain CDR3 sequence of antibody 4518;

an antibody comprising the heavy and light chain CDR3 sequences of antibody 4382, and an antibody comprising the heavy and light chain CDR3 sequences of antibody 4518;

an antibody comprising the heavy and light chain CDR1, CDR2 and CDR3 sequences of antibody 4382, and an antibody comprising the heavy and light chain CDR1, CDR2 and CDR3 sequences of antibody 4518;

an antibody comprising the heavy and light chain variable region sequences of antibody 4382, and an antibody comprising the heavy and light chain variable region sequences of antibody 4518; or an antibody comprising heavy and light chain variable region sequences each having at least 80%, 85%, 90% or 95% sequence identity with the heavy and light chain variable region sequences, respectively, of antibody 4382, and an antibody comprising heavy and light chain variable region sequences each having at least 80%, 85%, 90% or 95% sequence identity with the heavy and light chain variable region sequences, respectively, of antibody 4518.

Another embodiment of this aspect of the invention relates to a recombinant antibody composition comprising at least first and second recombinant antibodies, wherein the first and second antibodies are:

antibodies 4383 and 4384, or humanized variants thereof;

an antibody comprising the heavy chain CDR3 sequence of antibody 4383, and an antibody comprising the heavy chain CDR3 sequence of antibody 4384;

an antibody comprising the heavy and light chain CDR3 sequences of antibody 4383, and an antibody comprising the heavy and light chain CDR3 sequences of antibody 4384;

an antibody comprising the heavy and light chain CDR1, CDR2 and CDR3 sequences of antibody 4383, and an antibody comprising the heavy and light chain CDR1, CDR2 and CDR3 sequences of antibody 4384;

an antibody comprising the heavy and light chain variable region sequences of antibody 4383, and an antibody comprising the heavy and light chain variable region sequences of antibody 4384; or an antibody comprising heavy and light chain variable region sequences each having at least 80%, 85%, 90% or 95% sequence identity with the heavy and light chain variable region sequences, respectively, of antibody 4383, and an antibody comprising heavy and light chain variable region sequences each having at least 80%, 85%, 90% or 95% sequence identity with the heavy and light chain variable region sequences, respectively, of antibody 4384.

Another embodiment of this aspect of the invention relates to a recombinant antibody composition comprising at least first and second recombinant antibodies, wherein the first and second antibodies are:

antibodies 4383 and 4385, or humanized variants thereof;

an antibody comprising the heavy chain CDR3 sequence of antibody 4383, and an antibody comprising the heavy chain CDR3 sequence of antibody 4385;

an antibody comprising the heavy and light chain CDR3 sequences of antibody 4383, and an antibody comprising the heavy and light chain CDR3 sequences of antibody 4385;

an antibody comprising the heavy and light chain CDR1, CDR2 and CDR3 sequences of antibody 4383, and an antibody comprising the heavy and light chain CDR1, CDR2 and CDR3 sequences of antibody 4385;

an antibody comprising the heavy and light chain variable region sequences of antibody 4383, and an antibody comprising the heavy and light chain variable region sequences of antibody 4385; or an antibody comprising heavy and light chain variable region sequences each having at least 80%, 85%, 90% or 95% sequence identity with the heavy and light chain variable region sequences, respectively, of antibody 4383, and an antibody comprising heavy and light chain variable region sequences each having at least 80%, 85%, 90% or 95% sequence identity with the heavy and light chain variable region sequences, respectively, of antibody 4385.

Another embodiment of this aspect of the invention relates to a recombinant antibody composition comprising at least first and second recombinant antibodies, wherein the first and second antibodies are:

antibodies 4383 and 4386, or humanized variants thereof;

an antibody comprising the heavy chain CDR3 sequence of antibody 4383, and an antibody comprising the heavy chain CDR3 sequence of antibody 4386;

an antibody comprising the heavy and light chain CDR3 sequences of antibody 4383, and an antibody comprising the heavy and light chain CDR3 sequences of antibody 4386;

an antibody comprising the heavy and light chain CDR1, CDR2 and CDR3 sequences of antibody 4383, and an antibody comprising the heavy and light chain CDR1, CDR2 and CDR3 sequences of antibody 4386;

an antibody comprising the heavy and light chain variable region sequences of antibody 4383, and an antibody comprising the heavy and light chain variable region sequences of antibody 4386; or an antibody comprising heavy and light chain variable region sequences each having at least 80%, 85%, 90% or 95% sequence identity with the heavy and light chain variable region sequences, respectively, of antibody 4383, and an antibody comprising heavy and light chain variable region sequences each having at least 80%, 85%, 90% or 95% sequence identity with the heavy and light chain variable region sequences, respectively, of antibody 4386.

Another embodiment of this aspect of the invention relates to a recombinant antibody composition comprising at least first and second recombinant antibodies, wherein the first and second antibodies are:

antibodies 4383 and 4517, or humanized variants thereof;

an antibody comprising the heavy chain CDR3 sequence of antibody 4383, and an antibody comprising the heavy chain CDR3 sequence of antibody 4517;

an antibody comprising the heavy and light chain CDR3 sequences of antibody 4383, and an antibody comprising the heavy and light chain CDR3 sequences of antibody 4517;

an antibody comprising the heavy and light chain CDR1, CDR2 and CDR3 sequences of antibody 4383, and an antibody comprising the heavy and light chain CDR1, CDR2 and CDR3 sequences of antibody 4517;

an antibody comprising the heavy and light chain variable region sequences of antibody 4383, and an antibody comprising the heavy and light chain variable region sequences of antibody 4517; or an antibody comprising heavy and light chain variable region sequences each having at least 80%, 85%, 90% or 95% sequence identity with the heavy and light chain variable region sequences, respectively, of antibody 4383, and an antibody comprising heavy and light chain variable region sequences each having at least 80%, 85%, 90% or 95% sequence identity with the heavy and light chain variable region sequences, respectively, of antibody 4517.

Another embodiment of this aspect of the invention relates to a recombinant antibody composition comprising at least first and second recombinant antibodies, wherein the first and second antibodies are:

antibodies 4383 and 4518, or humanized variants thereof;

an antibody comprising the heavy chain CDR3 sequence of antibody 4383, and an antibody comprising the heavy chain CDR3 sequence of antibody 4518;

an antibody comprising the heavy and light chain CDR3 sequences of antibody 4383, and an antibody comprising the heavy and light chain CDR3 sequences of antibody 4518;

an antibody comprising the heavy and light chain CDR1, CDR2 and CDR3 sequences of antibody 4383, and an antibody comprising the heavy and light chain CDR1, CDR2 and CDR3 sequences of antibody 4518;

an antibody comprising the heavy and light chain variable region sequences of antibody 4383, and an antibody comprising the heavy and light chain variable region sequences of antibody 4518; or an antibody comprising heavy and light chain variable region sequences each having at least 80%, 85%, 90% or 95% sequence identity with the heavy and light chain variable region sequences, respectively, of antibody 4383, and an antibody comprising heavy and light chain variable region sequences each having at least 80%, 85%, 90% or 95% sequence identity with the heavy and light chain variable region sequences, respectively, of antibody 4518.

Another embodiment of this aspect of the invention relates to a recombinant antibody composition comprising at least first and second recombinant antibodies, wherein the first and second antibodies are:

antibodies 4383 and 4519, or humanized variants thereof;

an antibody comprising the heavy chain CDR3 sequence of antibody 4383, and an antibody comprising the heavy chain CDR3 sequence of antibody 4519;

an antibody comprising the heavy and light chain CDR3 sequences of antibody 4383, and an antibody comprising the heavy and light chain CDR3 sequences of antibody 4519;

an antibody comprising the heavy and light chain CDR1, CDR2 and CDR3 sequences of antibody 4383, and an antibody comprising the heavy and light chain CDR1, CDR2 and CDR3 sequences of antibody 4519;

an antibody comprising the heavy and light chain variable region sequences of antibody 4383, and an antibody comprising the heavy and light chain variable region sequences of antibody 4519; or an antibody comprising heavy and light chain variable region sequences each having at least 80%, 85%, 90% or 95% sequence identity with the heavy and light chain variable region sequences, respectively, of antibody 4383, and an antibody comprising heavy and light chain variable region sequences each having at least 80%, 85%, 90% or 95% sequence identity with the heavy and light chain variable region sequences, respectively, of antibody 4519.

Another embodiment of this aspect of the invention relates to a recombinant antibody composition comprising at least first and second recombinant antibodies, wherein the first and second antibodies are:

antibodies 4384 and 4385, or humanized variants thereof;

an antibody comprising the heavy chain CDR3 sequence of antibody 4384, and an antibody comprising the heavy chain CDR3 sequence of antibody 4385;

an antibody comprising the heavy and light chain CDR3 sequences of antibody 4384, and an antibody comprising the heavy and light chain CDR3 sequences of antibody 4385;

an antibody comprising the heavy and light chain CDR1, CDR2 and CDR3 sequences of antibody 4384, and an antibody comprising the heavy and light chain CDR1, CDR2 and CDR3 sequences of antibody 4385;

an antibody comprising the heavy and light chain variable region sequences of antibody 4384, and an antibody comprising the heavy and light chain variable region sequences of antibody 4385; or an antibody comprising heavy and light chain variable region sequences each having at least 80%, 85%, 90% or 95% sequence identity with the heavy and light chain variable region sequences, respectively, of antibody 4384, and an antibody comprising heavy and light chain variable region sequences each having at least 80%, 85%, 90% or 95% sequence identity with the heavy and light chain variable region sequences, respectively, of antibody 4385.

Another embodiment of this aspect of the invention relates to a recombinant antibody composition comprising at least first and second recombinant antibodies, wherein the first and second antibodies are:

antibodies 4384 and 4387, or humanized variants thereof;

an antibody comprising the heavy chain CDR3 sequence of antibody 4384, and an antibody comprising the heavy chain CDR3 sequence of antibody 4387;

an antibody comprising the heavy and light chain CDR3 sequences of antibody 4384, and an antibody comprising the heavy and light chain CDR3 sequences of antibody 4387;

an antibody comprising the heavy and light chain CDR1, CDR2 and CDR3 sequences of antibody 4384, and an antibody comprising the heavy and light chain CDR1, CDR2 and CDR3 sequences of antibody 4387;

an antibody comprising the heavy and light chain variable region sequences of antibody 4384, and an antibody comprising the heavy and light chain variable region sequences of antibody 4387; or an antibody comprising heavy and light chain variable region sequences each having at least 80%, 85%, 90% or 95% sequence identity with the heavy and light chain variable region sequences, respectively, of antibody 4384, and an antibody comprising heavy and light chain variable region sequences each having at least 80%, 85%, 90% or 95% sequence identity with the heavy and light chain variable region sequences, respectively, of antibody 4387.

Another embodiment of this aspect of the invention relates to a recombinant antibody composition comprising at least first and second recombinant antibodies, wherein the first and second antibodies are:

antibodies 4384 and 4517, or humanized variants thereof;

an antibody comprising the heavy chain CDR3 sequence of antibody 4384, and an antibody comprising the heavy chain CDR3 sequence of antibody 4517;

an antibody comprising the heavy and light chain CDR3 sequences of antibody 4384, and an antibody comprising the heavy and light chain CDR3 sequences of antibody 4517;

an antibody comprising the heavy and light chain CDR1, CDR2 and CDR3 sequences of antibody 4384, and an antibody comprising the heavy and light chain CDR1, CDR2 and CDR3 sequences of antibody 4517;

an antibody comprising the heavy and light chain variable region sequences of antibody 4384, and an antibody comprising the heavy and light chain variable region sequences of antibody 4517; or an antibody comprising heavy and light chain variable region sequences each having at least 80%, 85%, 90% or 95% sequence identity with the heavy and light chain variable region sequences, respectively, of antibody 4384, and an antibody comprising heavy and light chain variable region sequences each having at least 80%, 85%, 90% or 95% sequence identity with the heavy and light chain variable region sequences, respectively, of antibody 4517.

Another embodiment of this aspect of the invention relates to a recombinant antibody composition comprising at least first and second recombinant antibodies, wherein the first and second antibodies are:

antibodies 4384 and 4519, or humanized variants thereof;

an antibody comprising the heavy chain CDR3 sequence of antibody 4384, and an antibody comprising the heavy chain CDR3 sequence of antibody 4519;

an antibody comprising the heavy and light chain CDR3 sequences of antibody 4384, and an antibody comprising the heavy and light chain CDR3 sequences of antibody 4519;

an antibody comprising the heavy and light chain CDR1, CDR2 and CDR3 sequences of antibody 4384, and an antibody comprising the heavy and light chain CDR1, CDR2 and CDR3 sequences of antibody 4519;

an antibody comprising the heavy and light chain variable region sequences of antibody 4384, and an antibody comprising the heavy and light chain variable region sequences of antibody 4519; or an antibody comprising heavy and light chain variable region sequences each having at least 80%, 85%, 90% or 95% sequence identity with the heavy and light chain variable region sequences, respectively, of antibody 4384, and an antibody comprising heavy and light chain variable region sequences each having at least 80%, 85%, 90% or 95% sequence identity with the heavy and light chain variable region sequences, respectively, of antibody 4519.

Another embodiment of this aspect of the invention relates to a recombinant antibody composition comprising at least first and second recombinant antibodies, wherein the first and second antibodies are:

antibodies 4385 and 4386, or humanized variants thereof;

an antibody comprising the heavy chain CDR3 sequence of antibody 4385, and an antibody comprising the heavy chain CDR3 sequence of antibody 4386;

an antibody comprising the heavy and light chain CDR3 sequences of antibody 4385, and an antibody comprising the heavy and light chain CDR3 sequences of antibody 4386;

an antibody comprising the heavy and light chain CDR1, CDR2 and CDR3 sequences of antibody 4385, and an antibody comprising the heavy and light chain CDR1, CDR2 and CDR3 sequences of antibody 4386;

an antibody comprising the heavy and light chain variable region sequences of antibody 4385, and an antibody comprising the heavy and light chain variable region sequences of antibody 4386; or an antibody comprising heavy and light chain variable region sequences each having at least 80%, 85%, 90% or 95% sequence identity with the heavy and light chain variable region sequences, respectively, of antibody 4385, and an antibody comprising heavy and light chain variable region sequences each having at least 80%, 85%, 90% or 95% sequence identity with the heavy and light chain variable region sequences, respectively, of antibody 4386.

Another embodiment of this aspect of the invention relates to a recombinant antibody composition comprising at least first and second recombinant antibodies, wherein the first and second antibodies are:

antibodies 4385 and 4517, or humanized variants thereof;

an antibody comprising the heavy chain CDR3 sequence of antibody 4385, and an antibody comprising the heavy chain CDR3 sequence of antibody 4517;

an antibody comprising the heavy and light chain CDR3 sequences of antibody 4385, and an antibody comprising the heavy and light chain CDR3 sequences of antibody 4517;

an antibody comprising the heavy and light chain CDR1, CDR2 and CDR3 sequences of antibody 4385, and an antibody comprising the heavy and light chain CDR1, CDR2 and CDR3 sequences of antibody 4517;

an antibody comprising the heavy and light chain variable region sequences of antibody 4385, and an antibody comprising the heavy and light chain variable region sequences of antibody 4517; or an antibody comprising heavy and light chain variable region sequences each having at least 80%, 85%, 90% or 95% sequence identity with the heavy and light chain variable region sequences, respectively, of antibody 4385, and an antibody comprising heavy and light chain variable region sequences each having at least 80%, 85%, 90% or 95% sequence identity with the heavy and light chain variable region sequences, respectively, of antibody 4517.

Another embodiment of this aspect of the invention relates to a recombinant antibody composition comprising at least first and second recombinant antibodies, wherein the first and second antibodies are:

antibodies 4385 and 4518, or humanized variants thereof;

an antibody comprising the heavy chain CDR3 sequence of antibody 4385, and an antibody comprising the heavy chain CDR3 sequence of antibody 4518;

an antibody comprising the heavy and light chain CDR3 sequences of antibody 4385, and an antibody comprising the heavy and light chain CDR3 sequences of antibody 4518;

an antibody comprising the heavy and light chain CDR1, CDR2 and CDR3 sequences of antibody 4385, and an antibody comprising the heavy and light chain CDR1, CDR2 and CDR3 sequences of antibody 4518;

an antibody comprising the heavy and light chain variable region sequences of antibody 4385, and an antibody comprising the heavy and light chain variable region sequences of antibody 4518; or an antibody comprising heavy and light chain variable region sequences each having at least 80%, 85%, 90% or 95% sequence identity with the heavy and light chain variable region sequences, respectively, of antibody 4385, and an antibody comprising heavy and light chain variable region sequences each having at least 80%, 85%, 90% or 95% sequence identity with the heavy and light chain variable region sequences, respectively, of antibody 4518.

Another embodiment of this aspect of the invention relates to a recombinant antibody composition comprising at least first and second recombinant antibodies, wherein the first and second antibodies are:

antibodies 4385 and 4519, or humanized variants thereof;

an antibody comprising the heavy chain CDR3 sequence of antibody 4385, and an antibody comprising the heavy chain CDR3 sequence of antibody 4519;

an antibody comprising the heavy and light chain CDR3 sequences of antibody 4385, and an antibody comprising the heavy and light chain CDR3 sequences of antibody 4519;

an antibody comprising the heavy and light chain CDR1, CDR2 and CDR3 sequences of antibody 4385, and an antibody comprising the heavy and light chain CDR1, CDR2 and CDR3 sequences of antibody 4519;

an antibody comprising the heavy and light chain variable region sequences of antibody 4385, and an antibody comprising the heavy and light chain variable region sequences of antibody 4519; or an antibody comprising heavy and light chain variable region sequences each having at least 80%, 85%, 90% or 95% sequence identity with the heavy and light chain variable region sequences, respectively, of antibody 4385, and an antibody comprising heavy and light chain variable region sequences each having at least 80%, 85%, 90% or 95% sequence identity with the heavy and light chain variable region sequences, respectively, of antibody 4519.

Another embodiment of this aspect of the invention relates to a recombinant antibody composition comprising at least first and second recombinant antibodies, wherein the first and second antibodies are:

antibodies 4386 and 4387, or humanized variants thereof;

an antibody comprising the heavy chain CDR3 sequence of antibody 4386, and an antibody comprising the heavy chain CDR3 sequence of antibody 4387;

an antibody comprising the heavy and light chain CDR3 sequences of antibody 4386, and an antibody comprising the heavy and light chain CDR3 sequences of antibody 4387;

an antibody comprising the heavy and light chain CDR1, CDR2 and CDR3 sequences of antibody 4386, and an antibody comprising the heavy and light chain CDR1, CDR2 and CDR3 sequences of antibody 4387;

an antibody comprising the heavy and light chain variable region sequences of antibody 4386, and an antibody comprising the heavy and light chain variable region sequences of antibody 4387; or an antibody comprising heavy and light chain variable region sequences each having at least 80%, 85%, 90% or 95% sequence identity with the heavy and light chain variable region sequences, respectively, of antibody 4386, and an antibody comprising heavy and light chain variable region sequences each having at least 80%, 85%, 90% or 95% sequence identity with the heavy and light chain variable region sequences, respectively, of antibody 4387.

Another embodiment of this aspect of the invention relates to a recombinant antibody composition comprising at least first and second recombinant antibodies, wherein the first and second antibodies are:

antibodies 4386 and 4517, or humanized variants thereof;

an antibody comprising the heavy chain CDR3 sequence of antibody 4386, and an antibody comprising the heavy chain CDR3 sequence of antibody 4517;

an antibody comprising the heavy and light chain CDR3 sequences of antibody 4386, and an antibody comprising the heavy and light chain CDR3 sequences of antibody 4517;

an antibody comprising the heavy and light chain CDR1, CDR2 and CDR3 sequences of antibody 4386, and an antibody comprising the heavy and light chain CDR1, CDR2 and CDR3 sequences of antibody 4517;

an antibody comprising the heavy and light chain variable region sequences of antibody 4386, and an antibody comprising the heavy and light chain variable region sequences of antibody 4517; or an antibody comprising heavy and light chain variable region sequences each having at least 80%, 85%, 90% or 95% sequence identity with the heavy and light chain variable region sequences, respectively, of antibody 4386, and an antibody comprising heavy and light chain variable region sequences each having at least 80%, 85%, 90% or 95% sequence identity with the heavy and light chain variable region sequences, respectively, of antibody 4517.

Another embodiment of this aspect of the invention relates to a recombinant antibody composition comprising at least first and second recombinant antibodies, wherein the first and second antibodies are:

antibodies 4386 and 4518, or humanized variants thereof;

an antibody comprising the heavy chain CDR3 sequence of antibody 4386, and an antibody comprising the heavy chain CDR3 sequence of antibody 4518;

an antibody comprising the heavy and light chain CDR3 sequences of antibody 4386, and an antibody comprising the heavy and light chain CDR3 sequences of antibody 4518;

an antibody comprising the heavy and light chain CDR1, CDR2 and CDR3 sequences of antibody 4386, and an antibody comprising the heavy and light chain CDR1, CDR2 and CDR3 sequences of antibody 4518;

an antibody comprising the heavy and light chain variable region sequences of antibody 4386, and an antibody comprising the heavy and light chain variable region sequences of antibody 4518; or an antibody comprising heavy and light chain variable region sequences each having at least 80%, 85%, 90% or 95% sequence identity with the heavy and light chain variable region sequences, respectively, of antibody 4386, and an antibody comprising heavy and light chain variable region sequences each having at least 80%, 85%, 90% or 95% sequence identity with the heavy and light chain variable region sequences, respectively, of antibody 4518.

Another embodiment of this aspect of the invention relates to a recombinant antibody composition comprising at least first and second recombinant antibodies, wherein the first and second antibodies are:

antibodies 4386 and 4519, or humanized variants thereof;

an antibody comprising the heavy chain CDR3 sequence of antibody 4386, and an antibody comprising the heavy chain CDR3 sequence of antibody 4519;

an antibody comprising the heavy and light chain CDR3 sequences of antibody 4386, and an antibody comprising the heavy and light chain CDR3 sequences of antibody 4519;

an antibody comprising the heavy and light chain CDR1, CDR2 and CDR3 sequences of antibody 4386, and an antibody comprising the heavy and light chain CDR1, CDR2 and CDR3 sequences of antibody 4519;

an antibody comprising the heavy and light chain variable region sequences of antibody 4386, and an antibody comprising the heavy and light chain variable region sequences of antibody 4519; or an antibody comprising heavy and light chain variable region sequences each having at least 80%; 85%, 90% or 95% sequence identity with the heavy and light chain variable region sequences, respectively, of antibody 4386, and an antibody comprising heavy and light chain variable region sequences each having at least 80%, 85%, 90% or 95% sequence identity with the heavy and light chain variable region sequences, respectively, of antibody 4519.

Another embodiment of this aspect of the invention relates to a recombinant antibody composition comprising at least first and second recombinant antibodies, wherein the first and second antibodies are:

antibodies 4387 and 4517, or humanized variants thereof;

an antibody comprising the heavy chain CDR3 sequence of antibody 4387, and an antibody comprising the heavy chain CDR3 sequence of antibody 4517;

an antibody comprising the heavy and light chain CDR3 sequences of antibody 4387, and an antibody comprising the heavy and light chain CDR3 sequences of antibody 4517;

an antibody comprising the heavy and light chain CDR1, CDR2 and CDR3 sequences of antibody 4387, and an antibody comprising the heavy and light chain CDR1, CDR2 and CDR3 sequences of antibody 4517;

an antibody comprising the heavy and light chain variable region sequences of antibody 4387, and an antibody comprising the heavy and light chain variable region sequences of antibody 4517; or an antibody comprising heavy and light chain variable region sequences each having at least 80%, 85%, 90% or 95% sequence identity with the heavy and light chain variable region sequences, respectively, of antibody 4387, and an antibody comprising heavy and light chain variable region sequences each having at least 80%, 85%, 90% or 95% sequence identity with the heavy and light chain variable region sequences, respectively, of antibody 4517.

Another embodiment of this aspect of the invention relates to a recombinant antibody composition comprising at least first and second recombinant antibodies, wherein the first and second antibodies are:

antibodies 4387 and 4518, or humanized variants thereof;

an antibody comprising the heavy chain CDR3 sequence of antibody 4387, and an antibody comprising the heavy chain CDR3 sequence of antibody 4518;

an antibody comprising the heavy and light chain CDR3 sequences of antibody 4387, and an antibody comprising the heavy and light chain CDR3 sequences of antibody 4518;

an antibody comprising the heavy and light chain CDR1, CDR2 and CDR3 sequences of antibody 4387, and an antibody comprising the heavy and light chain CDR1, CDR2 and CDR3 sequences of antibody 4518;

an antibody comprising the heavy and light chain variable region sequences of antibody 4387, and an antibody comprising the heavy and light chain variable region sequences of antibody 4518; or an antibody comprising heavy and light chain variable region sequences each having at least 80%, 85%, 90% or 95% sequence identity with the heavy and light chain variable region sequences, respectively, of antibody 4387, and an antibody comprising heavy and light chain variable region sequences each having at least 80%, 85%, 90% or 95% sequence identity with the heavy and light chain variable region sequences, respectively, of antibody 4518.

Another embodiment of this aspect of the invention relates to a recombinant antibody composition comprising at least first and second recombinant antibodies, wherein the first and second antibodies are:

antibodies 4387 and 4519, or humanized variants thereof;

an antibody comprising the heavy chain CDR3 sequence of antibody 4387, and an antibody comprising the heavy chain CDR3 sequence of antibody 4519;

an antibody comprising the heavy and light chain CDR3 sequences of antibody 4387, and an antibody comprising the heavy and light chain CDR3 sequences of antibody 4519;

an antibody comprising the heavy and light chain CDR1, CDR2 and CDR3 sequences of antibody 4387, and an antibody comprising the heavy and light chain CDR1, CDR2 and CDR3 sequences of antibody 4519;

an antibody comprising the heavy and light chain variable region sequences of antibody 4387, and an antibody comprising the heavy and light chain variable region sequences of antibody 4519; or an antibody comprising heavy and light chain variable region sequences each having at least 80%, 85%, 90% or 95% sequence identity with the heavy and light chain variable region sequences, respectively, of antibody 4387, and an antibody comprising heavy and light chain variable region sequences each having at least 80%, 85%, 90% or 95% sequence identity with the heavy and light chain variable region sequences, respectively, of antibody 4519.

Another embodiment of this aspect of the invention relates to a recombinant antibody composition comprising at least first and second recombinant antibodies, wherein the first and second antibodies are:

antibodies 4517 and 4519, or humanized variants thereof;

an antibody comprising the heavy chain CDR3 sequence of antibody 4517, and an antibody comprising the heavy chain CDR3 sequence of antibody 4519;

an antibody comprising the heavy and light chain CDR3 sequences of antibody 4517, and an antibody comprising the heavy and light chain CDR3 sequences of antibody 4519;

an antibody comprising the heavy and light chain CDR1, CDR2 and CDR3 sequences of antibody 4517, and an antibody comprising the heavy and light chain CDR1, CDR2 and CDR3 sequences of antibody 4519;

an antibody comprising the heavy and light chain variable region sequences of antibody 4517, and an antibody comprising the heavy and light chain variable region sequences of antibody 4519; or an antibody comprising heavy and light chain variable region sequences each having at least 80%, 85%, 90% or 95% sequence identity with the heavy and light chain variable region sequences, respectively, of antibody 4517, and an antibody comprising heavy and light chain variable region sequences each having at least 80%, 85%, 90% or 95% sequence identity with the heavy and light chain variable region sequences, respectively, of antibody 4519.

Another embodiment of this aspect of the invention relates to a recombinant antibody composition comprising at least first and second recombinant antibodies, wherein the first and second antibodies are:

antibodies 4518 and 4519, or humanized variants thereof;

an antibody comprising the heavy chain CDR3 sequence of antibody 4518, and an antibody comprising the heavy chain CDR3 sequence of antibody 4519;

an antibody comprising the heavy and light chain CDR3 sequences of antibody 4518, and an antibody comprising the heavy and light chain CDR3 sequences of antibody 4519;

an antibody comprising the heavy and light chain CDR1, CDR2 and CDR3 sequences of antibody 4518, and an antibody comprising the heavy and light chain CDR1, CDR2 and CDR3 sequences of antibody 4519;

an antibody comprising the heavy and light chain variable region sequences of antibody 4518, and an antibody comprising the heavy and light chain variable region sequences of antibody 4519; or an antibody comprising heavy and light chain variable region sequences each having at least 80%, 85%, 90% or 95% sequence identity with the heavy and light chain variable region sequences, respectively, of antibody 4518, and an antibody comprising heavy and light chain variable region sequences each having at least 80%, 85%, 90% or 95% sequence identity with the heavy and light chain variable region sequences, respectively, of antibody 4519.

Preferred recombinant polyclonal anti-HER2 antibody compositions according to the invention thus include those wherein the first and second antibodies, respectively, are antibodies:

4380 and 4382,
4380 and 4383,
4380 and 4384,
4380 and 4385,
4380 and 4386,
4380 and 4387,
4380 and 4517,
4380 and 4518,
4380 and 4519,
4382 and 4384,
4382 and 4385,
4382 and 4386,
4382 and 4387,
4382 and 4517,
4382 and 4518,
4383 and 4384,
4383 and 4385,
4383 and 4386,
4383 and 4517,
4383 and 4518,
4383 and 4519,
4384 and 4385,
4384 and 4387,
4384 and 4517,
4384 and 4519,
4385 and 4386,
4385 and 4517,
4385 and 4518,
4385 and 4519,
4386 and 4387,
4386 and 4517,
4386 and 4518,
4386 and 4519,
4387 and 4517,
4387 and 4518,
4387 and 4519,
4517 and 4519,
4518 and 4519;

or humanized variants thereof; or antibodies derived from the respective antibodies in each listed pair, e.g. wherein the first and second antibodies comprise the heavy chain CDR3 sequence of said antibodies, or wherein the first and second antibodies comprise the heavy chain and light chain CDR3 sequences of said antibodies, or wherein the first and second antibodies comprise the heavy chain and light chain CDR1, CDR2 and CDR3 sequences of said antibodies, e.g. the heavy chain and light chain variable region sequences of said antibodies or humanized variants thereof.

More preferred recombinant polyclonal anti-HER2 antibody compositions according to the invention are those that comprise two, three or four antibodies selected from among the following combinations:
4380 and 4382,
4380 and 4384,
4380 and 4518,
4382 and 4385,
4382 and 4518,
4383 and 4518,
4384 and 4385,
4384 and 4517,
4385 and 4518,
4380, 4382 and 4385,
4380, 4382 and 4517,
4380, 4382 and 4518,
4380, 4383 and 4384,
4380, 4384 and 4517,
4380, 4384 and 4518,
4380, 4384 and 4519,
4382, 4385 and 4518,
4382, 4387 and 4517,
4380, 4382, 4385 and 4518,
4380, 4384, 4385 and 4518;
or humanized variants thereof; or antibodies derived from the respective antibodies in each listed combination, e.g. wherein the individual antibodies comprise the heavy chain CDR3 sequence of said antibodies, or wherein the individual antibodies comprise the heavy chain and light chain CDR3 sequences of said antibodies, or wherein the individual antibodies comprise the heavy chain and light chain CDR1, CDR2 and CDR3 sequences of said antibodies, e.g. the heavy chain and light chain variable region sequences of said antibodies or humanized variants thereof.

Still more preferred recombinant polyclonal anti-HER2 antibody compositions according to the invention are those that comprise two or three antibodies selected from among the following combinations:
4382 and 4518,
4384 and 4517,
4382, 4385 and 4518,
4382, 4387 and 4517;
or humanized variants thereof; or antibodies derived from the respective antibodies in each listed combination, e.g. wherein the individual antibodies comprise the heavy chain CDR3 sequence of said antibodies, or wherein the individual antibodies comprise the heavy chain and light chain CDR3 sequences of said antibodies, or wherein the individual antibodies comprise the heavy chain and light chain CDR1, CDR2 and CDR3 sequences of said antibodies, e.g. the heavy chain and light chain variable region sequences of said antibodies or humanized variants thereof.

A further embodiment is a recombinant antibody composition comprising at least first and second recombinant anti-HER2 antibodies, wherein the first and second antibodies bind distinct epitopes of HER2, and wherein the first and second antibodies bind to the same epitopes as the respective antibodies in each composition listed above.

In a preferred aspect, the recombinant polyclonal anti-HER2 antibody composition of the invention comprises at least three anti-HER2 antibodies that bind distinct epitopes of HER2, more preferably in which binding of the first and second antibodies to HER2 results in HER2 receptor internalization, and wherein binding of the third antibody to HER2 results in inhibition of ligand-induced phosphorylation of HER3. Antibody compositions of this type are believed to function by a mechanism where two of the antibodies upon binding to HER2 on the surface of a cell are capable of generating a cross-linked antibody-receptor lattice on the cell surface, thereby contributing to an increased level of HER2 receptor internalization; and where the third antibody binds HER2 such that it blocks heterodimerization between HER2 and HER3, thereby inhibiting HER3 phosphorylation.

An example of such a recombinant polyclonal antibody composition is one wherein the first anti-HER2 antibody is 4517 or 4518, the second anti-HER2 antibody is 4380, 4385 or 4387, and the third anti-HER2 antibody is 4382, 4383 or 4519;

or humanized variants thereof; or antibodies derived from the respective antibodies, e.g. wherein the first, second and third antibodies comprise the heavy chain CDR3 sequence of said antibodies, or wherein the first, second and third antibodies comprise the heavy chain and light chain CDR3 sequences of said antibodies, or wherein the first, second and third antibodies comprise the heavy chain and light chain CDR1, CDR2 and CDR3 sequences of said antibodies, e.g. the heavy chain and light chain variable region sequences of said antibodies or humanized variants thereof.

Examples of preferred recombinant polyclonal antibody compositions of this type include compositions wherein the first and second anti-HER2 antibodies are 4518+4385 or 4517+4387, and the third anti-HER2 antibody is 4382;

or humanized variants thereof; or antibodies derived from the respective antibodies, e.g. wherein the first, second and third antibodies comprise the heavy chain CDR3 sequence of said antibodies, or wherein the first, second and third antibodies comprise the heavy chain and light chain CDR3 sequences of said antibodies, or wherein the first, second and third antibodies comprise the heavy chain and light chain CDR1, CDR2 and CDR3 sequences of said antibodies, e.g. the heavy chain and light chain variable region sequences of said antibodies or humanized variants thereof.

In a particular embodiment, the invention thus relates to an antibody composition comprising first, second and third anti-HER2 antibodies that bind distinct epitopes of HER2, wherein:
(a) the first anti-HER2 antibody comprises:
  the heavy chain CDR3 sequence (SEQ ID NO: 47) and the light chain CDR3 sequence (SEQ ID NO: 76) of antibody 4517, or
  the heavy chain CDR3 sequence (SEQ ID NO: 50) and the light chain CDR3 sequence (SEQ ID NO: 78) of antibody 4518;
(b) the second anti-HER2 antibody comprises:
  the heavy chain CDR3 sequence (SEQ ID NO: 53) and the light chain CDR3 sequence (SEQ ID NO: 80) of antibody 4380,
  the heavy chain CDR3 sequence (SEQ ID NO: 65) and the light chain CDR3 sequence (SEQ ID NO: 88) of antibody 4385, or
  the heavy chain CDR3 sequence (SEQ ID NO: 71) and the light chain CDR3 sequence (SEQ ID NO: 92) of antibody 4387; and
(c) the third anti-HER2 antibody comprises:
  the heavy chain CDR3 sequence (SEQ ID NO: 56) and the light chain CDR3 sequence (SEQ ID NO: 82) of antibody 4382,
  the heavy chain CDR3 sequence (SEQ ID NO: 59) and the light chain CDR3 sequence (SEQ ID NO: 84) of antibody 4383, or
  the heavy chain CDR3 sequence (SEQ ID NO: 74) and the light chain CDR3 sequence (SEQ ID NO: 93) of antibody 4519.

In a preferred embodiment, the antibody composition comprises first, second and third anti-HER2 antibodies that bind distinct epitopes of HER2, wherein:

(a) the first anti-HER2 antibody comprises:

CDR1, CDR2 and CDR3 of the heavy chain variable region (SEQ ID NO: 2) and CDR1, CDR2 and CDR3 of the light chain variable region (SEQ ID NO: 4) of antibody 4517, or CDR1, CDR2 and CDR3 of the heavy chain variable region (SEQ ID NO: 6) and CDR1, CDR2 and CDR3 of the light chain variable region (SEQ ID NO: 8) of antibody 4518;

(b) the second anti-HER2 antibody comprises:

CDR1, CDR2 and CDR3 of the heavy chain variable region (SEQ ID NO: 10) and CDR1, CDR2 and CDR3 of the light chain variable region (SEQ ID NO: 12) of antibody 4380, CDR1, CDR2 and CDR3 of the heavy chain variable region (SEQ ID NO: 26) and CDR1, CDR2 and CDR3 of the light chain variable region (SEQ ID NO: 28) of antibody 4385, or CDR1, CDR2 and CDR3 of the heavy chain variable region (SEQ ID NO: 34) and CDR1, CDR2 and CDR3 of the light chain variable region (SEQ ID NO: 36) of antibody 4387; and (c) the third anti-HER2 antibody comprises:

CDR1, CDR2 and CDR3 of the heavy chain variable region (SEQ ID NO: 14) and CDR1, CDR2 and CDR3 of the light chain variable region (SEQ ID NO: 16) of antibody 4382, CDR1, CDR2 and CDR3 of the heavy chain variable region (SEQ ID NO: 18) and CDR1, CDR2 and CDR3 of the light chain variable region (SEQ ID NO: 20) of antibody 4383, or CDR1, CDR2 and CDR3 of the heavy chain variable region (SEQ ID NO: 38) and CDR1, CDR2 and CDR3 of the light chain variable region (SEQ ID NO: 40) of antibody 4519.

In a specific preferred embodiment, the third anti-HER2 antibody comprises CDR1, CDR2 and CDR3 of the heavy chain variable region (SEQ ID NO: 14) and CDR1, CDR2 and CDR3 of the light chain variable region (SEQ ID NO: 16) of antibody 4382. In this case, the anti-HER2 antibody composition may e.g. be one wherein:

(a) the first anti-HER2 antibody comprises CDR1, CDR2 and CDR3 of the heavy chain variable region (SEQ ID NO: 6) and CDR1, CDR2 and CDR3 of the light chain variable region (SEQ ID NO: 8) of antibody 4518, and the second anti-HER2 antibody comprises CDR1, CDR2 and CDR3 of the heavy chain variable region (SEQ ID NO: 26) and CDR1, CDR2 and CDR3 of the light chain variable region (SEQ ID NO: 28) of antibody 4385; or (b) the first anti-HER2 antibody comprises CDR1, CDR2 and CDR3 of the heavy chain variable region (SEQ ID NO: 2) and CDR1, CDR2 and CDR3 of the light chain variable region (SEQ ID NO: 4) of antibody 4517, and the second anti-HER2 antibody comprises CDR1, CDR2 and CDR3 of the heavy chain variable region (SEQ ID NO: 34) and CDR1, CDR2 and CDR3 of the light chain variable region (SEQ ID NO: 36) of antibody 4387.

In particular, the anti-HER2 antibody composition of the invention may be one wherein:

the first anti-HER2 antibody comprises CDR1, CDR2 and CDR3 of the heavy chain variable region (SEQ ID NO: 6) and CDR1, CDR2 and CDR3 of the light chain variable region (SEQ ID NO: 8) of antibody 4518, and the second anti-HER2 antibody comprises CDR1, CDR2 and CDR3 of the heavy chain variable region (SEQ ID NO: 26) and CDR1, CDR2 and CDR3 of the light chain variable region (SEQ ID NO: 28) of antibody 4385, and the third anti-HER2 antibody comprises CDR1, CDR2 and CDR3 of the heavy chain variable region (SEQ ID NO: 14) and CDR1, CDR2 and CDR3 of the light chain variable region (SEQ ID NO: 16) of antibody 4382.

Antibody 4382 binds to domain II of HER2, which is also the case for pertuzumab, and as described in Example 9 below, both 4382 and a pertuzumab analogue were able to block ligand-induced HER3 phosphorylation. Franklin et al. (*Cancer Cell* 2004, 5(4):317-28) disclose that pertuzumab binds HER2 near the center of domain II, sterically blocking a binding pocket necessary for HER2-HER3 heterodimerization and signaling. It is therefore contemplated that, in addition to e.g. 4382 and pertuzumab, other anti-HER2 antibodies that bind to the dimerization interface in a similar manner will have a similar effect in blocking HER2-HER3 heterodimerization, and that such antibodies will be suitable for use as the third antibody in this aspect of the invention.

In experiments carried out in connection with the present invention it was found that while combinations of two or more anti-HER2 antibodies described herein are able to effectively lead to internalization and degradation of HER2, the cells in which HER2 is targeted by the antibodies have a tendency to upregulate production of HER3. It is believed that development of resistance to anti-HER2 monoclonal antibodies, e.g. trastuzumab, may be related to this upregulation of HER3, possibly by a mechanism in which the HER2-HER3 heterodimer represents a complete receptor that allows for oncogenic signaling even in the absence of HER2 homodimer signaling. Example 9 below describes antibody compositions of the invention comprising three anti-HER2 antibodies, of which two antibodies are capable of binding to HER2 so as to generate a cross-linked antibody-receptor lattice that results in HER2 internalization and degradation, and a third antibody binds HER2 such that HER2-HER3 heterodimerization is blocked, thereby preventing HER3 phosphorylation and HER3-mediated signaling. It is contemplated that these and similar anti-HER2 antibody compositions, i.e. containing a mixture of at least three anti-HER2 antibodies of which two antibodies result in internalization and degradation of HER2 and a third antibody blocks HER2-HER3 heterodimerization, may be highly advantageous in terms of blocking HER family phosphorylation and signaling. In particular, it is contemplated that compositions of this type may be able to provide a significant reduction in development of tumor cell resistance to anti-HER2 antibodies. Anti-HER2 antibody compositions of this type may thus be useful for both prevention and reduction of resistance to anti-HER2 antibody treatment as well as for treatment of tumors that have already become resistant to treatment with a monoclonal anti-HER2 antibody such as trastuzumab.

A further aspect of the invention thus relates to a method for inhibiting growth of tumor cells that are resistant or partially resistant to treatment with an anti-HER2 antibody, the method comprising contacting the cells with a recombinant polyclonal anti-HER2 antibody composition as defined above comprising two anti-HER2 antibodies that are capable of generating a cross-linked antibody-receptor lattice on the cell surface, thereby resulting in HER2 internalization, and a third antibody that binds HER2 such that it blocks heterodimerization between HER2 and HER3, thereby inhibiting ligand-induced phosphorylation of HER3. The tumor cells may e.g. have been previously treated with trastuzumab.

Tables 2 and 3 below show the CDR1, CDR2 and CDR3 amino acid sequences of the heavy chain (Table 2) and the light chain (Table 3) of various anti-HER2 antibodies according to the invention. The amino acid sequences of the heavy chain variable region and the light chain, including the light chain variable region, of these antibodies, as well as the encoding DNA sequences (optimized for expression in CHO cells) are provided in the appended sequence listing. See Table 1 above for an overview of the SEQ ID numbers for these sequences.

TABLE 2

Heavy chain CDR1, CDR2 and CDR3 sequences of selected anti-HER2 antibodies

| Antibody Number | H CDR1 | H CDR2 | H CDR3 | SEQ ID NOs (CDR1/2/3) |
|---|---|---|---|---|
| 4517 | GFTFSSYG | ISGGGSYT | CARKGNYGNYGKLAYW | 45-47 |
| 4518 | GFNIKDIF | IDPANDNP | CAGGPAYFDYW | 48-50 |
| 4380/4381 | GYTFTNYW | IHPSDSDV | CAKSYYDSAMDYW | 51-53 |
| 4382 | GYTFTDYY | INPNNGGT | CVPGGLRSYFDYW | 54-56 |
| 4383 | GYTFTDYS | INTATGEP | CTAWAYEPYFDYW | 57-59 |
| 4384 | GYTFTSHW | INPSNGGT | CARAYYDFSWFVYW | 60-62 |
| 4385 | GYTFTGYW | ILPGSGST | CARWGDGSFAYW | 63-65 |
| 4386 | GYTFTSYW | IHPNSGSI | CAGYGNGPMDYW | 66-68 |
| 4387 | GYTFTNYW | ILPGGGYT | CARGSSGYPYYFDYW | 69-71 |
| 4519 | GYSFTDYN | IDPYNGGT | CARGAGYALDYW | 72-74 |

TABLE 3

Light chain CDR1, CDR2 and CDR3 sequences of selected anti-HER2 antibodies

| Antibody number | L CDR1 | L CDR2 | L CDR3 | SEQ ID NOs (CDR1/3) |
|---|---|---|---|---|
| 4517 | ENIYSN | AAT | CQHFWGTPWTF | 75-76 |
| 4518 | QDVIAA | WAS | CQQHYSTPWTF | 77-78 |
| 4380/4381 | KSVTTSGYSY | VAS | CHHSRELPWTF | 79-80 |
| 4382 | QDVSAA | WAS | CQQHYTTPPTF | 81-82 |
| 4383 | QDVFTA | SAS | CQQHFGIPWTF | 83-84 |
| 4384 | QDISNY | IS | CQQGNTLPLTF | 85-86 |
| 4385 | QNVGTA | STS | CQQYRSYPFTF | 87-88 |
| 4386 | SSVSY | RTS | CQQYHNYPLTF | 89-90 |
| 4387 | QDVGTA | WAS | CQQYSSYPYMYTF | 91-92 |
| 4519 | SSVSY | LTS | CQQWSSTPYTF | 89, 93 |

Another aspect of the invention relates to nucleic acid molecules comprising a nucleotide sequence that encodes an antibody of the invention, i.e. an antibody selected from the group consisting of antibodies 4380/4381, 4382, 4383, 4384, 4385, 4386, 4387, 4517, 4518 and 4519, or a humanized variant thereof; or encoding a heavy and/or light chain variable region sequence of such an antibody, or a heavy and/or light chain sequence having at least 80%, 85%, 90% or 95% sequence identity with such a heavy and/or light chain variable region sequence.

In one embodiment of this aspect of the invention, the nucleic acid molecule comprises a nucleotide sequence selected from the group consisting of SEQ ID NOS 1, 3, 5, 7, 9, 11, 13, 15, 17, 19, 21, 23, 25, 27, 29, 31, 33, 35, 37 and 39, or sequences that encode the same amino acid sequence as any one of said nucleotide sequences.

A further aspect of the invention relates to an expression vector comprising a nucleic acid molecule as defined above. As noted above, expression vectors for use in the context of the present invention may be of any suitable type known in the art, e.g. a plasmid or a viral vector.

A still further aspect of the invention relates to a host cell comprising a nucleic acid molecule as defined above, wherein said host cell is capable of expressing an anti-HER2 antibody encoded by said nucleic acid molecule.

In a further aspect the binding specificities of any two individual antibodies disclosed herein may be combined in one bispecific binding molecule. Such a bispecific binding molecule preferably comprises the heavy and light chain CDR1, CDR2 and CDR3 sequences of the two selected antibodies. The bispecific binding molecule may be a dual variable domain antibody, i.e. wherein the two arms of the antibody comprise two different variable domains, or may be in the form of an antibody fragment such as a bispecific Fab fragment or a bispecific scFv.

Production of Anti-HER2 Antibodies and Antibody Compositions

An additional aspect of the invention relates to methods for producing an anti-HER2 antibody or a polyclonal anti-HER2 antibody composition of the invention. One embodiment of this aspect of the invention relates to a method for producing an anti-HER2 antibody as defined herein, comprising providing a host cell as defined above capable of expressing an anti-HER2 antibody, cultivating said host cell under conditions suitable for expression of the antibody, and isolating the resulting antibody.

In another embodiment, the invention relates to method for producing a recombinant polyclonal anti-HER2 antibody composition comprising at least first and second recombinant anti-HER2 antibodies as described herein, the method comprising providing at least a first host cell and a second host cell, wherein the first and second host cells each are capable of expressing a recombinant anti-HER2 antibody, cultivating the first and second host cells under conditions suitable for expression of the first and second antibodies, and isolating the resulting first and second antibodies.

An antibody or antibody composition of the present invention may be produced by methods generally known in the art for production of recombinant monoclonal or polyclonal antibodies. Thus, in the case of production of a single antibody of the invention, any method known in the art for production of recombinant monoclonal antibodies may be used. For production of an antibody composition comprising two or more anti-HER2 antibodies of the invention, the individual antibodies may be produced separately, i.e. each antibody being produced in a separate bioreactor, or the individual antibodies may be produced together in single bioreactor. When the number of different antibodies in a composition is more than e.g. two or three, it will generally be preferably for reasons of cost efficiency to produce the antibodies together in a single bioreactor. On the other hand, when the composition only contains a small number of different antibodies, e.g. two, three or possibly four different antibodies, a decision to produce them separately in different bioreactors or together in a single bioreactor will have to be made based on the individual circumstances. If the antibody composition is produced in more than one bioreactor, the purified anti-HER2 antibody composition can be obtained by pooling the antibodies obtained from individually purified supernatants from each bioreactor. Various approaches for production of a polyclonal antibody composition in multiple bioreactors, where the cell lines or antibody preparations are combined at a later point upstream or prior to or during downstream processing, are described in WO 2009/129814 (incorporated by reference).

In the case of production of two or more individual antibodies in a single bioreactor, this may be performed e.g. as described in WO 2004/061104 or WO 2008/145133 (both of which are incorporated herein by reference). The method described in WO 2004/061104 is based on site-specific integration of the antibody coding sequence into the genome of the individual host cells, ensuring that the $V_H$ and $V_L$ protein chains are maintained in their original pairing during production. Furthermore, the site-specific integration minimizes position effects, and therefore the growth and expression properties of the individual cells in the polyclonal cell line are expected to be very similar. Generally, the method involves the following: i) a host cell with one or more recombinase recognition sites; ii) an expression vector with at least one recombinase recognition site compatible with that of the host cell; iii) generation of a collection of expression vectors by transferring the selected $V_H$ and $V_L$ coding pairs from the screening vector to an expression vector such that a full-length antibody or antibody fragment can be expressed from the vector (such a transfer may not be necessary if the screening vector is identical to the expression vector); iv) transfection of the host cell with the collection of expression vectors and a vector coding for a recombinase capable of combining the recombinase recognition sites in the genome of the host cell with that in the vector; v) obtaining/generating a polyclonal cell line from the transfected host cell and vi) expressing and collecting the antibody composition from the polyclonal cell line.

WO 2008/145133 describes an alternative approach to production of two or more different antibodies in a single bioreactor. This method involves generation of a polyclonal cell line capable of expressing a polyclonal antibody or other polyclonal protein comprising two or more distinct members by a) providing a set of expression vectors, wherein each of said vectors comprises at least one copy of a distinct nucleic acid encoding a distinct member of the polyclonal protein, separately transfecting host cells with each of the expression vectors under conditions avoiding site-specific integration of the expression vectors into the genome of the cells, thereby obtaining two or more compositions of cells, each composition expressing one distinct member of the polyclonal protein, and c) mixing the at least two compositions of cells to obtain a polyclonal cell line. The methods of WO 2004/061104 and WO 2008/145133 both have the advantage of allowing all of the members constituting the recombinant polyclonal antibody to be produced in a single bioreactor and to be purified in a single process, thereby avoiding the need for separate production and purification processes for each antibody, while at the same time resulting in a surprisingly uniform production of the different antibodies. The method of WO 2008/145133 has the further advantage of providing an increased yield, since each production cell can carry multiple copies of the polynucleotide encoding a particular antibody.

The antibodies of the invention may be produced in various types of cells, including mammalian cells as well as non-mammalian eukaryotic or prokaryotic cells, such as plant cells, insect cells, yeast cells, fungi, *E. coli* etc. However, the antibodies are preferably produced in mammalian cells, for example CHO cells, COS cells, BHK cells, myeloma cells (e.g. Sp2/0 or NS0 cells), fibroblasts such as NIH 3T3, or immortalized human cells such as HeLa cells, HEK 293 cells or PER.C6 cells.

Methods for transfecting a nucleic acid sequence into a host cell are well-known in the art (see, e.g., Sambrook et al., Molecular Cloning: A Laboratory Manual, Cold Spring Harbor Laboratory Press, 3rd Edition, 2001). For site-specific integration e.g. as described in WO 2004/061104, a suitable host cell will comprise one or more recombinase recognition sites in its genome. In this case, a suitable expression vector comprises a recombination recognition site matching the recombinase recognition site(s) of the host cell. Further details regarding e.g. transfer of selected VH and VL coding pairs from a screening vector using the site-specific integration approach may be found in WO 2004/061104.

When an antibody composition of the invention comprising two or more anti-HER2 antibodies is to be produced in a single bioreactor, cell lines with similar proliferation rates and preferably similar antibody expression levels may be selected to generate a polyclonal cell line. The polyclonal cell line is then generated by mixing the individual cell lines in a predefined ratio. See WO 2009/129814, WO 2004/061104 and WO 2008/145133 (incorporated herein by reference) for further information and examples relating to generating polyclonal cell lines expressing a polyclonal antibodies as well as production of polyclonal antibodies using such cell lines.

One embodiment of the present invention is thus a polyclonal cell line capable of expressing two or more anti-HER2 antibodies of the present invention. A further embodiment is a polyclonal cell line wherein each individual cell is capable of expressing a single $V_H$ and $V_L$ pair, and the polyclonal cell line as a whole is capable of expressing a collection of $V_H$ and $V_L$ pairs, where each $V_H$ and $V_L$ pair encodes an anti-HER2 antibody.

A recombinant antibody composition of the present invention may be manufactured in a single bioreactor by culturing one ampoule from a polyclonal working cell bank (pWCB) in an appropriate medium for a period of time to allow for a sufficient level of antibody expression while maintaining substantial uniformity in the relative expression levels of the individual antibodies expressed by the polyclonal cell line. A production time of between approximately 15 and 50 days will normally be suitable. Culturing methods known in the art such as fed batch or perfusion culturing may be used. The culture medium is preferably a serum-free medium, more preferably a serum-free and protein free medium, e.g. a chemically defined medium. Such culture media are typically designed for growth of the particular cell type being used for production, and numerous suitable media formulations are commercially available.

The recombinant antibody composition is obtained from the culture medium and purified by conventional purification techniques. These may include, for example, affinity chromatography combined with subsequent purification steps such as ion-exchange chromatography, hydrophobic interaction chromatography and gel filtration, as these purification techniques have frequently been used for the purification of recombinant antibodies. When two or more antibodies are produced by a polyclonal cell line in a single bioreactor, the presence of all the individual members in the polyclonal antibody composition is typically assessed subsequent to purification, for example by ion-exchange chromatography. Characterization of a polyclonal antibody composition may be performed e.g. as described in WO 2006/007853 and WO 2009/065414 (incorporated herein by reference).

Therapeutic Compositions

Another aspect of the invention is a pharmaceutical composition comprising as an active ingredient at least one anti-HER2 antibody of the invention, or an anti-HER2 recombinant Fab or another anti-HER2 recombinant antibody fragment composition. Preferably, the active ingredient of such a pharmaceutical composition is an anti-HER2 recombinant antibody composition as described above comprising two or more anti-HER2 antibodies. Such compositions are intended for amelioration, prevention and/or treatment of cancer. The pharmaceutical composition may be administered to a human or to a domestic animal or pet, but will typically be administered to humans.

The ratio between the individual antibodies in a therapeutic composition of the invention, or, in the case of individual antibodies of the invention being administered simultaneously, sequentially or separately, the ratio between the antibodies to be administered, will often be such that the antibodies are administered in equal amounts, but this need not necessarily be the case. Thus, a composition of the invention comprising two anti-HER2 antibodies will often contain them in a 1:1 ratio, and a composition comprising three anti-HER2 antibodies will often contain them in a 1:1:1 ratio. Depending on the characteristics of the individual antibodies, however, it may be desirable to use non-equal amounts of the different antibodies. Suitable ratios for the different anti-HER2 antibodies in compositions of the invention may be determined as described in WO 2010/040356 (incorporated herein by reference), which describes methods for identifying and selecting the optimal stoichiometric ratio between chemical entities in a combinatorial drug product, e.g. a polyclonal antibody composition, to obtain a combinatorial drug with optimal potency and efficacy.

In addition to at least one antibody of the invention or fragment thereof, the pharmaceutical composition will further comprise at least one pharmaceutically acceptable diluent, carrier or excipient. These may for example include preservatives, stabilizers, surfactants/wetting agents, emulsifying agents, solubilizers, salts for regulating the osmotic pressure and/or buffers. Solutions or suspensions may further comprise viscosity-increasing substances, such as sodium carboxymethylcellulose, carboxymethylcellulose, dextran, polyvinylpyrrolidone or gelatin. A suitable pH value for the pharmaceutical composition will generally be in the range of about 5.5 to 8.5, such as about 6 to, 8, e.g. about 7, maintained where appropriate by use of a buffer.

Conventional pharmaceutical practice may be employed to provide suitable formulations or compositions to administer to e.g. cancer patients. The administration will typically be therapeutic, meaning that it is administered after a cancer condition has been diagnosed. Any appropriate route of administration may be employed, for example parenteral, intravenous, intra-arterial, subcutaneous, intramuscular, intraperitoneal, intranasal, aerosol, suppository or oral administration. Pharmaceutical compositions of the invention will typically be administered in the form of liquid solutions or suspensions, more typically aqueous solutions or suspensions, in particular isotonic aqueous solutions or suspensions.

The pharmaceutical compositions of the invention are prepared in a manner known per se, for example, by means of conventional dissolving, lyophilizing, mixing, granulating or confectioning processes. The pharmaceutical compositions may be formulated according to conventional pharmaceutical practice (see, for example, Remington: The Science and Practice of Pharmacy (21st edition), ed. A. R. Gennaro, 2005, Lippincott Williams & Wilkins, Philadelphia, Pa., USA; and Encyclopedia of Pharmaceutical Technology, ed. J. Swarbrick, $3^{rd}$ edition, 2006, Informa Healthcare, New York, N.Y., USA).

As an alternative to a liquid formulation, the compositions of the invention may be prepared in lyophilized form comprising the at least one antibody alone or together with a carrier, for example mannitol, in which case the composition is reconstituted with a liquid such as sterile water prior to use.

The pharmaceutical compositions comprise from approximately 1% to approximately 95%, preferably from approximately 20% to approximately 90%, active ingredient. Pharmaceutical compositions according to the invention may e.g. be produced in unit dose form, such as in the form of ampoules, vials, suppositories, tablets or capsules. The formulations can be administered to human individuals in therapeutically or prophylactically effective amounts (e.g., amounts which prevent, eliminate, or reduce a pathological condition) to provide therapy for a cancerous disease or other condition. The preferred dosage of therapeutic agent to be administered is likely to depend on such variables as the severity of the cancer, the overall health status of the particular patient, the formulation of the compound excipients, and its route of administration.

Therapeutic Uses of Antibodies and Compositions According to the Invention

The anti-HER2 antibodies and pharmaceutical compositions according to the present invention may be used for the treatment or amelioration of a disease, in a mammal, in particular treatment of cancer in humans. One embodiment of the invention is a method of preventing, treating or ameliorating one or more symptoms associated with cancer in a human or other mammal, comprising administering an effective amount of an anti-HER2 recombinant antibody composition of the present invention to said mammal.

A particular embodiment relates to a method for treating a human patient with a disorder characterized by overexpression of HER2, in particular cancer, the method comprising administering to said patient a recombinant anti-HER2 antibody as defined herein or, preferably, a recombinant antibody composition comprising at least two anti-HER2 antibodies as defined herein.

An additional embodiment relates to a method for reducing heterodimer formation between HER2 and other ErbB family receptors in cells that overexpress HER2, the method comprising contacting said cells with a recombinant anti-HER2 antibody as defined herein or, preferably, a recombinant antibody composition comprising at least two anti-HER2 antibodies as defined herein.

A further embodiment of the present invention is the use of an anti-HER2 recombinant antibody or antibody composition of the present invention for the preparation of a composition for the treatment, amelioration or prevention of one or more symptoms associated with cancer in a human or other mammal, e.g. for treatment of a human patient with a disorder characterized by overexpression of HER2.

Based upon a number of factors, including HER2 expression levels, the following tumor types in particular may be indicated for treatment with an antibody composition of the invention: breast, ovarian, gastric, colon, rectum, prostate, bladder, pancreas, head and neck, and non-small cell lung cancer. Antibody compositions of the invention are contemplated to be particularly applicable to treatment of cancers that overexpress HER2, for example certain epithelial cancers such as many breast cancers, ovarian cancers and gastric (stomach) cancers.

In connection with each of these indications, two main clinical pathways are contemplated, namely 1) adjunctive therapy in connection with at least one additional therapeutic treatment or 2) as a monotherapy. These two options are briefly discussed below.

1) Adjunctive therapy: In adjunctive therapy, also known as combination therapy, patients will be treated with antibodies of the present invention in combination with at least one additional therapeutic treatment, typically a chemotherapeutic or antineoplastic agent and/or radiation therapy. Alternatively or additionally, the anti-HER2 antibodies and compositions of the invention may also be used in combination with a different anti-cancer antibody, e.g. an antibody targeting EGFR or VEGF. The primary cancer targets listed above may thus be treated by administration of an antibody or composition of the invention in addition to standard first line and second line therapy. Protocol designs will address effectiveness as assessed e.g. by reduction in tumor mass as well as the ability to reduce usual doses of standard chemotherapy. Such dosage reductions may allow additional and/or prolonged therapy by reducing dose-related toxicity of the chemotherapeutic agent.

By combining the antibody compositions of the invention with agents known to induce terminal differentiation of cancer cells, the effect may be improved further. Such compounds may, for example, be selected from the group consisting of retinoic acid, trans-retinoic acids, cis-retinoic acids, phenylbutyrate, nerve growth factor, dimethyl sulfoxide, active form vitamin D3, peroxisome proliferator-activated receptor gamma, 12-O-tetradecanoylphorbol 13-acetate, hexamethylene-bis-acetamide, transforming growth factor-beta, butyric acid, cyclic AMP, and vesnarinone. Preferably, the compound is selected from the group consisting of retinoic acid, phenylbutyrate, all-trans-retinoic acid, active form vitamin D.

Pharmaceutical articles comprising an antibody composition of the invention and at least one chemotherapeutic or antineoplastic compound may be used as a combination treatment for the simultaneous, separate or successive administration in cancer therapy. The chemotherapeutic compound may by any chemotherapeutic agent suitable for treatment of the particular cancer in question, for example an agent selected from the group consisting of alkylating agents, for example platinum derivatives such as cisplatin, carboplatin or oxaliplatin; plant alkoids, for example paclitaxel, docetaxel or irinotecan; antitumor antibiotics, for example doxorubicin (adriamycin); topoisomerase inhibitors such as topotecan; and antimetabolites, for example fluorouracil or other fluoropyrimidines.

It is also contemplated that antibodies of the invention may be used in adjunctive therapy in connection with tyrosine kinase inhibitors (TKIs). These are synthetic, mainly quinazoline-derived, low molecular weight molecules that interact with the intracellular tyrosine kinase domain of receptors and inhibiting ligand-induced receptor phosphorylation by competing for the intracellular Mg-ATP binding site. Several tyrosine kinase inhibitors that block HER2 kinase are currently in clinical development. Some of these also target EGFR or other EGFR family receptors. For a review of these TKIs see Spector et al. (2007) *Breast Cancer Res.* 9(2): 205. Pharmaceutical articles comprising an antibody composition of the invention and at least one TKI targeting HER2 may thus also be used as a combination treatment for the simultaneous, separate or successive administration in cancer therapy.

In other embodiments, the antibody compositions of the present invention may be used in combination with other antibody therapeutics. Examples of these include e.g. antibodies against EGFR (Erbitux® or Vectibix®) or VEGF (Avastin®). In yet other embodiments, the antibody compositions of the present invention may be used in combination with an agent known to stimulate cells of the immune system, such combination treatment leading to enhanced immune-mediated enhancement of the efficacy of the antibody compositions of the invention. Examples of such immune-stimulating agents include recombinant interleukins (e.g. IL-21 and IL-2).

2) Monotherapy: In connection with the use of the antibodies in accordance with the present invention in monotherapy of tumors, the antibodies may be administered to patients without concurrent use of a chemotherapeutic or antineoplastic agent, i.e. as a stand-alone therapy.

Immunoconjugates

Another option for therapeutic use of the antibodies and compositions of the invention is in the form of immunoconjugates, i.e. antibodies conjugated to one or more anti-cancer agents. In particular in the case of compositions comprising two or more individual antibodies of the invention that bind distinct HER2 epitopes, it is contemplated that this may generate a cross-linked antibody-receptor lattice on the cell surface, thereby potentially resulting in an increased level of receptor internalization as compared to the use of a single monoclonal antibody. Conjugation of one or more of the individual antibodies of such a composition to one or more anti-cancer agents therefore has the potential to specifically and effectively deliver the conjugated anti-cancer agents to the interior of tumor cells, thereby augmenting the effect of the anti-HER2 antibodies of the invention to provide an improved tumor cell-killing activity.

Various types of anti-cancer agents may be conjugated to the antibodies of the invention, including cytotoxic agents (including conventional chemotherapy agents and other small molecule anti-cancer drugs), cytokines (in which case the conjugate may be termed an "immunocytokine"), toxins (in which case the conjugate may be termed an "immunotoxin") and radionuclides, and a few immunoconjugates have already been approved for clinical use. These include Zevalin® (a murine anti-CD20 antibody conjugated to $^{90}$Y), Bexxar® (a murine anti-CD20 antibody conjugated to $^{131}$I) and Mylotarg® (a humanized anti-CD33 antibody conjugated to calicheamicin). Other immunoconjugates that have been tested in clinical trials include antibodies conjugated to e.g. doxorubicin or a maytansinoid compound. Immunotoxins that have been tested in clinical trials include several antibodies conjugated to a truncated *Pseudomonas* exotoxin A. An immunocytokine comprising a humanized EpCAM antibody conjugated to IL-2 has also been tested.

In the case of antibodies of the invention conjugated to cytotoxic agents, these may e.g. belong to any of the major classes of chemotherapy drugs, including alkylating agents (e.g. carboplatin, cisplatin, oxaliplatin), antimetabolites (e.g. methotrexate, capecitabine, gemcitabine), anthracyclines (e.g. bleomycin, doxorubicin, mitomycin-C) and plant alkaloids (e.g. taxanes such as docetaxel and paclitaxel, and vinca alkaloids such as vinblastine, vincristine and vinorelbine). Since the use of immunoconjugates specifically directs the anti-cancer agent to the tumors, and in particular to the interior of the tumor cells subsequent to internalization, immunoconjugates based on the anti-HER2 antibodies of the invention may advantageously be based on highly cytotoxic agents such as calicheamicin or maytansine derivatives, or on toxins such as bacterial toxins (e.g. *Pseudomonas* exotoxin A, diphtheria toxin) or plant toxins (e.g. ricin).

The conjugated anti-cancer agent in an immunoconjugate is generally linked to the antibody by means of a labile linker that is relatively stable in serum but which allows release of the agent when the immunoconjugate is internalized into the target cell. Suitable linkers include, for example, chemical linkers that are stable at neutral pH in serum but are subjected to acid hydrolysis in the mildly acidic conditions within the lysosomes subsequent to internalization, disulfide linkers that are cleaved by intracellular thiols, and peptide linkers that are stable in serum but which are subjected to enzymatic cleavage in intracellular compartments.

Various conjugation arrangements can be envisioned in compositions containing two or more antibodies of the invention. For example, with two antibodies it would be possible to conjugate the antibodies to two or more different anti-cancer drugs or to conjugate one antibody to a prodrug which is activated by an agent such as an enzyme conjugated to the other antibody. The general concept of antibody-directed enzyme prodrug therapy (ADEPT) has been described for monoclonal antibodies, where a prodrug is activated by an enzyme targeted to the tumor by a mAB-enzyme conjugate, but the present invention may provide an opportunity for tailoring this approach to particular conditions. It may thus be possible to specifically increase tumor cell killing while sparing or reducing damage to normal tissues.

For further information on anti-cancer immunoconjugates, see Wu et al. (2005) *Nature Biotechnology* 23(9):1137-1146; Schrama et al. (2006) *Nature Reviews/Drug Discovery* 5:147-159; and Rohrer (2009) *chimica oggi/Chemistry Today* 27(5): 56-60.

Dose and Route of Administration

The antibodies and compositions of the invention will be administered in an effective amount for treatment of the condition in question, i.e. at dosages and for periods of time necessary to achieve a desired result. A therapeutically effective amount may vary according to factors such as the particular condition being treated, the age, sex and weight of the patient, and whether the anti-HER2 antibodies are being administered as a stand-alone treatment or in combination with one or more additional anti-cancer treatments.

An effective amount for tumor therapy may be measured by its ability to stabilize disease progression and/or ameliorate symptoms in a patient, and preferably to reverse disease progression, e.g. by reducing tumor size. The ability of an antibody or composition of the invention to inhibit cancer may be evaluated by in vitro assays, e.g. as described in the examples, as well as in suitable animal models that are predictive of the efficacy in human tumors. Suitable dosage regimens will be selected in order to provide an optimum therapeutic response in each particular situation, for example, administered as a single bolus or as a continuous infusion, and with possible adjustment of the dosage as indicated by the exigencies of each case.

While specific dosing for antibodies in accordance with the invention has not yet been determined, certain dosing considerations can be determined through comparison with a similar product (an anti-HER2 monoclonal antibody) that has been approved for therapeutic use. It is thus contemplated that an appropriate dosage of an antibody composition of the invention will be similar to the recommended dosage for the anti-HER2 monoclonal antibody trastuzumab (Herceptin®). Depending on the particular condition, Herceptin is administered (by way of infusion) for treatment of breast cancer at either an initial dose of 4 mg/kg and subsequent weekly doses of 2 mg/kg, or an initial dose of 8 mg/kg and subsequent doses of 6 mg/kg every three weeks.

It is contemplated that a suitable dose of an antibody composition of the invention will be in the range of 0.1-100 mg/kg, such as about 0.5-50 mg/kg, e.g. about 1-20 mg/kg. The antibody composition may for example be administered in a dosage of at least 0.25 mg/kg, e.g. at least 0.5 mg/kg, such as at least 1 mg/kg, e.g. at least 1.5 mg/kg, such as at least 2 mg/kg, e.g. at least 3 mg/kg, such as at least 4 mg/kg, e.g. at least 5 mg/kg; and e.g. up to at most 50 mg/kg, such as up to at the most 30 mg/kg, e.g. up to at the most 20 mg/kg, such as up to at the most 15 mg/kg. Administration will normally be repeated at suitable intervals, e.g. once every week, once every two weeks, once every three weeks, or once every four weeks, and for as long as deemed appropriate by the responsible doctor, who may optionally increase or decrease the dosage as necessary.

Three distinct delivery approaches are contemplated for delivery of the antibodies of the invention. Conventional intravenous delivery will presumably be the standard delivery technique for the majority of tumors. However, in connection with tumors in the peritoneal cavity, such as tumors of the ovaries, biliary duct, other ducts, and the like, intraperitoneal administration may prove favourable for obtaining high dose of antibody at the tumor and to minimize antibody clearance. Similarly, certain solid tumors possess vasculature that is appropriate for regional perfusion. Regional perfusion may allow the obtainment of a high dose of the antibody at the site of a tumor and minimize short term clearance of the antibody.

As with any protein or antibody infusion-based therapeutic product, safety concerns are related primarily to (i) cytokine release syndrome, i.e. hypotension, fever, shaking, chills, (ii) the development of an immunogenic response to the protein (i.e. development of human antibodies by the patient to the recombinant antibody product), and (iii) toxicity to normal cells that express the HER2 receptor, e.g. many epithelial cells. Standard tests and follow-up procedures are utilised to monitor any such safety concerns.

All patent and non-patent references cited in the present application are hereby incorporated by reference in their entirety.

The invention will be further described in the following non-limiting examples.

EXAMPLES

Example 1

Cloning of Anti-HER2 Antibodies

Immunization

Female BALB/c, strain A, or C57 B16 mice (8-10 weeks old) were used for immunizations by injections with different purified proteins in addition to HER2-overexpressing cells.

Commercially available HER2 protein (R&D Systems cat. #1129-ER) was used for the protein immunizations. The human breast cancer cell line AU565 (ATCC, CRL-2351) was used for the cell-based immunizations. Cells were cultured in RPMI-1640 medium supplemented with 10% FBS (Fetal Bovine Serum) and 1% Penicillin/Streptomycin (P/S). Before each immunization the cells were washed in PBS, trypsinized with TrypLE and resuspended in growth medium. The cell suspensions were subsequently washed twice in PBS by centrifugation at 250×g for 5 min, followed by dislodging and resuspension in 15 ml sterile PBS.

Cells or antigen were diluted in PBS and then mixed 1:1 with Freund's Adjuvant. Adjuvant is used to enhance and modulate the immune response. For the first immunizations Complete Freund's Adjuvant (CFA) was used, whereas Incomplete Freund's Adjuvant (IFA) was used for the subsequent immunizations. IFA is an oil-in-water emulsion composed of mineral oils, and CFA is IFA to which heat-killed, dried *Mycobacterium* species are added. Both adjuvants have a depot effect. CFA gives rise to long-term persistence of the immune response and is used for the first immunizations to boost the immune response and WA is used for subsequent immunizations. The emulsions were tested by adding a drop on the surface of a glass with water. If the drop remains as one drop, the emulsion is stable and the injections can be performed. Only stable emulsions were administered to mice.

Depending on the schedule (see Table 4), 25-100 µg antigen or $10^7$ cells were used for each injection. In total, mice received 4 injections. All mice were injected with either 300 µl or 200 µl emulsion. Depending on the schedule, injections were performed subcutaneously (s.c.), intraperitoneally (i.p.) or intravenously (i.v.).

At termination, the mice were sacrificed by cervical dislocation, and the spleens were removed and transferred to a 74 µm cell strainer (Corning#136350-3479). The cells were macerated through the filter, resuspended in cold RPMI-1640 with 10% FBS and centrifuged at 300×g for 5 minutes. The cell pellet was resuspended in RPMI-1640 with 1% FBS, filtered through a 50 µm syringe filter (BD#340603) and collected by centrifugation. The cell pellet was cryopreserved after resuspension in FCS (fetal calf serum) with 10% DMSO and frozen cells were stored at −80° C. until FACS sorting.

FACS Sorting of Murine Plasma Cells

Vials with frozen splenocytes were thawed at 37° C. and transferred to 15 ml tubes with ice still present. 10 ml ice-cold RPMI, 10% FBS was added one drop at a time to the tube while swirling. After one wash in 10 ml FACS PBS, 5 ml FCS PBS was added before filtering the cells through 50 µm Filcon. Cells were then pelleted and resuspended in 1 ml PBS with 2% FBS (final volume) and stained with anti-CD43-FITC and anti-CD138-PE according to the specific dilution to a final concentration of approx. 5 µg/ml. Cells were incubated at 4° C. for 20 min in the dark. Subsequently, cells were washed 2 times with 2 ml FACS buffer. Up to 15 ml FACS PBS was added. Propidium iodide (PI) was added at 1:100 (1 part PI to 100 parts FACS PBS buffer), and cells were subsequently sorted into 96-well PCR plates containing PCR reaction buffer (see below), and spun down for 2 min at 400×g before the plates were frozen at −80° C. Plasma cells were gated as CD43-positive/CD-138 positive.

Linkage of Cognate $V_H$ and $V_L$ Pairs

Linkage of $V_H$ and $V_L$ coding sequences was performed on the single cells gated as plasma cells, facilitating cognate pairing of the $V_H$ and $V_L$ coding sequences. The procedure utilized a two step PCR procedure based on a one-step multiplex overlap-extension RT-PCR followed by a nested PCR. The primer mixes used in the present example only amplify kappa light chains. Primers capable of amplifying lambda light chains could, however, be added to the multiplex primer mix and nested PCR primer mix if desired. If lambda primers are added, the sorting procedure should be adapted such that lambda positive cells are not excluded. The principle for linkage of cognate $V_H$ and $V_L$ sequences is described in detail in WO 2005/042774 and in Meijer et al. (2006) *J Mol. Biol.* 358(3):764-72.

96-well PCR plates were thawed and the sorted cells served as template for the multiplex overlap-extension RT-PCR. The sorting buffer added to each well before the single-cell sorting contained reaction buffer (OneStep RT-PCR Buffer; Qiagen), primers for RT-PCR (see Table 5) and RNase inhibitor (RNasin, Promega). This was supplemented with OneStep RT-PCR5Enzyme Mix (25× dilution; Qiagen) and dNTP mix (200 µM each) to obtain the given final concentration in a 20 µl reaction volume. The plates were incubated for 30 min at 55° C. to allow for reverse transcription (RT) of the RNA from each cell. Following the RT, the plates were subjected to the following PCR cycle: 10 min at 94° C., 35×(40 sec at 94° C., 40 sec at 60° C., 5 min at 72° C.), 10 min at 72° C.

The PCR reactions were performed in a H20BIT Thermal Cycler with a Peel Seal Basket for 24 96-well plates (ABgene) to facilitate a high-throughput. The PCR plates were stored at −20° C. after cycling.

For the nested PCR step, 96-well PCR plates were prepared with the following mixture in each well (20 µl reactions) to obtain the given final concentration: 1× FastStart buffer (Roche), dNTP mix (200 µM each), nested primer mix (see Table 6), Phusion DNA Polymerase (0.08 U; Finnzymes) and FastStart High Fidelity Enzyme Blend (0.8 U; Roche). As template for the nested PCR, 1 µl was transferred from the multiplex overlap-extension PCR reactions. The nested PCR plates were subjected to the following thermocyling: 35×(30 sec at 95° C., 30 sec at 60° C., 90 sec at 72° C.), 10 min at 72° C. Randomly selected reactions were analyzed on a 1% agarose gel to verify the presence of an overlap-extension fragment of approximately 890 basepairs (bp). The plates were stored at −20° C. until further processing of the PCR fragments.

The repertoires of linked $V_H$ and $V_L$ coding pairs from the nested PCR were pooled, without mixing pairs from different donors, and were purified by preparative 1% agarose gel electrophoresis. The human kappa constant light chain encoding sequence was spliced by overlap extension to the $V_L$ coding region of the pooled PCR products of linked $V_H$ and $V_L$ coding pairs as described in WO 2008/104183. The human kappa constant light chain encoding sequence was amplified from a plasmid containing the coding sequence of a human antibody with a kappa light chain in a reaction containing: Phusion Enzyme (2 U; Finnzymes), 1× Phusion buffer, dNTP mix (200 µM each), hKCforw-v2 primer and Kappa3' primer (Table 5), and plasmid template pLL138 (10 ng/µl) in a total volume of 50 µl. The reaction was subjected to the following thermocycling: 25×(30 sec at 95° C., 30 sec at 55° C., 45 sec at 72° C.), 10 min at 72° C. The resulting PCR fragment was purified by preparative 1% agarose gel electrophoresis.

The purified pooled PCR fragments, from each repertoire were spliced to the amplified and purified PCR fragment of the human kappa constant encoding region (SEQ ID NO:41) by the following splicing by overlap extension PCR (50 µl total volume) containing: human kappa constant encoding region fragment (1.4 ng/µl), purified pooled PCR fragment (1.4 ng/µl), Phusion DNA Polymerase (0.5 U; Finnzymes) and FastStart High Fidelity Enzyme Blend (0.2 U; Roche), 1× FastStart buffer (Roche), dNTP mix (200 µM each), mhKCrev primer and mJH set primers (see Table 7). The reaction was subjected to the following thermocycling: 2 min at 95° C., 25×(30 sec at 95° C., 30 sec at 55° C., 1 min at 72° C.), 10 min at 72° C. The resulting PCR fragment (approx. 4518 bp) was purified by preparative 1% agarose gel electrophoresis.

Insertion of Cognate $V_H$ and $V_L$ Coding Pairs into a Screening Vector

In order to identify antibodies with binding specificity to HER2, the $V_H$ and $V_L$ coding sequences obtained were expressed as full-length antibodies. This involved insertion of the repertoire of $V_H$ and $V_L$ coding pairs into an expression vector and transfection into a host cell.

A two-step cloning procedure was employed for generation of a repertoire of expression vectors containing the linked $V_H$ and $V_L$ coding pairs. Statistically, if the repertoire of expression vectors contains ten times as many recombinant plasmids as the number of cognate paired $V_H$ and $V_L$ PCR products used for generation of the screening repertoire, there is a 99% likelihood that all unique gene pairs are represented. Thus, if 400 overlap-extension V-gene fragments were obtained, a repertoire of at least 4000 clones would be generated for screening to have a 99% likelihood of obtaining all unique gene pairs.

Briefly, the purified PCR product of the repertoires of linked $V_H$ and $V_L$ coding pairs, spliced to the human kappa constant coding region, were cleaved with XhoI and NotI DNA endonucleases at the recognition sites introduced into the termini of PCR products. The cleaved and purified fragments were ligated into an XhoI/NotI digested mammalian IgG expression vector, 00-VP-002 (described in WO 2008/104183), by standard ligation procedures. The ligation mix was electroporated into E. coli and added to 2×YT plates containing the appropriate antibiotic and incubated at 37° C. over night. The amplified repertoire of vectors was purified from cells recovered from the plates using standard DNA purification methods (Qiagen). The plasmids were prepared for insertion of promoter-leader fragments by cleavage using AscI and NheI endonucleases. The restriction sites for these enzymes were located between the $V_H$ and $V_L$ coding gene pairs. Following purification of the vector, an AscI-NheI digested bi-directional mammalian promoter-leader fragment was inserted into the AscI and NheI restriction sites by standard ligation procedures. The ligated vector was amplified in E. coli and the plasmid was purified using standard methods. The generated repertoire of screening vectors was transformed into E. coli by conventional procedures. Colonies obtained were consolidated into 384-well master plates and stored.

Screening for Binding to HER2 Overexpressing Cells

Initially the antibody-libraries were screened for binders to the HER2-overexpressing breast cancer cell line (SKBR-3) using confocal microscopy. 5000 SKBR-3 cells were seeded into each well of 384-well cell carrier plates (Perkin Elmer, cat. #6007439) and allowed to attach overnight. 10 µl of antibody supernatant was transferred to each well and plates were incubated for 2 hours, after which the media in the wells was discarded and 30 µl new media containing 2 µg/ml of Alexa-488 labeled goat anti-human IgG (H+L, Invitrogen cat.# A11013), 2 µg/ml CellMask Blue (Invitrogen cat.# H34558) and 1 µM Hoechst 33342 (Invitrogen cat.# H3570) was added to each well and plates were incubated for another 30 minutes. The media was again discarded and the cells were washed and fixed with 2% formaldehyde solution (Aldrich cat. #533998). The level of fluorescence was then measured using an OPERA high throughput confocal microscope (Perkin Elmer).

The data from the confocal screening identified 266 positive hits corresponding to 3.46% of the total clones.

Sequence Analysis and Clone Selection

The clones identified as binding to SKBR-3 cells were retrieved from the original master plates (384-well format) and consolidated into new plates. DNA was isolated from the clones and submitted for DNA sequencing of the V-genes. The sequences were aligned and all the unique clones were selected. Multiple alignments of obtained sequences revealed the uniqueness of each particular clone and allowed for identification of unique antibodies. Following sequence analysis of 266 clones, more than 70 genetically distinct antibody sequence clusters were identified. Each cluster of related sequences has probably been derived through somatic hypermutations of a common precursor clone. Overall, one to two clones from each cluster were chosen for validation of sequence and specificity. Sequences of selected antibody variable regions are shown in the appended sequence listing. As explained above, the light chain sequences shown in the sequence listing all include the same human kappa constant region, which starts with amino acids -TVAAP- and ends at the C-terminal -NRGEC.

Sequence and Specificity Validation

In order to validate the antibody encoding clones, DNA plasmid was prepared and transfection of FreeStyle CHO—S cells (Invitrogen) at 2 ml scale was performed for expression. The supernatants were harvested 96 hours after transfection. Expression levels were estimated with standard anti-IgG ELISA, and the specificity was determined by HER2 specific ELISA and OPERA analysis of antibody binding to cells.

Briefly, for the ELISA, Nunc Maxisorb plates (cat. #464718) were coated with 1 µg/ml HER2 protein (R&D Systems cat. #1129-ER), diluted in PBS at 4° C. over night. Prior to blocking in 50 µl 2% Milk-PBS-T the plates were washed once with PBS+0.05% Tween 20 (PBS-T). The plates were washed once with PBS-T and 20 µl of 2% milk-PBS-T, and 5 µl supernatants from FreeStyle CHO—S transfectants (see below) were added and incubated for 1.5 hours at room temperature, after which the plates were washed once with PBS-T, 20 µl per well. Secondary antibody (HRP-Goat-anti-human kappa light chain, Serotec, cat.# STAR 100P) diluted 1:25000 in 2% milk-PBS-T was added to detect the antibodies bound to the wells and incubated for 1 hour at room temperature. The plates were washed once in PBS-T before addition of 25 µl substrate (Kem-En-Tec Diagnostics, cat. #4518) that was incubated for 5 min. 25 µl 1M sulphuric acid was added after the incubation to stop the reaction. Specific signal was detected on an ELISA reader at 450 nm. 178 of the 266 clones found to bind to SKBR-3 cells were also positive in the HER2ELISA.

TABLE 4

Immunization schedules used to generate starting material for anti-HER2 cloning

| Mouse group | Strain | Injection 1 | Injection 2 | Injection 3 | Injection 4 | Termination |
|---|---|---|---|---|---|---|
| 102 | Balb/c | Day 1<br>25 µg rhHER2<br>(R&D Systems 1129-ER)<br>CFA s.c. | Day 35<br>25 µg rhHER2<br>(R&D Systems 1129-ER)<br>IFA s.c | Day 56<br>25 µg rhHER2<br>(R&D Systems 1129-ER)<br>IFA s.c | Day 70<br>25 µg rhHER2<br>(R&D Systems 1129-ER)<br>IFA s.c | Day 73 |

TABLE 4-continued

Immunization schedules used to generate starting material for anti-HER2 cloning

| Mouse group | Strain | Injection 1 | Injection 2 | Injection 3 | Injection 4 | Termination |
|---|---|---|---|---|---|---|
| 122 | Balb/c | Day 1<br>1 × 10⁷ AU565 cells<br>CFA i.p. | Day 28<br>100 µg rhHER2<br>(R&D Systems 1129-ER)<br>IFA s.c. | Day 42<br>1 × 10⁷ AU565 cells IFA i.p. | Day 56<br>100 µg rhHER2<br>(R&D Systems 1129-ER)<br>IFA s.c. | Day 59 |
| 123 | C57/B16 | Day 1<br>1 × 10⁷ AU565 cells<br>CFA i.p. | Day 28<br>100 µg rhHER2<br>(R&D Systems 1129-ER)<br>IFA s.c. | Day 42<br>1 × 10⁷ AU565 cells IFA i.p. | Day 56<br>100 µg rhHER2<br>(R&D Systems 1129-ER)<br>IFA s.c. | Day 59 |
| 124 | Balb/c | Day 1<br>100 µg rhHER2<br>(R&D Systems 1129-ER)<br>CFA s.c. | Day 28<br>100 µg rhHER2<br>(R&D Systems 1129-ER)<br>IFA s.c. | Day 42<br>100 µg rhHER2<br>(R&D Systems 1129-ER)<br>IFA s.c. | Day 56<br>100 µg rhHER2<br>(R&D Systems 1129-ER)<br>IFA s.c. | Day 59 |
| 125 | C57/B16 | Day 1<br>100 µg rhHER2<br>(R&D Systems 1129-ER)<br>CFA s.c. | Day 28<br>100 µg rhHER2<br>(R&D Systems 1129-ER)<br>IFA s.c. | Day 42<br>100 µg rhHER2<br>(R&D Systems 1129-ER)<br>IFA s.c. | Day 56<br>100 µg rhHER2<br>(R&D Systems 1129-ER)<br>IFA s.c. | Day 61 |

TABLE 5

RT-PCR multiplex overlap-extension primer mix

| Primer name | Conc. (nM) | Sequence | SEQ ID |
|---|---|---|---|
| mHCre | 0.2 | GACSGATGGGCCCTTGGTGG | 94 |
| mKapp | 0.2 | GCTGTAGGTGCTGTCTTTGC | 95 |
| mVH | | | |
| mVH A | 0.04 | TATTCCCATGGCGCGCCSAG GTCCARCTGCARCAGYCTG | 96 |
| mVH B | 0.04 | TATTCCCATGGCGCGCCGAR GTGMAGCTKGTKGAGTC | 97 |
| mVH C | 0.04 | TATTCCCATGGCGCGCCSAG GTGCAGCTKMAGGAGTC | 98 |
| mVH 8 | 0.04 | TATTCCCATGGCGCGCCCAG GTTACTCTGAAAGAGTC | 99 |
| mVH 9 | 0.04 | TATTCCCATGGCGCGCCCAG ATCCAGTTGGTGCAGTCTG | 100 |
| mVK | | | |
| mVK D | 0.04 | GGCGCGCCATGGGAATAGCT AGCCGAYATCCAGATGAC | 101 |
| mVK E | 0.04 | GGCGCGCCATGGGAATAGCT AGCCRACATTGTGMTGAC | 102 |
| mVK F | 0.04 | GGCGCGCCATGGGAATAGCT AGCCSAMATTGTKCTSACC | 103 |
| mVK | 0.04 | GGCGCGCCATGGGAATAGCT AGCCGATRTTGTGATGACB | 104 |

W = A/T,
R = A/G,
S = G/C,
Y = C/T,
K = G/T,
M = A/C,
H = ACT,
B = GCT;
Conc.-final concentration.

TABLE 6

Nested primer set

| Primer name | Conc. (nM) | Sequence | SEQ ID |
|---|---|---|---|
| mHCre | 0.2 | GGACAGGGMTCCAKAGTTCCADKT | 105 |
| hmJK | | | |
| hmJK1- | 0.2 | GACAGATGGTGCAGCCACAGTTCG TTTGATTTCCAGC | 106 |
| hmJK2- | 0.2 | GACAGATGGTGCAGCCACAGTTCG TTTTATTTCCAGC | 107 |
| hmJK4- | 0.2 | GACAGATGGTGCAGCCACAGTTCG TTTTATTTCCAAC | 108 |
| hmJK5- | 0.2 | GACAGATGGTGCAGCCACAGTTCG TTTCAGCTCCAGC | 109 |

K = G/T,
M = A/C,
D = AGT;
Conc.-final concentration.

TABLE 7

Kappa constant splicing primer set

| Primer | Conc. (nM) | Sequence | SEQ ID |
|---|---|---|---|
| Human kappa constant amplification | | | |
| hKCfor | 0.2 | GAACTGTGGCTGCACCATCTGTC | 110 |
| Kappa3' | 0.2 | ACCGCCTCCACCGGCGGCCGCTT ATTAACACTCTCCCCT | 111 |
| Splicing by overlap extension | | | |
| mhKCrev | 0.2 | ACCGCCTCCACCGGCGGCCGCTT ATTAACACTCTCCCCTGTTGA- | 112 |
| mJH set | | | |
| mJH1 | 0.2 | GGAGGCGCTCGAGACGGTGACCGTGGTCCC | 113 |

TABLE 7-continued

Kappa constant splicing primer set

| Primer | Conc. (nM) | Sequence | SEQ ID |
|---|---|---|---|
| mJH2 | 0.2 | GGAGGCGCTCGAGACTGTGAGAGTGGTGCC | 114 |
| mJH3 | 0.2 | GGAGGCGCTCGAGACAGTGACCAGAGTCCC | 115 |
| mJH4 | 0.2 | GGAGGCGCTCGAGACGGTGACTGAGGTTCC | 116 |

Example 2

Functional Characterization of Selected Anti-HER2 Antibodies 41 unique antibodies were selected for functional testing using a viability assay. Cellular damage will inevitably result in loss of the ability of the cell to maintain and provide energy for metabolic cell function and growth. Metabolic activity assays are based on this premise, usually measuring mitochondrial activity. The cell proliferation reagent WST-1 (Roche Cat. No. 11 644 807 001) is a ready-to-use substrate which measures the metabolic activity of viable cells. It is assumed that the metabolic activity correlates with the number of viable cells. In this example the WST-1 assay was used to measure the number of metabolically active cells after treatment of cancer cells with 2 µg/ml of different anti-HER2 antibodies for 96 hours.

The cancer cell lines SKBR-3 (ATCC cat.# HTB-30), BT-474 (ATCC cat.#HTB-20), NCI-N87 (ATCC cat.# CRL-5822) and MDA-453 (ATCC cat.# HTB-130), were seeded into 96-well plates at a concentration of 1000 cells/well in media containing 2 µg/ml of anti-HER2 antibody. The plates were incubated for 4 days in a humidified incubator at 37° C. 20 µl of WST-1 reagent was then added per well and the plates were incubated for one hour at 37° C. Plates were then transferred to a orbital plate shaker and left for another hour. The absorbance was measured at 450 nm and 620 nm (reference wavelength) on an ELISA reader. The difference in the levels of metabolically active cells (MAC) was calculated as percent of the control supernatants as follows:

$$\% \, MAC = \left(1 - \frac{(ODexp. - ODmedia)}{(ODuntreat. - ODmedia)}\right) \times 100$$

The results of this analysis for selected antibodies are shown in Table 8 below, where data is provided for the individual cancer cell lines as well as the average and standard deviation. It is evident from these results that HER2 antibodies with a range of functional activities have been identified and that the antibodies in the repertoire exhibit an inhibitory effect on all or most of the tested cancer cell lines.

TABLE 8

Percent metabolically active cells (MAC) in the presence of anti-HER2 antibodies

| Antibody No. | SKBR-3 | BT-474 | N87 | MDA-453 | Average | Std. dev. |
|---|---|---|---|---|---|---|
| 3165* | 83 | 78 | 83 | 108 | 88 | 14 |
| 4382 | 94 | 68 | 88 | 90 | 85 | 12 |
| 4383 | 91 | 98 | 64 | 115 | 92 | 21 |
| 4384 | 88 | 66 | 61 | 78 | 73 | 12 |
| 4385 | 95 | 95 | 82 | 84 | 89 | 7 |
| 4386 | 87 | 89 | 47 | 98 | 80 | 23 |
| 4387 | 82 | 82 | 65 | 97 | 81 | 13 |
| 4517 | 94 | 83 | 69 | 81 | 82 | 10 |
| 4518 | 99 | 79 | 81 | 102 | 90 | 12 |
| 4519 | 98 | 79 | 105 | 96 | 95 | 11 |

*Ab 4380/4381 with Cys in position 40 of the light chain

Example 3

Determination of Overlapping Epitopes

For selection of mixtures containing anti-HER2 antibodies which exert a synergistic effect in combination, the antibodies in each mixture should bind distinct non-overlapping epitopes. Therefore, to investigate the degree of overlap between the anti-HER2 antibodies, epitope binning by Surface Plasmon Resonance (SPR) was performed. SPR analysis was performed on the ProteOn™ XPR 36 Protein Interaction Array System (Biorad Laboratories). This system allows for measurement of six interactions in two dimensions (defined as L and A) yielding a total of 36 possible interactions simultaneously.

Setup

A ProteOn GLC sensor Chip (BioRad) was conjugated with 3600-3620 Resonance Units (RU) of anti-Fc antibody (Biacore, GE Healthcare) injected into flow cells L1 to L6 using the ProteOn amine coupling kit (Biorad) according to the manufacturer's instructions. Using a flow rate of 25 µl/min, 125 µl Fc-conjugated HER2 (HER2-Fc) at a concentration of 50 nM was injected and captured on flow cells L1-L5, while running buffer (for composition see the reagents section below) was injected similarly into flow cell L6. In order to block free anti-Fc sites prior to injection of anti-HER2 antibodies, 125 µl of blocking monoclonal antibody (mAb) Synagis® (Abbott) was injected at a concentration of 0.33 mg/ml into flow cells L1 to L5, and running buffer was injected into L6, all at a flow rate of 250 min. Blocking mAb was allowed to dissociate for at least 300 seconds prior to injection of 100 µl anti-HER2 antibody at a concentration of 50 nM and a flow rate of 50 µl/min, followed by at least 10 seconds of dissociation. The multichannel module was then turned to the A dimension followed by the second injection of anti-HER2 antibody (using identical flow conditions and concentrations as outlined for the first injection of anti-HER2 antibody in the L dimension). All of the HER2 antibodies were tested for overlap one against the other in both dimensions and against themselves to confirm self-overlap (control representing 100% overlap between two antibodies) in a total of eight cycles. Between each cycle, antibody-EGFR complexes were stripped by regeneration with 25 µl 3 M MgCl$_2$ at a flow rate of 50 µl/min.

Reagents

GLC-Chip (Biorad, Cat. No. 176-5012)
ProteOn™ amine coupling kit (Biorad) EDC-NHS (cat# 176-2410)
Anti-Fc antibody (Biacore kit, cat# BR-1008-39)
Running buffer: PBS, 0.005% Tween-20 (PBS-T)

3M MgCl$_2$-regeneration buffer, Biacore cat. No 344-ER-050

Antigen: HER2-Fc, R&D systems cat. No 1129-ER reconstituted at 100 µg/ml in PBS

Blocking mAb: Synagis® (Abbott). Dissolved to a stock solution of 5 mg/ml in ddH$_2$O and diluted further to 0.33 mg/ml in running buffer Anti-HER2 antibodies: 4517, 4518, 4519, 4382, 4383, 4384, 4385, 4386, 4387+Herceptin® and pertuzumab analogue (where the pertuzumab analogue has the light chain and heavy chain amino acid sequences of pertuzumab as disclosed in WO 2006/033700 and US 2006/0121044 A1)

Results

RU max values were obtained after normalization to running buffer control and baseline correction, and the degree of inhibition of tested anti-HER2 antibodies was determined by comparing the RU max value of the individual anti-HER2 antibody before and after competition by introduction of report points recorded immediately before and after injection of each sample. An example of a typical XPR ProteOn cycle is shown in FIG. 1. Percentage overlap/binding inhibition of the first and second antibody is calculated based on the difference in RU-values before and after the first and second antibody, so that identical RU-values of the first and second antibody represents 100% overlap (i.e. 100% inhibition). At least two experiments were performed to confirm inhibition between two antibodies in both dimensions. Inhibition values of 50-100% (calculated as a mean from at least two independent experiments) were taken as an indication of significant competition between antibody pairs binding overlapping epitopes or epitopes in close proximity on the antigen, while inhibition values below 50% indicated that the epitopes recognized by the antibody pairs were not in close proximity, resulting in decreased steric hindrance. Inhibition values below 25% were not included in the analysis for overlapping epitopes, because they were judged to represent non-significant inhibition. The antibody pairs that were found to have 50-100% and 25-50% inhibition, respectively, are listed below.

Antibody Pair Combinations Exhibiting 50-100% Inhibition:
  4517 and 4518
  4517 and Herceptin
  4384 and 4518
  4382 and 4519
  4382 and 4383
  4382 and Pertuzumab analogue
  4383 and 4387
  4383 and Pertuzumab analogue
  4384 and 4386
  4385 and 4387

Antibody Pair Combinations Exhibiting 25-50% Inhibition:
  4387 and 4519
  4519 and Pertuzumab analogue
  4382 and 4387
  4383 and 4387
  4387 and Pertuzumab analogue FIG. 1 illustrates the results from a representative epitope binning of anti-HER2 antibodies of the invention. "HER2" designates the association period of Fc-conjugated HER2. "Block" designates the association time for the blocking antibody Synagis to block free anti-Fc sites. The blocked sites are represented by the difference in RU value between the end of "HER2" and the end of "Block" (in both cases determined at the end of the dissociation period, i.e. at about 600 and 1500 sec), designated "Blocked free Anti-Fc sites". "mAb1→" designates the association time of an anti-HER2 antibody in the first dimension. "ROTATE CHIP", indicates the shift to the second dimension. "mAb2↓" designates the association time of an anti-HER2 antibody in the second dimension. Percent inhibition is calculated as the fraction of RU in the first antibody binding (designated "mAb1 binding") that is obtained after binding of the second antibody (designated "mAb2 binding"). In this example, running buffer is injected twice in sample A1, the same antibody is injected twice in sample A2, and the antibody from A2 is injected with four different antibodies in sample A3, A4, A5 and A6. Self-overlap is observed for sample A2 (insignificant change in RU during mAb2↓; indicated by dashed arrow at lower right) but no significant overlap is observed between the antibody from A2 and the other antibodies.

Example 4

Functional Characterization of Mixtures of Two or Three Anti-HER2 Antibodies

This example describes in vitro testing of all possible mixtures of two or three antibodies among ten selected anti-HER2 antibodies of the invention with confirmed binding to human HER2. The antibody mixtures were evaluated for their ability to inhibit the growth of three different cancer cell lines: N87 (gastric cancer), SKBR-3 (breast cancer) and BT474 (breast cancer).

Methods

Antibodies 4380, 4381, 4382, 4383, 4384, 4385, 4387, 4517, 4518 and 4519, each of which had confirmed binding to the human HER2 receptor, were tested in all possible mixtures of two or three antibodies in order to identify antibody combinations with optimal efficacy. The methods used, e.g. for preparing the different antibody combinations in the 384-well plates, were those generally described in WO 2010/040356. Further details are provided below.

Mixtures of Two Antibodies

The ten antibodies were diluted to a concentration of 25 µg/ml in 1×PBS, and 100 µl of antibody solution was added to the wells of 384-well feeder plates for use in preparing mixtures of two antibodies for testing.

For each of the three cell lines tested, two separate 384-well plates were used, with 46 µl of media containing the relevant number of cells (N87: 3000 cells; SKBR-3: 1000 cells; BT474: 2000 cells) being added to the wells. A Biomek 3000 laboratory automation workstation (Beckman Coulter) was used to add 2 µl of each of two different antibodies from the feeder plates to the wells of the 384-well plates containing media+cells, such that all combinations of two different antibodies were represented. In addition, the plates included media control wells (50 µl 1×PBS media; no cells), untreated control wells (50 µl 1×PBS media+cells; no antibody), and wells containing (in addition to 46 µl of media+cells) either 4 µl of media with either Herceptin or a Pertuzumab analogue as a reference antibody or 4 µl of media with only one of the ten antibodies of the invention as an additional control.

The plates with wells containing mixtures of two antibodies, as well as media and untreated control wells and wells with Herceptin/Pertuzumab analogue or a single antibody of the invention, were incubated for 4 days in a humidified incubator at 37° C., after which 5 µl of the cell proliferation reagent WST-1 diluted 1:1 in 1×PBS was added to all relevant wells on the plates. The plates were then incubated for 1 hour at 37° C. and subsequently transferred to orbital shakers and incubated for another hour. The absorbance was measured at 450 nm and 620 nm (reference wavelength) on an ELISA reader. The amount of metabolically active cells (MAC) was calculated as a percentage of the untreated control as follows:

$$\% \, MAC = \left( \frac{(ODexp. - ODmedia)}{(ODuntreat. - ODmedia)} \right) \times 100$$

It is assumed that the metabolic activity correlates with the number of viable cells, a lower % MAC corresponding to a higher level of cell growth inhibition by the antibodies.

Mixtures of Three Antibodies

The same ten antibodies with confirmed binding to the human HER2 receptor were diluted to a concentration of 16.67 μg/ml in 1×PBS, and 100 μl of antibody solution was added to the wells of 384-well feeder plates for use in preparing mixtures of three antibodies for testing.

The same three cell lines were used for the 3-mix in vitro assays, i.e. N87, SKBR-3 and BT474. For each cell line tested, ten different 384-well plates were used, with 44 μl of media containing the same number of cells as set forth above being added to the wells. A Biomek 3000 laboratory automation workstation (Beckman Coulter) was used to add 2 μl of each of three different antibodies from the feeder plates to the wells of the 384-well plates containing media+cells, such that all combinations of three different antibodies were represented. In addition, the plates included media control wells (50 μl 1×PBS media; no cells), untreated control wells (50 μl 1×PBS media+cells; no antibody), and wells containing (in addition to 44 μl of media+cells) either 6 μl of media with either Herceptin or Pertuzumab analogue as a reference antibody or 6 μl of media with only one of the ten antibodies of the invention as an additional control.

The plates with wells containing mixtures of three antibodies, as well as media and untreated control wells and wells with Herceptin/Pertuzumab analogue or a single antibody of the invention, were incubated for 4 days in a humidified incubator at 37° C., after which 5 μl of the cell proliferation reagent WST-1 diluted 1:1 in 1×PBS was added to all relevant wells on the plates. The plates were then incubated for 1 hour at 37° C. and subsequently transferred to orbital shakers and incubated for another hour. The absorbance was measured at 450 nm and 620 nm and the % MAC was calculated as described above.

Results

All possible 2-mixes and 3-mixes of ten selected anti-HER2 antibodies with confirmed binding to human HER2 were evaluated for their ability to inhibit the growth of the three cancer cell lines N87 (gastric cancer), SKBR-3 (breast cancer) and BT474 (breast cancer). The % MAC was calculated for each of the ten individual monoclonal antibodies and for each of the mixtures of two or three antibodies. The mixtures were then ranked according to their effect on cell growth, and the 55 mixtures with the highest average efficacy (highest average % MAC, based on an average of the results for the three cell lines) are shown below in Table 8.

The results show that the growth inhibition effect of the various mixtures varies considerably between the different cell lines, while the difference in the average % MAC is less pronounced. Although the 55 antibody mixtures in Table 8 were selected based on the average % MAC, it is contemplated that individual antibody mixtures may be of interest based on an effect demonstrated in any one or more cell lines, and that a high level of inhibition (low % MAC) in just a single cell line may translate into a highly useful antibody combination in vivo against certain types of cancers.

TABLE 8

Level of cancer cell growth inhibition by the 55 most efficacious mixtures of two or three anti-HER2 antibodies in the three cancer cell lines N87, BT474 and SKBR-3. The level of inhibition is shown as % metabolically active cells (% MAC).

| Mix No. | Antibodies | Level of inhibition (% MAC) | | | |
|---|---|---|---|---|---|
| | | N87 | BT474 | SKBR-3 | Average |
| 1 | 4380 + 4384 | 30 | 55 | 91 | 59 |
| 2 | 4382 + 4518 | 40 | 50 | 93 | 61 |
| 3 | 4381 + 4384 | 32 | 55 | 96 | 61 |
| 4 | 4384 + 4517 | 33 | 68 | 85 | 62 |
| 5 | 4385 + 4518 | 28 | 78 | 81 | 62 |
| 6 | 4382 + 4387 | 45 | 61 | 85 | 63 |
| 7 | 4383 + 4518 | 37 | 75 | 84 | 65 |
| 8 | 4380 + 4382 | 44 | 62 | 91 | 66 |
| 9 | 4382 + 4385 | 37 | 76 | 90 | 68 |
| 10 | 4381 + 4518 | 46 | 68 | 97 | 70 |
| 11 | 4380 + 4518 | 46 | 75 | 92 | 71 |
| 12 | 4385 + 4517 | 30 | 95 | 88 | 71 |
| 13 | 4384 + 4385 | 28 | 89 | 97 | 71 |
| 14 | 4381 + 4382 | 51 | 64 | 100 | 71 |
| 15 | 4380 + 4517 | 40 | 81 | 94 | 72 |
| 16 | 4383 + 4517 | 41 | 91 | 84 | 72 |
| 17 | 4381 + 4517 | 42 | 79 | 96 | 72 |
| 18 | 4383 + 4387 | 54 | 86 | 90 | 77 |
| 19 | 4383 + 4384 | 46 | 84 | 100 | 77 |
| 20 | 4384 + 4518 | 65 | 79 | 96 | 80 |
| 21 | 4381 + 4382 + 4518 | 25 | 34 | 69 | 43 |
| 22 | 4382 + 4385 + 4518 | 21 | 40 | 74 | 45 |
| 23 | 4380 + 4382 + 4518 | 29 | 35 | 72 | 45 |
| 24 | 4382 + 4387 + 4517 | 20 | 48 | 75 | 48 |
| 25 | 4382 + 4387 + 4518 | 30 | 43 | 74 | 49 |
| 26 | 4381 + 4382 + 4517 | 23 | 49 | 81 | 51 |
| 27 | 4380 + 4382 + 4517 | 30 | 47 | 82 | 53 |
| 28 | 4380 + 4381 + 4384 | 25 | 50 | 89 | 55 |
| 29 | 4380 + 4384 + 4517 | 28 | 43 | 94 | 55 |
| 30 | 4381 + 4384 + 4517 | 29 | 43 | 94 | 55 |
| 31 | 4383 + 4387 + 4517 | 29 | 61 | 76 | 55 |
| 32 | 4382 + 4518 + 4519 | 46 | 40 | 81 | 56 |
| 33 | 4380 + 4382 + 4519 | 41 | 47 | 80 | 56 |
| 34 | 4380 + 4384 + 4519 | 34 | 51 | 86 | 57 |
| 35 | 4383 + 4387 + 4518 | 24 | 66 | 83 | 58 |
| 36 | 4382 + 4383 + 4518 | 39 | 53 | 84 | 59 |
| 37 | 4382 + 4517 + 4518 | 39 | 46 | 93 | 59 |
| 38 | 4383 + 4385 + 4518 | 27 | 68 | 86 | 60 |
| 39 | 4381 + 4384 + 4519 | 41 | 52 | 91 | 61 |
| 40 | 4382 + 4385 + 4387 | 46 | 58 | 80 | 61 |
| 41 | 4380 + 4383 + 4518 | 42 | 61 | 81 | 61 |
| 42 | 4380 + 4381 + 4518 | 40 | 58 | 87 | 62 |
| 43 | 4381 + 4382 + 4387 | 47 | 56 | 82 | 62 |
| 44 | 4380 + 4383 + 4384 | 31 | 59 | 95 | 62 |
| 45 | 4380 + 4382 + 4387 | 46 | 59 | 81 | 62 |
| 46 | 4381 + 4382 + 4519 | 50 | 53 | 84 | 62 |
| 47 | 4380 + 4518 + 4519 | 40 | 56 | 91 | 62 |
| 48 | 4381 + 4517 + 4518 | 41 | 62 | 85 | 63 |
| 49 | 4382 + 4387 + 4519 | 51 | 57 | 80 | 63 |
| 50 | 4380 + 4382 + 4385 | 34 | 64 | 91 | 63 |
| 51 | 4380 + 4517 + 4518 | 40 | 60 | 89 | 63 |
| 52 | 4380 + 4384 + 4518 | 37 | 58 | 94 | 63 |
| 53 | 4383 + 4384 + 4517 | 35 | 60 | 94 | 63 |
| 54 | 4381 + 4383 + 4518 | 41 | 61 | 89 | 64 |
| 55 | 4381 + 4384 + 4518 | 37 | 59 | 95 | 64 |
| | Herceptin | 61 | 65 | 80 | 69 |

Example 5

ADCC and CDC Measurements

To investigate the ability of HER2-specific antibody mixtures of the invention to induce in vitro antibody dependent cellular cytotoxicity (ADCC) and complement dependent cytotoxicity (CDC), 20 different anti-HER2 antibody mixtures of two, three or four antibodies were tested using N87 and/or SKBR3 as target cells.

Methods

In Vitro ADCC

Peripheral blood mononuclear cells (PBMCs) were separated from the blood of normal volunteers using Lymphoprep™ separation medium and used as effector cells. HER2-expressing N87 and SKBR3 cells were used as target cells. Target cells were labeled with 334 µCi sodium chromate ($^{51}$Cr, 334) per $10^7$ cells for one hour at 37° C. After washing, the target cells ($5 \times 10^3$/well) were preincubated with anti-HER2 antibodies for 30 minutes at 37° C. in RPMI-1640+ 10% FCS+1% penicillin/streptomycin before adding the effector cells at a 50:1 effector:target (E/T) ratio. The cells were incubated for an additional 4 hours at 37° C. before detecting cell lysis by measuring the amount of $^{51}$Cr in the medium using a TopCount microplate scintillation counter. Maximum lysis was achieved by addition of 2% Triton-X100 to wells containing $^{51}$Cr labeled target cells. Spontaneous lysis was measured from wells containing both effector and target cells but no antibodies.

The specific cytotoxicity was calculated as follows:

$$\% \text{ specific cytotoxicity} = \frac{(\text{experimental target lysis} - \text{spontaneous target lysis})}{(\text{maximum target lysis} - \text{spontaneous target lysis})} \times 100$$

The relative cytotoxicity compared to the positive control antibody Herceptin was calculated as follows:

$$\% \text{ relative cytotoxicity} = (\% \text{ cytotoxicity antibody } X / \% \text{ cytotoxicity Herceptin}) \times 100$$

In Vitro CDC

Serum from freshly drawn blood separated by centrifugation was used as a source of complement. HER2-expressing N87 cells were used as target cells. Target cells were labeled with 334 µCi sodium chromate ($^{51}$Cr) per $10^7$ cells for one hour at 37° C. After washing, target cells ($5 \times 10^3$/well, 100 µl) were added to anti-HER2 antibodies diluted in RPMI-1640+ 10% FCS+1% penicillin/streptomycin (50 µl) followed by the addition of fresh serum (50 µl). The cells were incubated with serum and antibodies for 3 hours at 37° C. before detecting cell lysis by measuring the amount of $^{51}$Cr in the medium using a TopCount microplate scintillation counter. Maximum lysis was achieved by the addition of 2% Triton-X100 to wells containing $^{51}$Cr labeled target cells. Spontaneous lysis was measured from wells containing target cells but no serum.

The cytotoxicity percentage was calculated as follows $$\% \text{ cytotoxicity} = \frac{(\text{experimental target lysis} - \text{spontaneous target lysis})}{(\text{maximum target lyisis} - \text{spontaneous target lysis})} \times 100$$

Results

All of the 20 antibody combinations tested were able to induce ADCC in the HER2-expressing cell lines N87 and SKBR3. The maximum specific cytotoxicity of the anti-HER2 antibody combinations in the N87 cancer cell line was in the range from 16-24% at an antibody concentration of 0.1 µg/ml, which is equivalent to a % relative lysis of 46-69% compared to Herceptin (see FIGS. 2A and 2B, and FIGS. 3A and 3B). In SKBR3 cells the % specific ADCC induced at an antibody concentration of 0.1 µg/mL was in the range of 20-34%, corresponding to a relative cytotoxicity of 48-83% compared to Herceptin (see FIGS. 2C and 2D, and FIGS. 3C and 3D).

Figure 4:
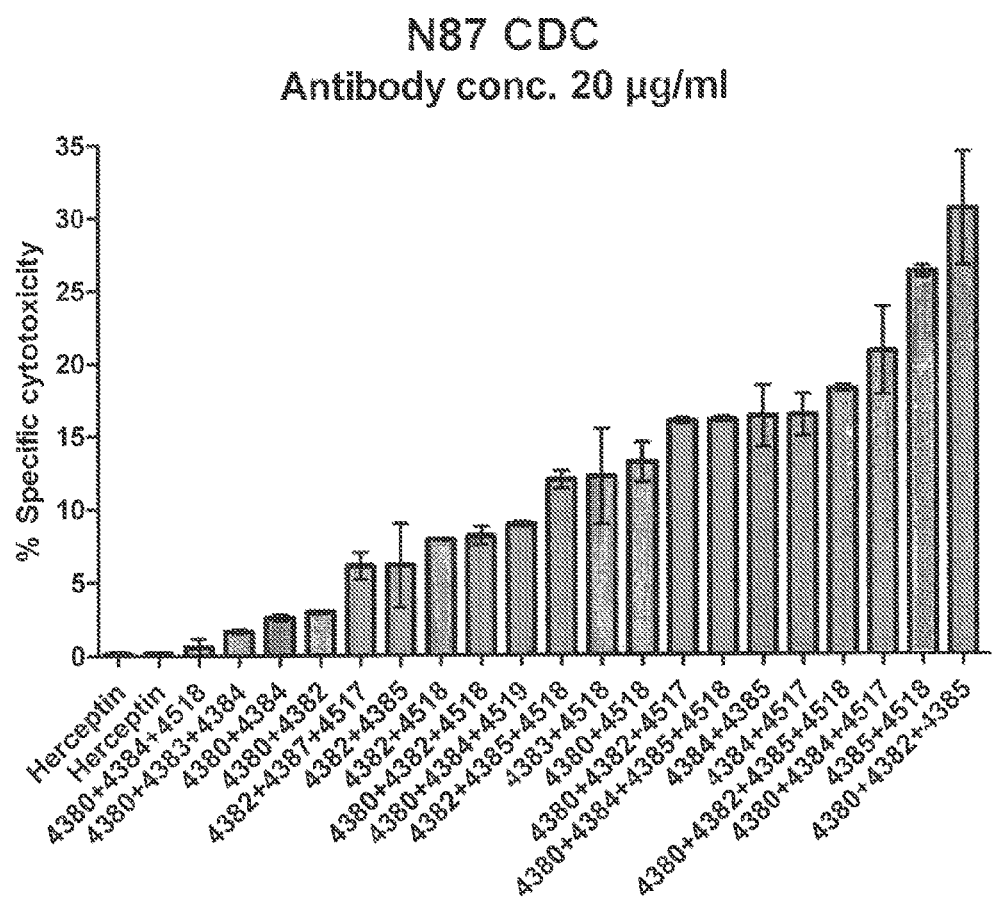
FIG. 4 shows measurements of CDC in N87 cells induced by antibody mixtures containing two, three or four anti-HER2 antibodies of the invention.
Figure 5:
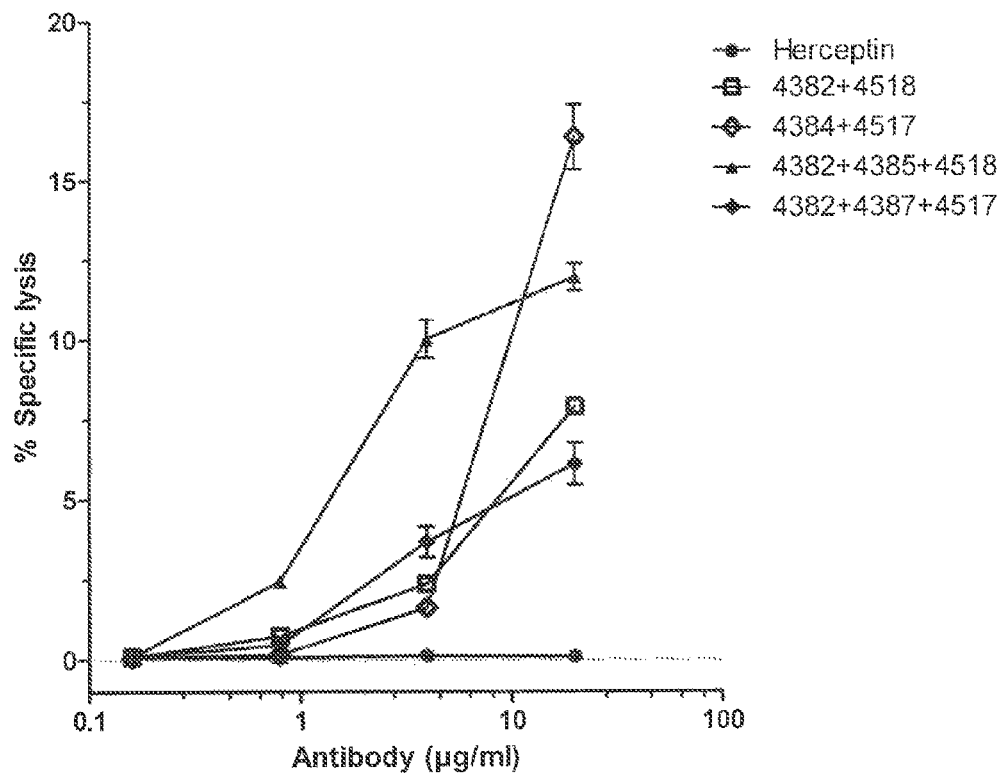
FIG. 5 shows measurements of CDC in N87 cells using mixtures of two or three anti-HER2 antibodies of the invention.
Figure 6:
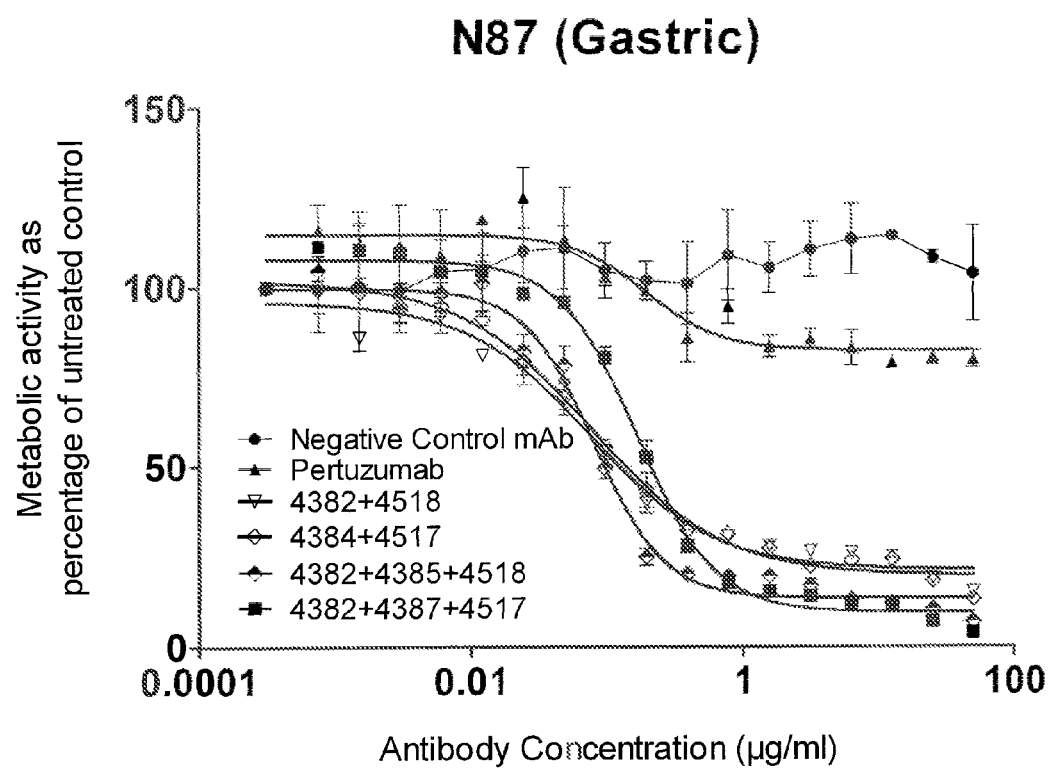
FIG. 6 shows the results of titrations of four different antibody mixtures of the invention on inhibition of metabolic activity of the N87 gastric cancer cell line.
Figure 7:
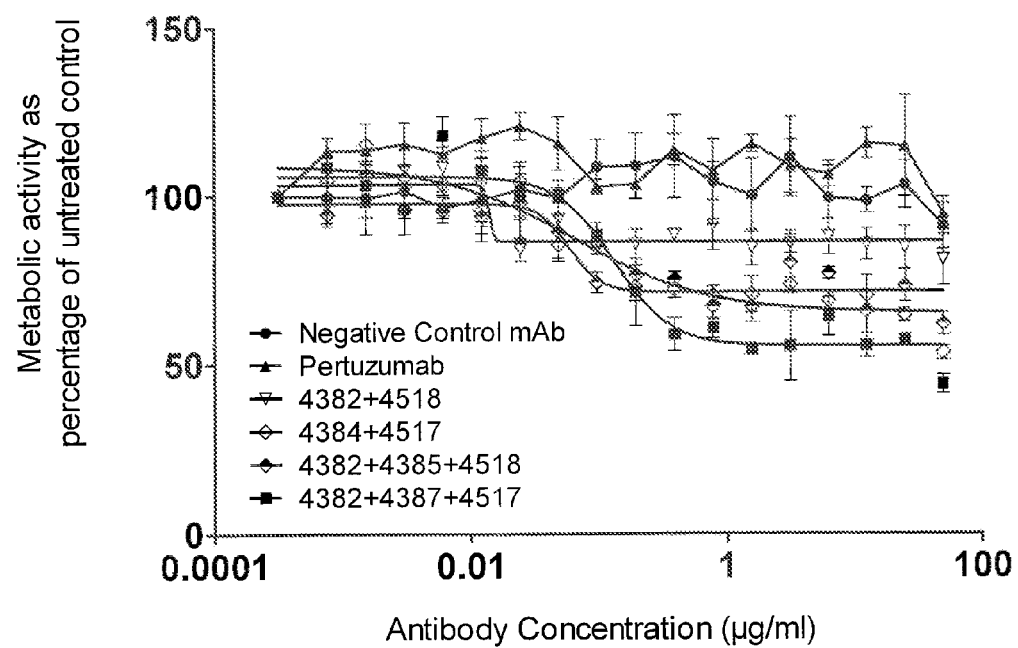
FIG. 7 shows the results of titrations of four different antibody mixtures of the invention on inhibition of metabolic activity of the HCC202 breast cancer cell line.
Figure 8:
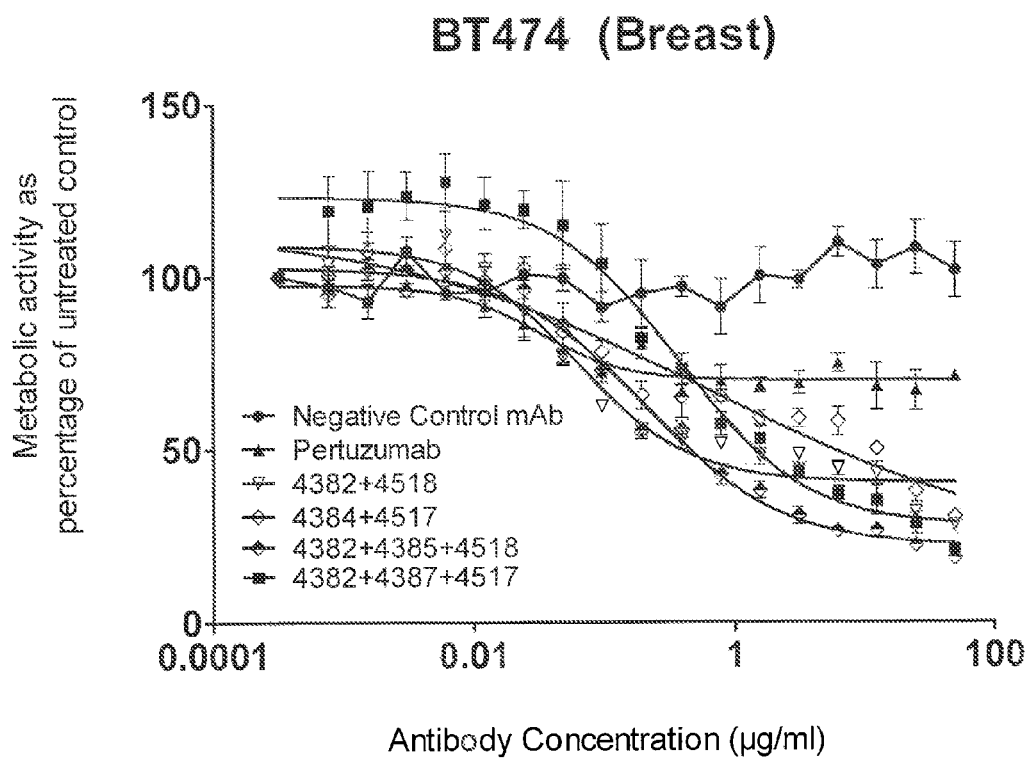
FIG. 8 shows the results of titrations of four different antibody mixtures of the invention on inhibition of metabolic activity of the BT474 breast cancer cell line.
Figure 9:
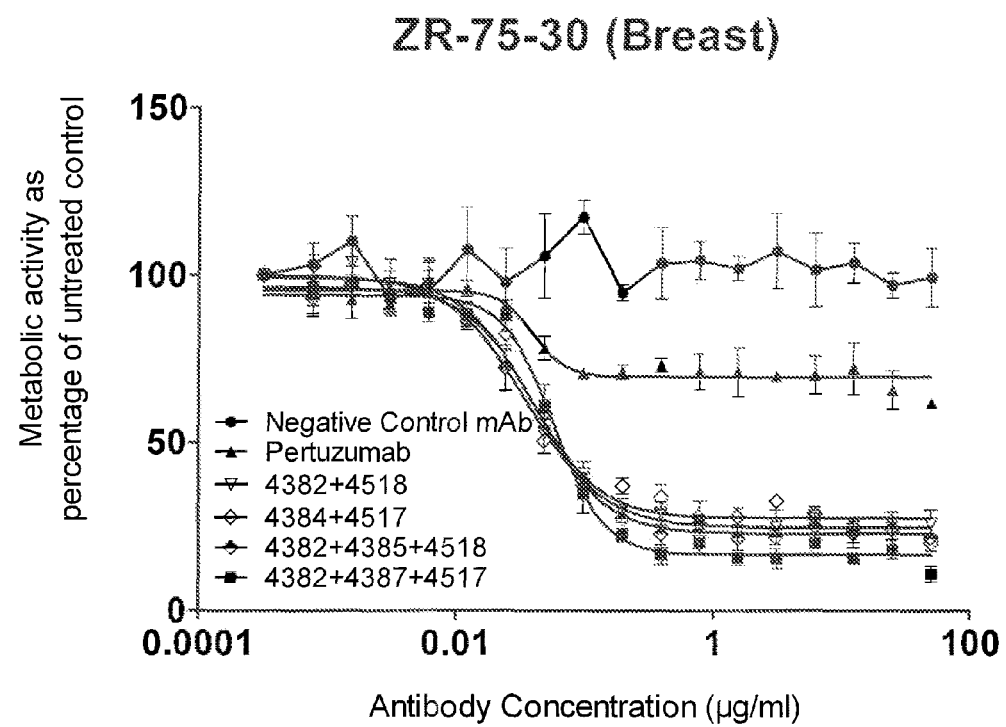
FIG. 9 shows the results of titrations of four different antibody mixtures of the invention on inhibition of metabolic activity of the ZR-75-30 breast cancer cell line.

As opposed to the results from the ADCC assay, where Herceptin induced potent lysis of target cells, Herceptin was unable to induce CDC (FIGS. 4 and 5). In contrast, sixteen of the anti-HER2 antibody mixtures of the invention containing two, three or four antibodies induced CDC at levels of 5%-31% specific cytotoxicity with a mean of 12% specific cytotoxicity (FIGS. 4 and 5). No CDC was observed when using SKBR3 cells. No correlation between the number of antibodies in the mixtures and the maximum % cytotoxicity induced was observed, and mixtures containing two, three and four antibodies were represented among the top four CDC-inducing antibody mixtures (FIGS. 4 and 5).

This example demonstrates that all of the anti-HER2 antibody mixtures of the invention exhibit substantial levels of ADCC and CDC. In an in vivo setting, mechanisms of action other than ADCC and CDC will play a significant role in the effect of the antibody mixtures. In particular, it is contemplated that the antibody mixtures of the invention that bind non-overlapping HER2 epitopes will result in a high level of receptor internalization, and that this will lead to an improved anti-tumor effect. The results shown in this example should thus be seen in conjunction with Example 4, which shows that the antibody mixtures of the invention generally show a high level of cancer cell growth inhibition in one or more of the tested cell lines, and that the growth inhibition shown in Example 4 is not necessarily correlated with e.g. the ADCC level.

Example 6

Titration of Antibody Mixtures on Different Cancer Cell Lines

In this example the WST-1 assay described in Examples 2 and 4 was used to measure the number of metabolically active cells after treatment with different antibody mixtures in different concentrations. The antibody mixtures were tested in several cancer cell lines, and the results for the four cell lines N87 (gastric cancer), HCC202 (breast cancer), BT474 (breast cancer) and ZR-75-30 (breast cancer) are presented in this example.

Methods

Prior to performing the WST-1 assay the antibody mixes of the invention along with control antibodies (Synagis® as a negative control antibody and a pertuzumab analogue as a positive control antibody) were diluted to a final total antibody concentration of 100 µg/ml in appropriate media for the individual cell lines supplemented with 2% FBS and 1% P/S, yielding a final antibody concentration of 50 µg/ml in wells containing the highest antibody concentration. A threefold serial dilution of the antibodies was then performed. Relevant numbers of cells (N87: 3000 cells/well; HCC202, BT474 and ZR-75-30: 2000 cells/well) were then added to the experimental wells in a 384-well plate, and the plates were incubated for 4 days in a humidified incubator at 37° C. WST-1 reagent was subsequently added to the plates, which were then incubated for one hour at 37° C. and then transferred to an orbital plate shaker for one hour. The absorbance was measured at 450 nm and 620 nm (reference wavelength) using an ELISA reader. The amount of metabolically active cells as a percentage of the untreated control (% MAC) was calculated as described above.

Results

The results of the titrations of four antibody mixtures on the cell lines N87, HCC202, BT474 and ZR-75-30 are shown in appended FIGS. 6-9. In addition, Table 9 below shows the $IC_{50}$ (half maximal inhibitory concentration) values as well as the maximum levels of inhibition of the four antibody mixtures and the pertuzumab analogue. (It should be noted that the $IC_{50}$ values can only be meaningfully compared if the corresponding maximum levels of inhibition are not too different from each other). It is evident from the figures as well as Table 9 that the mixtures have different levels of inhibition and different potencies depending on the cell line in which they are tested. However, all four mixtures are superior to a pertuzumab analogue at inhibiting the growth of the four cell lines.

TABLE 9

$IC_{50}$ values and efficacy of inhibition of the four cell lines by the four anti-HER2 mixtures and a pertuzumab analogue.

|  | N87 | | HCC202 | | BT474 | | ZR-75-30 | |
| --- | --- | --- | --- | --- | --- | --- | --- | --- |
|  | $IC_{50}$ | % inhibition | $IC_{50}$ | % inhibition | $IC_{50}$ | % inhibition | $IC_{50}$ | % inhibition |
| Pertuzumab | 0.196 | 17.7 | NA | 0.0 | 0.032 | 30.2 | 0.040 | 30.5 |
| 4382 + 4518 | 0.076 | 78.7 | 0.014 | 13.7 | 0.064 | 59.8 | 0.035 | 75.3 |
| 4384 + 4517 | 0.077 | 80.4 | 0.066 | 34.8 | 0.636 | 81.1 | 0.038 | 72.6 |
| 4382 + 4385 + 4518 | 0.080 | 86.6 | 0.060 | 28.6 | 0.211 | 78.2 | 0.043 | 77.1 |
| 4382 + 4387 + 4517 | 0.167 | 90.4 | 0.132 | 44.6 | 0.378 | 72.3 | 0.058 | 83.4 |

Example 7

In Vivo Efficacy of Anti-HER2 Mixtures, N87 Xenograft Model

The anti-HER2 antibody mixtures 4384+4517, 4382+4518, 4382+4385+4518 and 4382+4387+4518 were investigated for in vivo efficacy in the nude mouse NCI-N87 xenograft model. This is a widely used model for investigating the potency and efficacy of monoclonal anti-cancer antibodies, including anti-HER2 antibodies. Nude mice are immune-compromised and lack T-cells, which allows growth of human cells in the mice.

Method $10^7$ NCI-N87 cells were inoculated subcutaneously into the left flank of eight week old female athymic nude mice. Tumors were measured twice weekly with calipers and tumor volume in $mm^3$ was calculated according to the formula: $(width)^2 \times length \times 0.5$. At an average tumor size of 300 $mm^3$ the mice were randomized and treatment was initiated. The mice were treated twice weekly with intraperitoneal injections of 50 mg/kg 4384+4517, 4382+4318, 4382+4385+4518 or 4382+4387+4517 for five weeks (10 injections in total) followed by a three week observation period. The experiment also included the anti-HER2 monoclonal antibody trastuzumab (Herceptin®), which was dosed and administered following the same schedule as described for the anti-HER2 antibody mixtures.

Results

Figure 10:
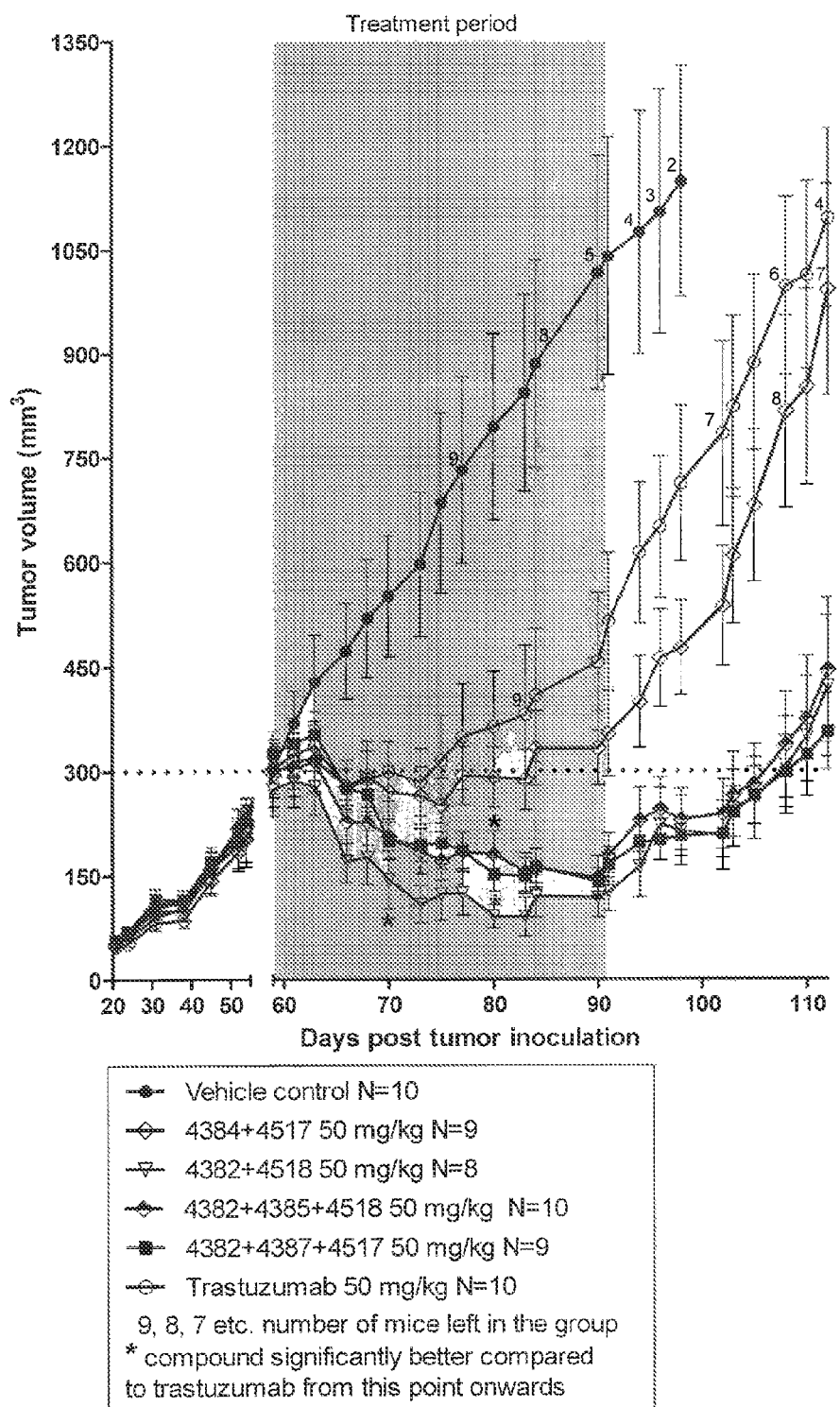
FIG. 10 shows the in vivo efficacy of anti-HER2 antibody mixtures of the invention in the nude mouse NCI-N87 gastric cancer xenograft model.

The results of this experiment are shown in FIG. 10. On day 59 post-tumor inoculation at an average tumor size of 300 $mm^3$ the mice were randomized into six groups of 10 animals and treatment was started with 50 mg/kg 4382+4518, 4384+ 4517, 4382+4385+4518, 4382+4387+4517, trastuzumab and vehicle (control group). Tumors in all treatment groups initially kept growing before starting to recede on day 66 after one week of treatment. In the mice treated with 4384+4517 or trastuzumab, the tumors became only marginally smaller than the treatment start size of 300 $mm^3$, before starting to grow at day 83 and 73 post-tumor inoculation, respectively. After this time the tumors on animals in both treatment groups had growth kinetics similar to the vehicle control group. In contrast, mice treated with 4382+4518, 4382+4385+4518 or 4382+4387+4517 showed prolonged and significantly better tumor suppression compared to trastuzumab. At the end of the treatment period (day 91) the tumor growth inhibition was reduced in all three groups, and the tumors slowly started to grow after treatment was discontinued.

In summary, animals treated with the anti-HER2 mixtures 4382+4518, 4382+4385+4518 and 4382+4387+4517 showed significantly improved growth inhibition of N87 tumor xenografts compared to trastuzumab.

Example 8

In Vivo Efficacy of Anti-HER2 Mixtures, OE19 Xenograft Model

The in vivo efficacy of the antibody mixtures 4384+4517, 4382+4518, 4382+4385+4518 and 4382+4387+4518 was tested in another in vivo tumor model, the OE19 gastric cancer xenograft model.

Method $5 \times 10^6$ OE19 cells were inoculated subcutaneously into the left flank of eight-ten week old female athymic nude mice. Tumors were measured twice weekly with calipers and tumor volume in $mm^3$ was calculated according to the formula: $(width)^2 \times length \times 0.5$. At an average tumor size of 110 $mm^3$ the mice were randomized and treatment was initiated. The mice were treated twice weekly with intraperitoneal injections of 50 mg/kg 4384+4517, 4382+4318, 4382+4385+4518 or 4382+4387+4517 for five weeks (10 injections in total) followed by a three week observation period. The experiment also included the anti-HER2 monoclonal antibody trastuzumab (Herceptin®), which was dosed and administered following the same schedule as described for the anti-HER2 antibody mixtures.

Results

Figure 11:
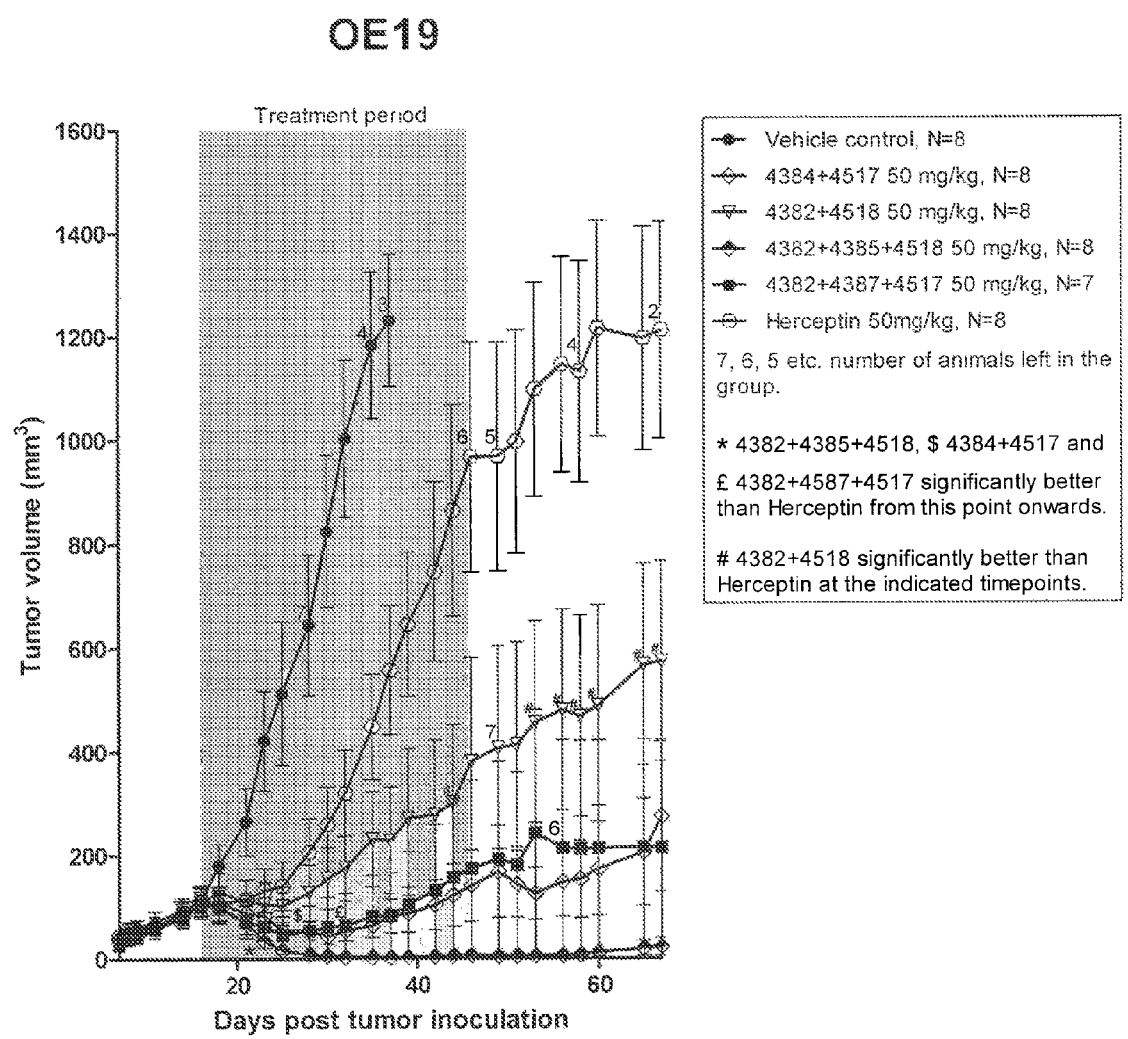
FIG. 11 shows the in vivo efficacy of anti-HER2 antibody mixtures of the invention in the nude mouse OE19 gastric cancer xenograft model.

The results of this experiment are shown in FIG. 11. Immediately after the first treatment a suppression of tumor growth compared to the control group could be observed in the groups treated with 4382+4385+4518 and 4382+4387+4517. The tumors on mice in the 4382+4385+4518 group all receded and were significantly better than trastuzumab as early as day 23; this improvement lasted throughout the rest of the study. On day 37 post-tumor inoculation, after 7 out of 10 treatments, 6 of the 8 mice in this group had total remission and were tumor-free until the end of the study. In the group treated with 4382+4387+4517, the tumors receded in all but one mouse. This antibody 3-mix was significantly better than trastuzumab from day 32 onwards. On day 37, 4 of the 7 animals in this group were tumor-free and remained so until the end of the study. One mouse did not respond to treatment and was euthanized on day 53 due to large tumor size. The mice treated with 4384+4517 also responded well to treatment and became significantly better than trastuzumab on day 28 post-tumor inoculation. On day 43, 3 of the 8 mice in this group were tumor-free. Mice treated with 4382+4518 had control of tumor growth from day 16 (treatment start) to day 28, after which antibody treatment still suppressed tumor growth compared to the vehicle control and trastuzumab, although the tumor size slowly increased. Despite this, 4382+4518 was significantly better at suppressing tumor growth compared to trastuzumab on day 44 and from day 53 until the end of the study (day 67).

In summary, all of the anti-HER2 antibody mixtures of the invention were significantly better at inhibiting and controlling tumor growth compared to trastuzumab in the OE19 tumor xenograft model.

Example 9

This example demonstrates that simultaneous HER2 degradation and blockade of HER2-mediated HER3 phosphorylation result in optimal inhibition of HER2-dependent cancer cell lines. Such a double blockade is best achieved with mixtures of three antibodies against HER2, two of which efficiently induce HER2 degradation, while the third antibody blocks compensatory signaling through the HER2/HER3 heterodimer. This compensatory HER2/HER3 heterodimer signaling is believed to be partly facilitated by compensatory HER3 upregulation (see Example 11).

Methods

In order to investigate the mechanism behind the superior growth inhibitory potential of antibody mixtures against HER2, the phosphorylation levels of EGFR, HER2 and HER3 were investigated in the gastric cancer cell line NCI-N87. Western blot analyses were performed on whole cell lysates of NCI-N87 cells pre-treated with the antibodies overnight and stimulated with 10 nM of the HER3 ligand heregulin beta for 15 minutes. Cells were grown in 6-well plates, and at 80% confluence the culture medium was removed, and the cells were washed in 1×PBS and treated with 10 µg/ml of the antibodies diluted in 2 ml medium containing 0.5% FBS. Cells were treated overnight and then stimulated with 10 nM of heregulin beta for 15 minutes. Cells were washed with 2 ml of 1×PBS after which 200 µl of 1×NuPAGE LDS Sample Buffer was added. 10-15 µl of sample were analyzed by western blotting using primary antibodies against EGFR, pEGFR (Tyr1068), HER2, pHER2 (Tyr1221), HER3 or pHER3 (Tyr1289).

Results

Figure 12:
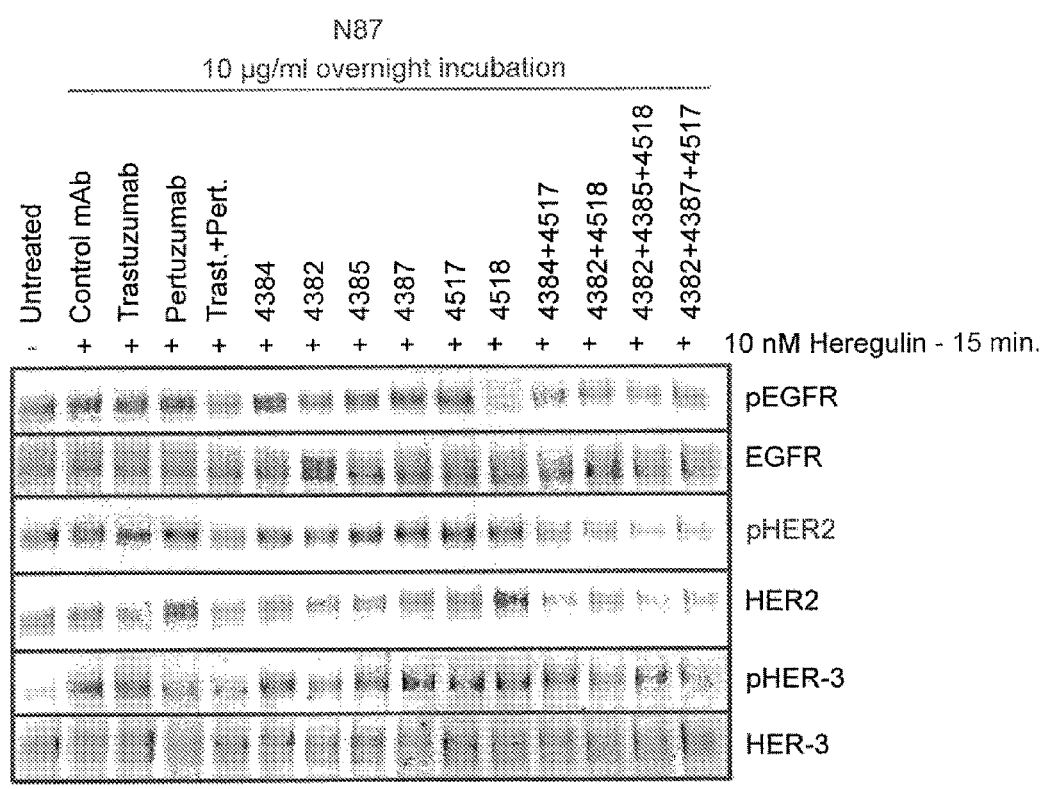
FIG. 12 shows western blot analyses of EGFR, pEGFR, HER2, pHER2, HER3 and pHER3 levels in the cell line NCI-N87 after overnight treatment with the indicated antibodies or antibody mixtures followed by stimulation with Heregulin beta for 15 minutes.

The results of the analyses of antibody-mediated inhibition of heregulin-induced phosphorylation of HER2, HER3 and EGFR (FIG. 12) demonstrate that anti-HER2 antibodies and antibody mixtures have different effects on the phosphorylation status of EGFR, HER2 and HER3 and the levels of HER2. Heregulin induced phosphorylation of HER3 but had no effect on the phosphorylation levels of EGFR and HER2. Only the monoclonal antibody 4382 and the reference monoclonal antibody pertuzumab analogue were able to block ligand-induced HER3 phosphorylation. These results show the ability of 4382 to block heterodimerization of HER2 and HER3. All antibody mixtures were able to decrease the overall level of HER2 and EGFR phosphorylation as well as HER2 levels. However, only mixtures containing 4382 were able to simultaneously induce HER2 degradation and inhibit HER2 and EGFR phosphorylation as well as HER3 phosphorylation. The results also showed that the mixtures containing three antibodies (4382+4385+4518 and 4382+4387+4517) were superior to the mixtures of two antibodies (4382+4518 and trastuzumab+pertuzumab analogue) at blocking phosphorylation of all three receptors, in particular HER2. It is believed that the mixtures containing three antibodies are superior because of their ability to simultaneously induce potent HER2 degradation (via the antibody pair 4385+4518 or 4387+4517 in the respective mixtures) and to block ligand-mediated HER3-phosphorylation (via antibody 4382). These results correlate well with our pharmacological data showing that mixtures of three antibodies against HER2 are superior to single anti-HER2 mAbs and are generally also superior to mixtures of two anti-HER2 antibodies at inhibiting cell and tumor growth in vitro and in vivo (see e.g. Examples 4 and 6).

Figure 13B:
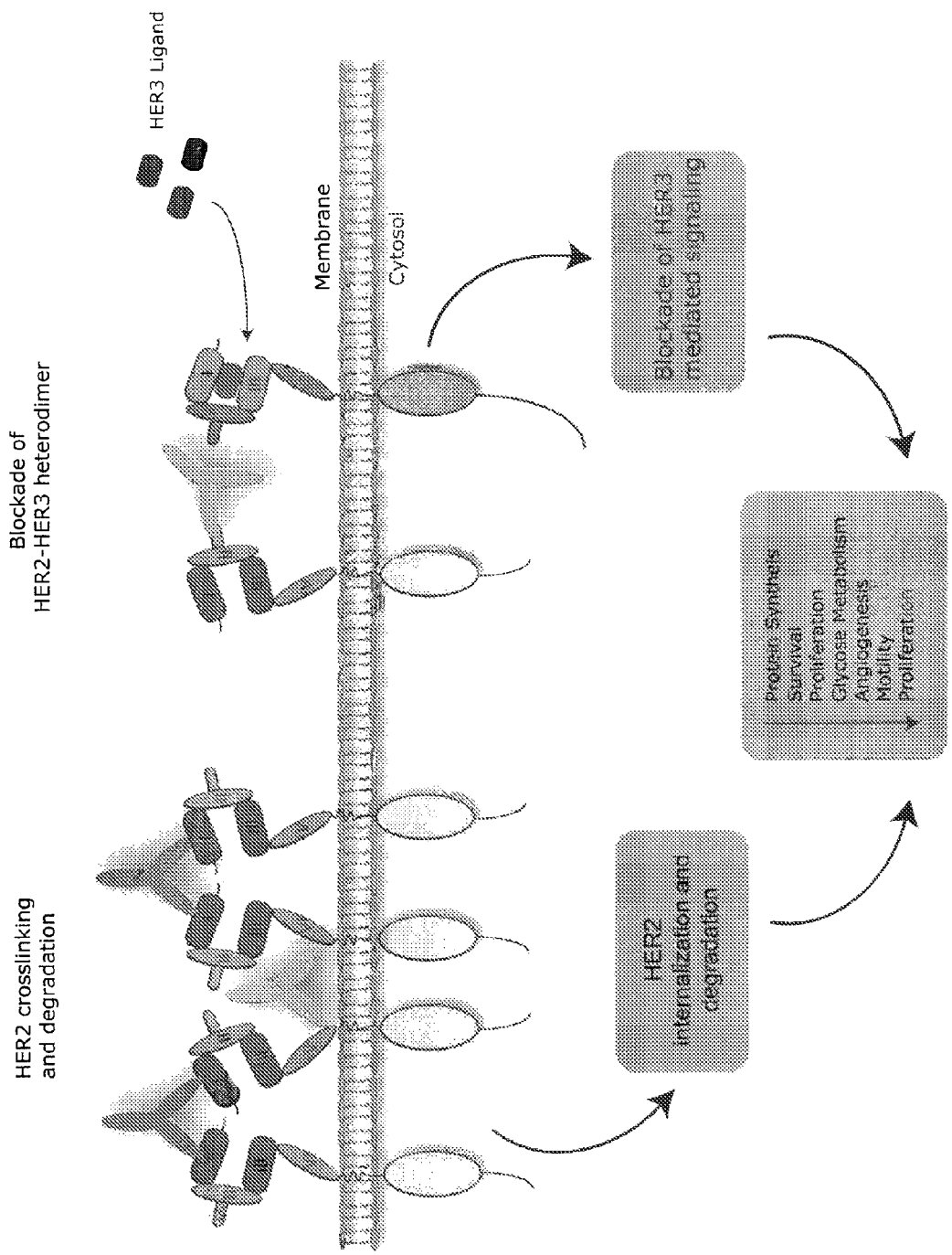
FIG. 13B illustrates a proposed mechanism for shutdown of both pathways by mixtures of three anti-HER2 antibodies of the invention, where two of the antibodies induce HER2 internalization and degradation, while the third antibody blocks compensatory signaling via HER2/HER3 heterodimers.

A schematic drawing of the HER2/HER3 signaling system and the hypothesized mechanism for the general superiority of 3-mixtures of anti-HER2 antibodies is shown in FIGS. 13 A and B, respectively. The left side of FIG. 13A illustrates the oncogenic signaling cascade by a HER2 homodimer, resulting in angiogenesis, cell motility and proliferation. The right side of FIG. 13A illustrates a signaling cascade (possibly caused by upregulation of HER3 upon treatment with an anti-HER2 antibody) by a HER2/HER3 heterodimer upon binding of HER3 ligand to the HER3 receptor. This results in oncogenic signaling by impacting mechanisms such as protein synthesis, proliferation and glycose metabolism. FIG. 13B illustrates a hypothesized mechanism by which mixtures of three anti-HER2 antibodies of the invention may obstruct oncogenic signaling from both HER2 homodimers and HER2/HER3 heterodimers. The left side of the figure shows that two anti-HER2 antibodies that bind non-overlapping epitopes of HER2 can form a cross-linked receptor-antibody lattice structure that leads to internalization and degradation of the HER2 receptor. The right side of FIG. 13B illustrates how a third anti-HER2 antibody that binds to the dimerization arm of HER2 is believed to be able to block compensatory formation of a HER2/HER3 heterodimer, thereby also blocking HER3 mediated signaling and hindering possible resistance to the anti-HER2 antibody treatment caused by upregulation of HER3.

Example 10

This example demonstrates that mixtures of anti-HER2 antibodies that bind non-overlapping epitopes are able to efficiently induce degradation of HER2 in various human cancer cell lines.

Methods

In order to investigate the level of receptor degradation induced by anti-HER2 mixtures, western blot analyses were performed on whole cell lysates of ZR-75-30, NCI-N87, BT474 and HCC202 cells treated with 10 µg/ml of antibodies for 48 hours. Cells were grown in T-75 culture flasks, and at 80% confluence the culture medium was removed, and the cells were washed in 1×PBS and treated with 20 µg/ml of the antibodies diluted in 5 ml medium containing 0.5% FBS. Cells were treated overnight, after which whole cell lysates were prepared using standard RIPA buffer. The total protein concentration was determined in each sample, and 1-5 µg protein was analyzed by western blotting using primary antibodies against HER2.

Results

Figure 14:
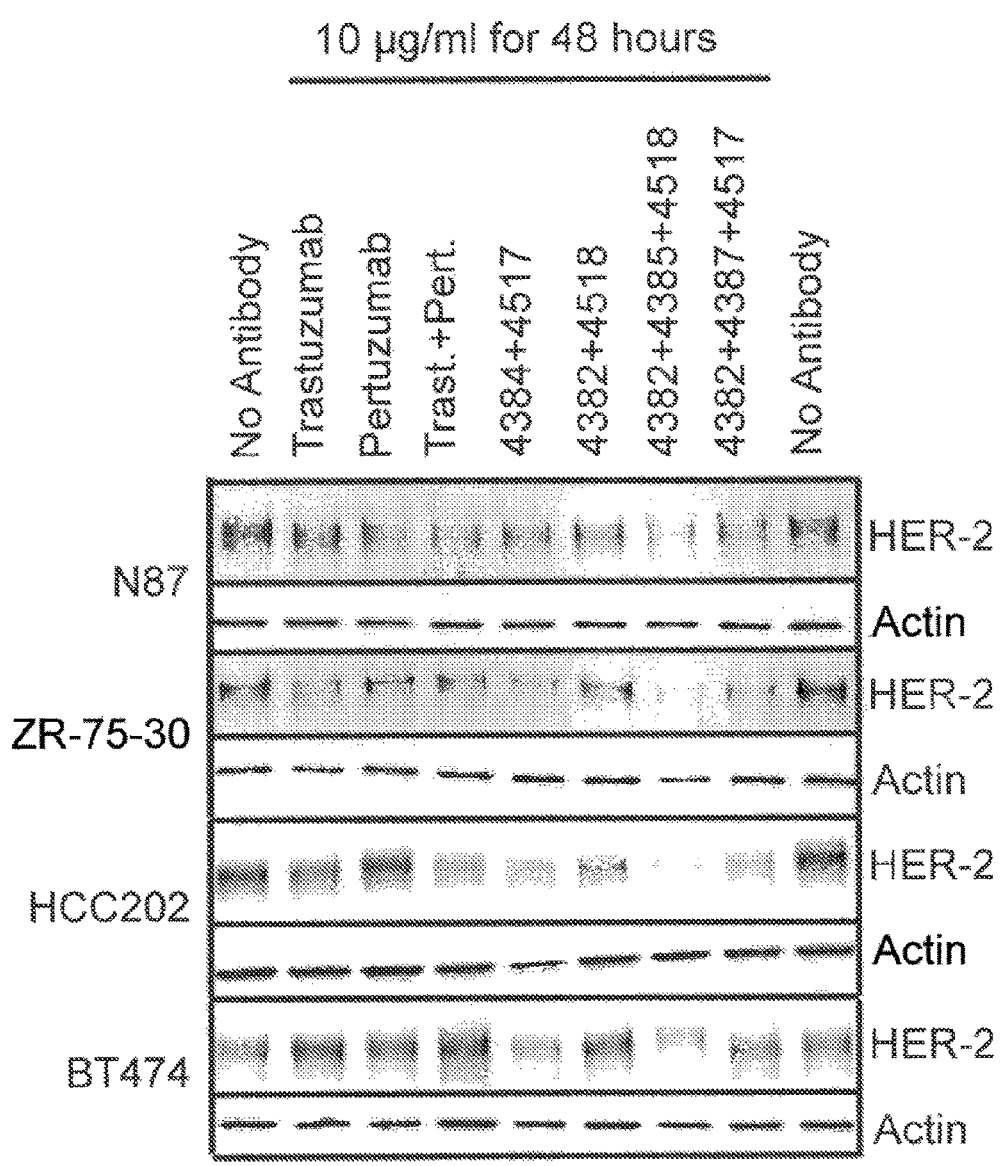
FIG. 14 shows western blot analyses of HER2 levels in the cancer cell lines ZR-75-30, NCI-N87, BT474 and HCC202 after overnight treatment with the indicated antibodies and antibody mixtures.

The results of the investigation of target degradation (FIG. 14) demonstrate that mixtures of antibodies that non-overlapping epitopes (4384+4517, 4382+4385+4518 and 4382+4387+4517) induced degradation of HER2 in all the cell lines. The mixtures 4382+4518 and trastuzumab+pertuzumab analogue were less efficient, indicating that the epitopes of these antibodies are not optimal for induction of target degradation. The mixtures of three antibodies appeared to be superior to both single anti-HER2 mAbs and mixtures of 2 anti-HER2 antibodies, and in particular the mixture containing antibodies 4382+4385+4518 was very efficient. Neither of the mAbs trastuzumab or pertuzumab analogue induced significant HER2 degradation, with the exception of trastuzumab in the ZR-75-30 cell line. These results thus show that mixtures of antibodies against non-overlapping epitopes on HER2 are able to induce its degradation but that the mixtures have different efficiencies.

Example 11

This example demonstrates that some cancer cell lines upregulate the levels of HER3 in response to HER2 targeting in order to maintain oncogenic signaling through the HER2/HER3 axis.

Methods

In order to investigate the level of HER3 levels in response to HER2 targeting western blot analyses were performed on whole cell lysates of NCI-N87 and HCC202 cells treated with 20 µg/ml of antibodies (trastuzumab, pertuzumab analogue, trastuzumab+pertuzumab analogue, 4384+4517, 4382+4518, 4382+4385+4518 or 4382+4387+4517) overnight. Cells were grown in T-75 culture flasks and at 80% confluence the culture medium was removed, and the cells were washed in 1×PBS and treated with 20 µg/ml of the antibodies diluted in 5 ml medium containing 0.5% FBS. Cells were treated overnight, after which whole cell lysates were prepared using standard RIPA buffer. The total protein concentration was determined in each sample, and 1 or 10 µg protein was analyzed by western blotting using primary antibodies against HER2 and HER3.

Results

Figure 15:
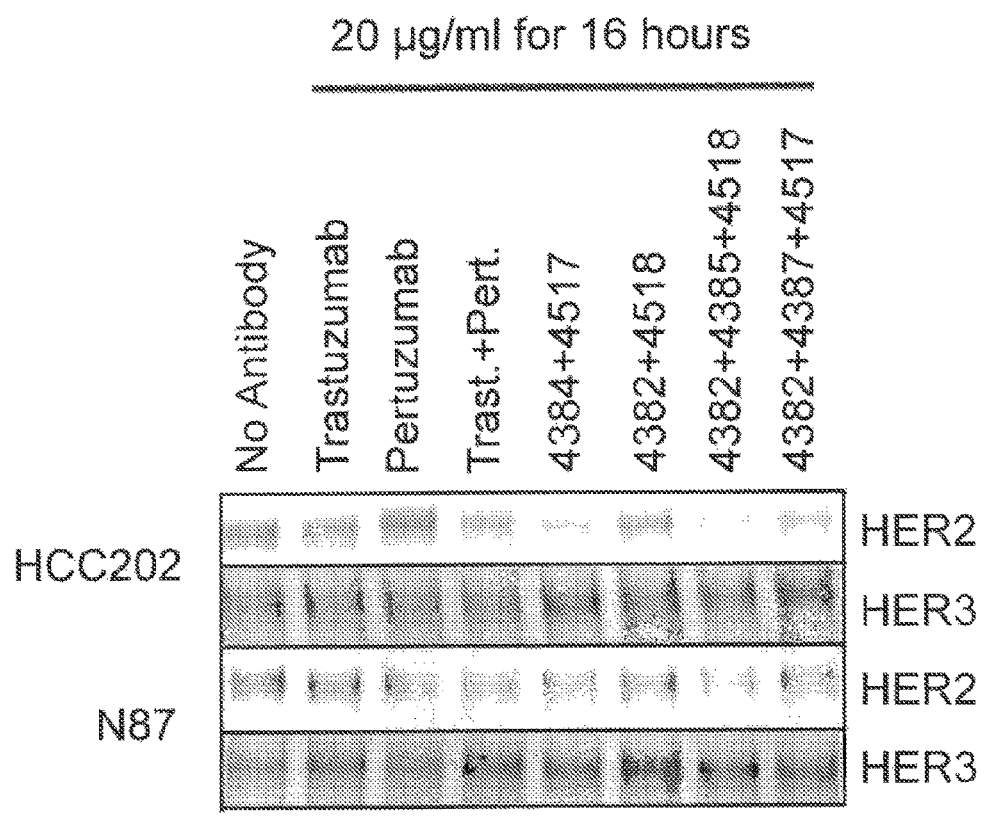
FIG. 15 shows western blot analyses of HER2 and HER3 levels in the cancer cell lines HCC202 and NCI-N87 after overnight treatment with the indicated antibodies and antibody mixtures.

The results of the investigation of HER3 levels (FIG. 15) demonstrate that HER2 targeting leads to HER3 upregulation in two different cell lines. The results also show that HER3 upregulation is most likely when the cells are treated with a mixture of antibodies that induces HER2 degradation.

Example 12

HER2 Degradation in Antibody-Treated Cancer Cell Lines

This example demonstrates that mixtures of HER2 antibodies that bind non-overlapping epitopes are able to induce degradation of HER2, that the combination of the three antibodies 4382+4385+4518 is more efficient at inducing degradation than combinations of two antibodies, and that the combination of antibodies 4385+4518 is the primary driver of HER2 internalization in the 4382+4385+4518 mixture.

Methods

In order to investigate the level of HER2 receptor degradation induced by antibody mixtures, western blot analyses were performed on whole cell lysates of OE19 (gastric cancer), NCI-N87 (gastric cancer), ZR-75-30 (breast cancer), BT474 (breast cancer) and HCC202 (breast cancer) cells treated with 10 µg/ml of a monoclonal antibody or an antibody mixture containing two or three antibodies for 48 hours. Cells were grown in T75 culture flasks. At 80% confluence the culture media was removed, and the cells were washed in 1×PBS and subsequently treated with 10 µg/ml antibody or antibody mixture diluted in 5 ml medium containing 0.5% FBS. Following 48 hours of incubation, whole cell lysates were prepared using RIPA buffer. The total protein concentration was determined for each sample and 1-5 µg protein was analyzed by western blotting using primary antibodies to HER2 and actin. The antibodies tested were a negative control antibody (anti-RSV (respiratory syncytial virus) antibody with no binding to HER2), trastuzumab, pertuzumab analog, trastuzumab+pertuzumab analogue, and antibodies 4382, 4385 and 4518 alone or in mixtures of two or three.

Results

Figure 16:
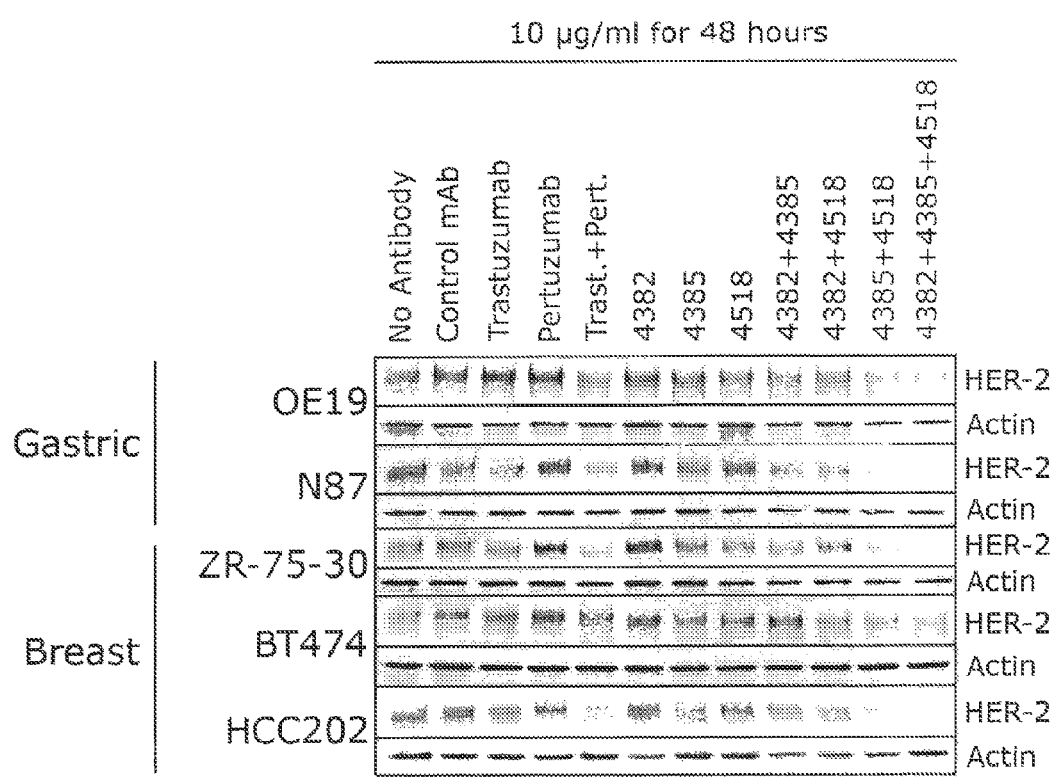
FIG. 16 shows a western blot analysis of HER2 levels in the cell lines OE19, N87, ZR-75-30, BT474 and HCC202 after incubation for 48 hours with 10 μg/ml of the indicated monoclonal antibodies or antibody mixtures.

The results (FIG. 16) show that of the tested monoclonal antibodies and antibody mixtures, the antibody mixture 4382+4385+4518 is the most efficient at inducing HER2 target degradation across all cell lines tested. In addition, 4385+4518 is the most efficient of the mixtures containing two antibodies at inducing HER2 degradation. The other two permutations of the antibodies in the 4382+4385+4518 antibody mixture, i.e. 4382+4385 and 4382+4518, are less efficient at inducing target internalization. This shows that the combination of antibodies 4385 and 4518 is the primary driver of HER2 internalization in the 4382+4385+4518 antibody mixture.

Example 13

Growth Inhibitory Effect of Different Components in an Antibody Mixture

In this example, the viability (WST-1) assay described in Examples 2, 4 and 6 was used to determine the anti-proliferative effect of the different components in the 4382+4385+4518 antibody mixture. In addition, antibody mixtures in which antibody 4382 was replaced by the pertuzumab analogue were similarly evaluated to determine whether antibodies with similar binding specificity and biological function can substitute for each other. As described in Example 3, antibody 4382 and the pertuzumab analogue bind to overlapping epitopes or epitopes in close proximity on HER2, and both antibodies are capable of blocking ligand-induced HER3 phosphorylation (Example 9). The antibody mixtures were tested in several cancer cell lines, including NCI-N87 (gastric cancer), OE19 (gastric cancer), HCC202 (breast cancer), BT474 (breast cancer) and SKBR3 (breast cancer).

Results

The results of the titration of the different antibody mixtures show that all combinations of two antibodies from the 4382+4385+4518 antibody mixture, i.e. 4382+4385, 4382+4518 and 4385+4518, are capable of inhibiting cancer cell growth. However, the mixture of all three of these antibodies, i.e. 4382+4385+4518, is the most efficient at inhibiting the growth in all cell lines tested. Results from the titrations on the three cell lines NCI-N87, BT474 and HCC202 are shown in FIGS. 17-19.

Figure 17:
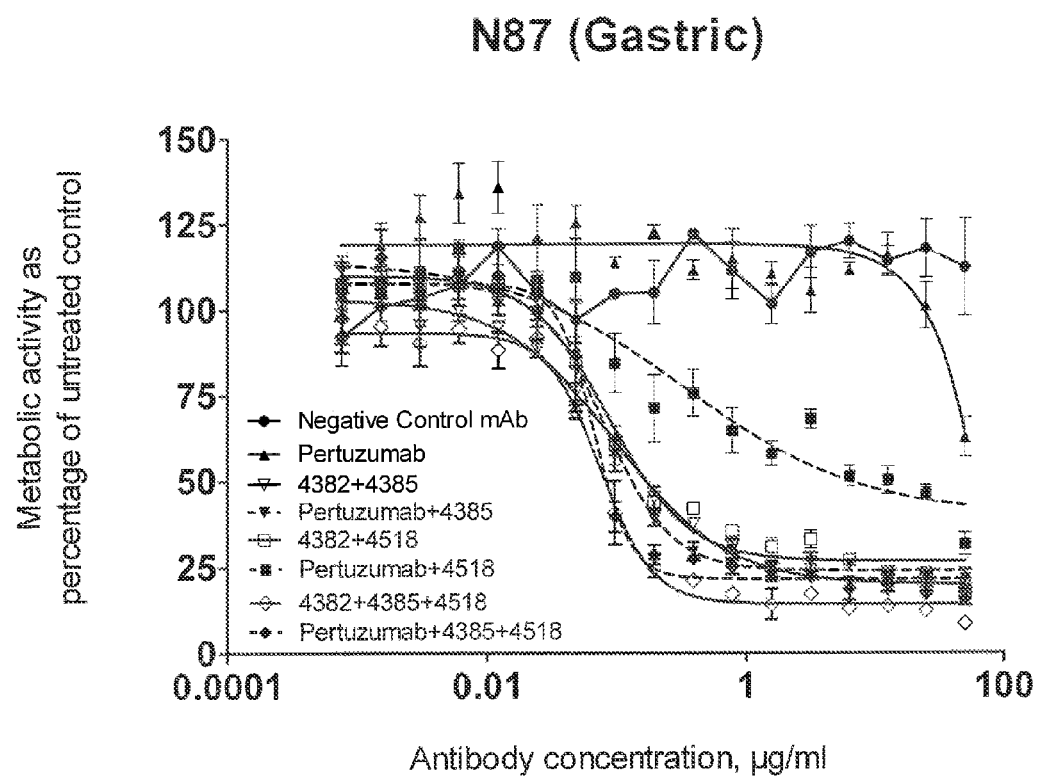
FIGS. 17-19 show the result of titrations of different antibody mixtures on inhibition of metabolic activity of the NCI-N87 gastric cancer cell line (FIG. 17), the BT474 breast cancer cell line (FIG. 18) and the HCC202 breast cancer cell line (FIG. 19).
Figure 18:
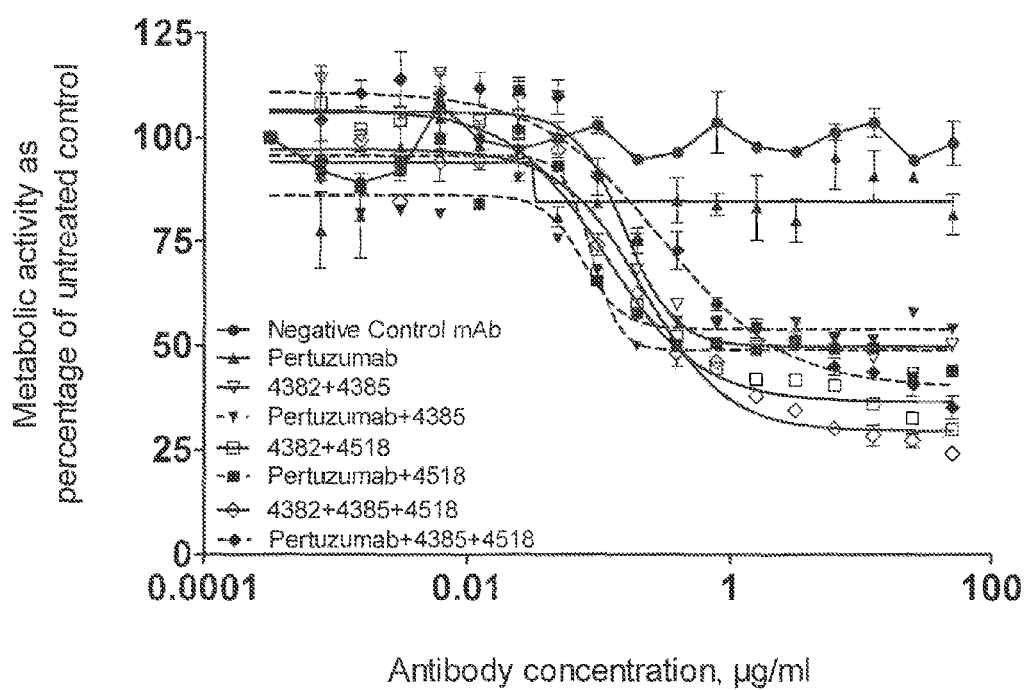
Figure 19:
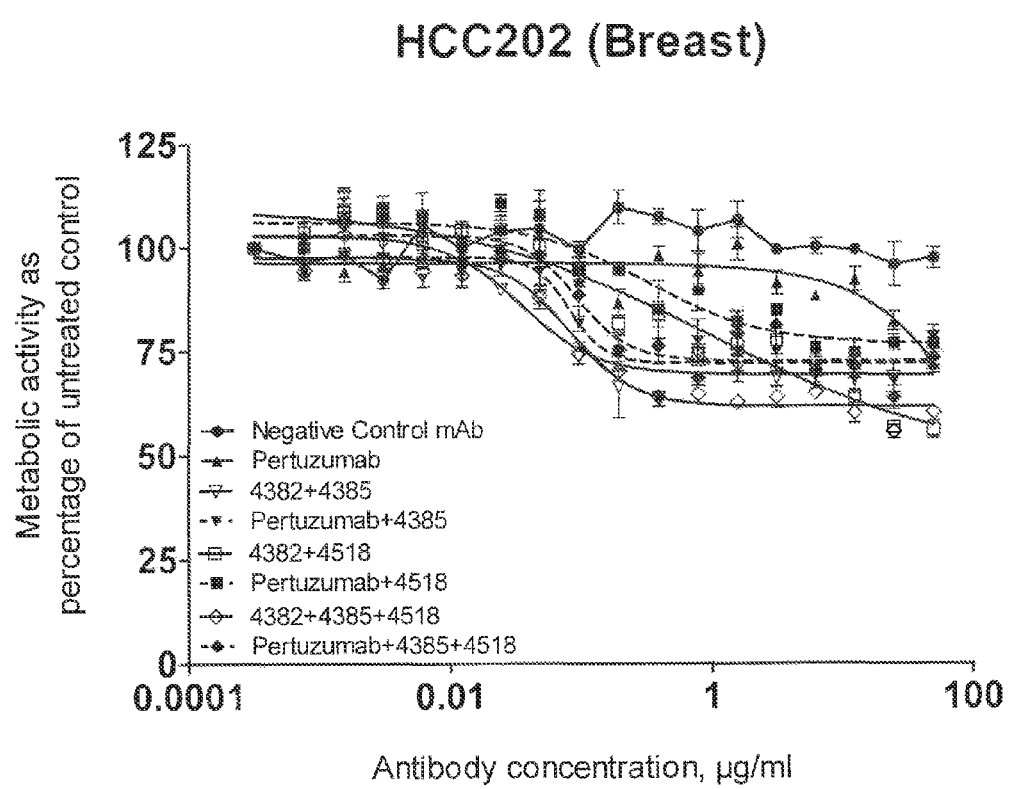

It may be seen from FIGS. 17-19 that the effect on growth inhibition is maintained when antibody 4382 is replaced by an antibody with similar binding specificity and the ability to block ligand-induced HER3 phosphorylation, in this case the pertuzumab analogue. Combinations of the pertuzumab analogue and antibody 4385 or 4518, or both, show enhanced inhibition of cell growth as compared to the pertuzumab analogue alone. However, combinations containing antibody 4382 are more efficacious than the corresponding combinations containing the pertuzumab analogue in all tested cell lines.

What is claimed is:

1. An antibody composition comprising
a first recombinant anti-HER2 antibody that comprises the CDR1, CDR2 and CDR3 of the heavy chain variable region in SEQ ID NO: 2 and the CDR1, CDR2 and CDR3 of the light chain variable region in SEQ ID NO: 4; and
a second recombinant anti-HER2 antibody that comprises the CDR1, CDR2 and CDR3 of the heavy chain variable region in SEQ ID NO: 22 and the CDR1, CDR2 and CDR3 of the light chain variable region in SEQ ID NO: 24.

2. An antibody composition comprising at least first and second recombinant anti-HER2 antibodies that bind distinct epitopes of HER2, wherein each of said first and second antibodies binds to the same epitope as and competes for binding with the following antibodies, respectively:
a) an anti-HER2 antibody that comprises the CDR1, CDR2 and CDR3 of the heavy chain variable region in SEQ ID NO: 2 and the CDR1, CDR2 and CDR3 of the light chain variable region in SEQ ID NO: 4; and
b) an anti-HER2 antibody that comprises the CDR1, CDR2 and CDR3 of the heavy chain variable region in SEQ ID NO: 22 and the CDR1, CDR2 and CDR3 of the light chain variable region in SEQ ID NO: 24.

3. The antibody composition of claim 1 or 2, wherein at least one recombinant anti-HER2 antibody in said composition is an immunoconjugate comprising a recombinant anti-HER2 antibody conjugated to an anti-cancer agent.

4. The antibody composition of claim 3, wherein the anti-cancer agent is selected from the group consisting of cytotoxic agents, cytokines, toxins and radionuclides.

5. The antibody composition of claim 1, wherein the first recombinant anti-HER2 antibody comprises the heavy chain variable region in SEQ ID NO: 2 and the light chain variable region in SEQ ID NO: 4; and the second recombinant anti-HER2 antibody comprises the heavy chain variable region in SEQ ID NO: 22 and the light chain variable region in SEQ ID NO: 24.

6. The antibody composition of claim 1, wherein the first or the second recombinant anti-HER2 antibody, or both, are an IgG isotype.

7. The antibody composition of claim 1 or 2, wherein the first or the second recombinant anti-HER2 antibody, or both, are humanized.

8. A method for treating cancer in a human or other mammal, the method comprising administering to said mammal an recombinant anti-HER2 antibody composition according to claim 1 or 2.

9. A method for treating a patient with a disorder characterized by overexpression of HER2, the method comprising administering to said patient an anti-HER2 antibody composition according to claim 1 or 2.

10. A method for reducing heterodimer formation between HER2 and other ErbB family receptors in cells that overexpress HER2, the method comprising contacting said cells with an anti-HER2 antibody composition according to claim 1 or 2.

11. A method for inducing internalization of HER2 on the surface of cells that overexpress HER2, the method comprising contacting the cells with an anti-HER2 antibody composition according to claim 1 or 2.

12. A method for inhibiting growth of tumor cells that are resistant or partially resistant to treatment with a recombinant anti-HER2 antibody, the method comprising contacting the cells with an anti-HER2 antibody composition according to claim 1 or 2.

13. The method of claim 12, where the tumor cells have been previously treated with trastuzumab.

* * * * *

UNITED STATES PATENT AND TRADEMARK OFFICE
CERTIFICATE OF CORRECTION

PATENT NO. : 8,609,095 B2  
APPLICATION NO. : 13/040029  
DATED : December 17, 2013  
INVENTOR(S) : Pedersen et al.

Page 1 of 1

It is certified that error appears in the above-identified patent and that said Letters Patent is hereby corrected as shown below:

IN THE CLAIMS:

Column 142, line 46, claim 8: delete "recombinant"

Signed and Sealed this
Sixth Day of May, 2014

Michelle K. Lee
*Deputy Director of the United States Patent and Trademark Office*

SEQUENCE LISTING

<160> NUMBER OF SEQ ID NOS: 116

<210> SEQ ID NO 1
<211> LENGTH: 360
<212> TYPE: DNA
<213> ORGANISM: Artificial Sequence
<220> FEATURE:
<223> OTHER INFORMATION: Ab 4517 VH coding sequence

<400> SEQUENCE: 1

```
gaagtgcagc tggtggaatc tggcggcgac ctggtgaaac ctggcggctc cctgaagctg      60
tcctgcgccg cctccggctt caccttctcc agctacggca tgtcctgggt gcgactgacc     120
cccgacaagc ggctgaatg gtggcaacc atctccggcg gaggtcccta cacctactac      180
cccgactccg tgaagggccg gttcaccatc tcccgggata tcgccaagtc caccctgtac     240
ctgcagatgt cctccctgaa gtccgaggac accgccgtgt actactgcgc cggaagggc      300 aactacggca attacggcaa gctggcctac tggggccagg gcacctccgt gacagtctcg     360
```

<210> SEQ ID NO 2
<211> LENGTH: 120
<212> TYPE: PRT
<213> ORGANISM: Mus musculus
<220> FEATURE:
<221> NAME/KEY: MISC_FEATURE
<223> OTHER INFORMATION: Ab 4517 VH

<400> SEQUENCE: 2

```
Glu Val Gln Leu Val Glu Ser Gly Gly Asp Leu Val Lys Pro Gly Gly
 1               5                  10                  15

Ser Leu Lys Leu Ser Cys Ala Ala Ser Gly Phe Thr Phe Ser Ser Tyr
            20                  25                  30

Gly Met Ser Trp Val Arg Leu Thr Pro Asp Lys Arg Leu Glu Trp Val
        35                  40                  45

Ala Thr Ile Ser Gly Gly Gly Ser Tyr Thr Tyr Tyr Pro Asp Ser Val
    50                  55                  60

Lys Gly Arg Phe Thr Ile Ser Arg Asp Ile Ala Lys Ser Thr Leu Tyr
65                  70                  75                  80

Leu Gln Met Ser Ser Leu Lys Ser Glu Asp Thr Ala Val Tyr Tyr Cys
                85                  90                  95

Ala Arg Lys Gly Asn Tyr Gly Asn Tyr Gly Lys Leu Ala Tyr Trp Gly
            100                 105                 110

Gln Gly Thr Ser Val Thr Val Ser
        115                 120
```

<210> SEQ ID NO 3
<211> LENGTH: 642
<212> TYPE: DNA
<213> ORGANISM: Artificial Sequence
<220> FEATURE:
<223> OTHER INFORMATION: Ab 4517 LC coding sequence

<400> SEQUENCE: 3

```
gatatccaga tgacccagtc ccccgcctcc ctgtccgtgt ctgtgggcga gacagtgacc      60
atcacctgtc gggcctccga gaacatctac tccaacctgg cctggtatca gcaggaacag     120
ggcaagtccc cccagctgct ggtgtacgcc gccaccaatc tggccgacgg cgtgccctcc     180
agattctccg gctctggctc cggcacccag tactcccctga agatcaactc cctgcagtcc    240
gaggacttcg gctcctacta ctgccagcac ttctggggca cccctggac cttcggcgga      300
```

```
ggcaccaagc tggaaatcaa gcggaccgtg gccgctccct ccgtgttcat cttcccaccc      360
tccgacgagc agctgaagtc cggcaccgcc tccgtggtgt gcctgctgaa caacttctac      420
ccccgcgagg ccaaggtgca gtggaaggtg gacaacgccc tgcagagcgg caactcccag      480
gaatccgtga ccgagcagga ctccaaggac agcacctact ccctgtcctc caccctgacc      540
ctgtccaagg ccgactacga aagcacaag gtgtacgcct gcgaagtgac ccaccagggc      600
ctgtccagcc ccgtgaccaa gtccttcaac cggggcgagt gc                        642
```

<210> SEQ ID NO 4
<211> LENGTH: 214
<212> TYPE: PRT
<213> ORGANISM: Mus musculus
<220> FEATURE:
<221> NAME/KEY: MISC_FEATURE
<223> OTHER INFORMATION: Ab 4517 LC

<400> SEQUENCE: 4

```
Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Glu Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 5
<211> LENGTH: 345
<212> TYPE: DNA
<213> ORGANISM: Artificial Sequence
<220> FEATURE:
<223> OTHER INFORMATION: Ab 4518 VH coding sequence

<400> SEQUENCE: 5

```
gaagtgcagc tgcagcagtc tggcgccgac ctggtgaaac tggcgcctc cgtgaagctg       60 tcctgcacca cctccggctt caacatcaag gacatcttca ccactgggt gaaagagcgg      120
```

```
cccgagcagg gcctggaatg gatcggacgg atcgaccccg ccaacgacaa ccctaagtac      180
gaccccaagt tccagggcaa ggccaccatc tccgccgaca cctccagcaa caccgcctac      240
ctgcggctgt cctccctgac ctctgaggac accgccgtgt actactgcgc tggcggccct      300
gcctacttcg actattgggg ccagggcacc accctgacag tctcg                     345
```

```
<210> SEQ ID NO 6
<211> LENGTH: 115
<212> TYPE: PRT
<213> ORGANISM: Mus musculus
<220> FEATURE:
<221> NAME/KEY: MISC_FEATURE
<223> OTHER INFORMATION: Ab 4518 VH

<400> SEQUENCE: 6
```

```
Glu Val Gln Leu Gln Gln Ser Gly Ala Asp Leu Val Lys Pro Gly Ala
1               5                   10                  15

Ser Val Lys Leu Ser Cys Thr Thr Ser Gly Phe Asn Ile Lys Asp Ile
            20                  25                  30

Phe Ile His Trp Val Lys Glu Arg Pro Glu Gln Gly Leu Glu Trp Ile
        35                  40                  45

Gly Arg Ile Asp Pro Ala Asn Asp Asn Pro Lys Tyr Asp Pro Lys Phe
    50                  55                  60

Gln Gly Lys Ala Thr Ile Ser Ala Asp Thr Ser Ser Asn Thr Ala Tyr
65                  70                  75                  80

Leu Arg Leu Ser Ser Leu Thr Ser Glu Asp Thr Ala Val Tyr Tyr Cys
                85                  90                  95

Ala Gly Gly Pro Ala Tyr Phe Asp Tyr Trp Gly Gln Gly Thr Thr Leu
            100                 105                 110

Thr Val Ser
        115
```

```
<210> SEQ ID NO 7
<211> LENGTH: 642
<212> TYPE: DNA
<213> ORGANISM: Artificial Sequence
<220> FEATURE:
<223> OTHER INFORMATION: Ab 4518 LC coding sequence

<400> SEQUENCE: 7
gatatcgtga tgacccagtc ccacaagttc atgtccacct ccgtgggcga ccgggtgtcc       60
atctcctgca aggcctccca ggacgtgatc gccgccgtga cctggtatca gcagaagccc      120
ggccagtccc ccaagctgct gatctactgg gcctccaccc ggcacaccgg cgtgccagac      180
agattcaccg gctccggcag cggcaccgac tacaccctga ccatctccag catgcaggcc      240
gaggacctgg ccctgtacta ctgccagcag cactactcca ccccctggac cttcggcgga      300
ggcaccaagc tggaaatcaa gcggaccgtg gccgctccct ccgtgttcat cttcccaccc      360
tccgacgagc agctgaagtc cggcaccgcc tccgtggtgt gcctgctgaa caacttctac      420
ccccgcgagg ccaaggtgca gtggaaggtg gacaacgccc tgcagtccgg caactcccag      480
gaatccgtga ccgagcagga ctccaaggac agcacctact ccctgtcctc cacectgacc      540 ctgtccaagg ccgactacga gaagcacaag gtgtacgcct gcgaagtgac ccaccagggc      600
ctgtccagcc ccgtgaccaa gtccttcaac cggggcgagt gc                         642
```

```
<210> SEQ ID NO 8
<211> LENGTH: 214
<212> TYPE: PRT
<213> ORGANISM: Mus musculus
```

-continued

```
<220> FEATURE:
<221> NAME/KEY: MISC_FEATURE
<223> OTHER INFORMATION: Ab 4518 LC

<400> SEQUENCE: 8

Asp Ile Val Met Thr Gln Ser His Lys Phe Met Ser Thr Ser Val Gly
1               5                   10                  15

Asp Arg Val Ser Ile Ser Cys Lys Ala Ser Gln Asp Val Ile Ala Ala
            20                  25                  30

Val Thr Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
50                  55                  60

Ser Gly Ser Gly Thr Asp Tyr Thr Leu Thr Ile Ser Ser Met Gln Ala
65                  70                  75                  80

Glu Asp Leu Ala Leu Tyr Tyr Cys Gln Gln His Tyr Ser Thr Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 9
<211> LENGTH: 351
<212> TYPE: DNA
<213> ORGANISM: Artificial Sequence
<220> FEATURE:
<223> OTHER INFORMATION: Ab 4380/4381 VH coding sequence

<400> SEQUENCE: 9
caggtgcagc tgcagcagtc tggcgccgag ctggtgaaac ctggcgcctc cgtgaaggtg      60
tcctgcaccg cctccggcta caccttcacc aactactgga tccactgggt gaaacagcgg     120
cctggacagg gcctggaatg gatcggacgg atccacccct ccgactccga cgtgcactac     180
aaccagcggt tccgggacaa gaccaccctg accgtggacc ggtcctcctc caccgcctac     240
atgcagctgt cctccctgac ctccgaggac tccgccgtgt actactgcgc caagtcctac     300
tacgacagcg ccatggacta ctggggccag ggcacctccg tgaccgtctc g              351

<210> SEQ ID NO 10
<211> LENGTH: 117
<212> TYPE: PRT
<213> ORGANISM: Mus musculus
<220> FEATURE:
<221> NAME/KEY: MISC_FEATURE
<223> OTHER INFORMATION: Ab 4380/4381 VH

<400> SEQUENCE: 10
```

Gln Val Gln Leu Gln Gln Ser Gly Ala Glu Leu Val Lys Pro Gly Ala
1               5                   10                  15

Ser Val Lys Val Ser Cys Thr Ala Ser Gly Tyr Thr Phe Thr Asn Tyr
            20                  25                  30

Trp Ile His Trp Val Lys Gln Arg Pro Gly Gln Gly Leu Glu Trp Ile
            35                  40                  45

Gly Arg Ile His Pro Ser Asp Ser Asp Val His Tyr Asn Gln Arg Phe
50                  55                  60

Arg Asp Lys Thr Thr Leu Thr Val Asp Arg Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Lys Ser Tyr Tyr Asp Ser Ala Met Asp Tyr Trp Gly Gln Gly Thr
                100                 105                 110

Ser Val Thr Val Ser
        115

<210> SEQ ID NO 11
<211> LENGTH: 654
<212> TYPE: DNA
<213> ORGANISM: Artificial Sequence
<220> FEATURE:
<223> OTHER INFORMATION: Ab 4380/4381 LC coding sequence
<220> FEATURE:
<221> NAME/KEY: misc_feature
<222> LOCATION: (118)..(120)
<223> OTHER INFORMATION: nnn is acc or tat

<400> SEQUENCE: 11
gatatcgtgc tgacccagtc ccccgcctcc ctggctgtgt ctctgggcca gcgggccacc      60
atctcttgcc gggcctccaa gtccgtgacc acctccggct actcctacat gcactggnnn     120
cagcagaagc ccggccagcc ccccaagctg ctgatctccg tggcctccaa cctggaatcc     180
ggcgtgcccg ccagattctc cggctctggc tccggcaccg acttcaccct gaacatccac     240
cccgtggaag aagaggacgc cgccaccttc tactgccacc actccagaga gctgccctgg     300
accttcggcg gaggcaccaa gctggaaatc aagcggaccg tggccgctcc ctccgtgttc     360
atcttcccac cctccgacga gcagctgaag tccggcaccg cctccgtggt gtgcctgctg     420
aacaacttct accccgcga ggccaaggtg cagtggaagg tggacaacgc cctgcagtcc      480
ggcaactccc aggaatccgt gaccgagcag gactccaagg acagcaccta ctccctgtcc     540
tccaccctga ccctgtccaa ggccgactac gagaagcaca aggtgtacgc ctgcgaagtg     600
acccaccagg gcctgtccag ccccgtgacc aagtccttca ccggggcga gtgc            654

<210> SEQ ID NO 12
<211> LENGTH: 218
<212> TYPE: PRT
<213> ORGANISM: Mus musculus
<220> FEATURE:
<221> NAME/KEY: MISC_FEATURE
<223> OTHER INFORMATION: Ab 4380/4381 LC
<220> FEATURE:
<221> NAME/KEY: MISC_FEATURE
<222> LOCATION: (40)..(40)
<223> OTHER INFORMATION: Xaa is Tyr or Thr

<400> SEQUENCE: 12

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Thr Thr Ser

```
                20                  25                  30
Gly Tyr Ser Tyr Met His Trp Xaa Gln Gln Lys Pro Gly Gln Pro
        35                  40                  45

Lys Leu Leu Ile Ser Val Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Phe Tyr Cys His His Ser Arg
                85                  90                  95

Glu Leu Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 13
<211> LENGTH: 351
<212> TYPE: DNA
<213> ORGANISM: Artificial Sequence
<220> FEATURE:
<223> OTHER INFORMATION: Ab 4382 VH coding sequence

<400> SEQUENCE: 13
gaagtgcagc tgcagcagtc tggccccgag ctggtgaaac ctggcgcctc cgtgaagatc      60
tcctgcaccg cctccggcta caccttcacc gactactaca tgaactgggt gaaacagtcc     120
cacggaaagt ccctggaatg gatcggagac atcaacccca caacggcgg caccaactac     180 aaccagaagt ggaagggcaa ggccaccctg accatccaca gtcctccag caccgcctac     240 atggaactgc ggtccctgac ctccgaggac tccgccgtgt acttctgtgt gcctggcggc     300
ctgcggtcct acttcgatta ctggggccag ggcaccaccc tgacagtctc g              351

<210> SEQ ID NO 14
<211> LENGTH: 117
<212> TYPE: PRT
<213> ORGANISM: Mus musculus
<220> FEATURE:
<221> NAME/KEY: MISC_FEATURE
<223> OTHER INFORMATION: Ab 4382 VH

<400> SEQUENCE: 14

Glu Val Gln Leu Gln Gln Ser Gly Pro Glu Leu Val Lys Pro Gly Ala
1               5                   10                  15

Ser Val Lys Ile Ser Cys Thr Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45
```

```
Gly Asp Ile Asn Pro Asn Asn Gly Gly Thr Asn Tyr Asn Gln Lys Trp
        50                  55                  60

Lys Gly Lys Ala Thr Leu Thr Ile His Lys Ser Ser Ser Thr Ala Tyr
 65                  70                  75                  80

Met Glu Leu Arg Ser Leu Thr Ser Glu Asp Ser Ala Val Tyr Phe Cys
                     85                  90                  95

Val Pro Gly Gly Leu Arg Ser Tyr Phe Asp Tyr Trp Gly Gln Gly Thr
                100                 105                 110

Thr Leu Thr Val Ser
            115

<210> SEQ ID NO 15
<211> LENGTH: 642
<212> TYPE: DNA
<213> ORGANISM: Artificial Sequence
<220> FEATURE:
<223> OTHER INFORMATION: Ab 4382 LC coding sequence

<400> SEQUENCE: 15
gacatcgtga tgacccagtc cctgaagttc atgtccgcct ccgtgggcga ccgggtgtcc      60
atcacatgca aggcctccca ggatgtgtct gccgccgtgg cctggtatca gcagaagcct    120
ggccagtccc ccgagctgct gatctactgg gcctctaccc ggcacaccgg cgtgcccgac    180
agattcaccg gctctggctc cggcaccgac tacaccctga ccatctccag cgtgcaggcc    240
gaggacctgg ccctgtacta ctgccagcag cactacacca ccccccccac cttcggcgga    300
ggcaccaagc tggaaatcaa gcggaccgtg gccgctccct ccgtgttcat cttcccaccc    360
tccgacgagc agctgaagtc cggcaccgcc agcgtggtgt gcctgctgaa caacttctac    420
ccccgcgagg ccaaggtgca gtggaaggtg gacaacgccc tgcagtccgg caactcccag    480
gaatccgtga ccgagcagga ctccaaggac agcacctact ccctgtcctc caccctgacc    540
ctgtccaagg ccgactacga aagcacaag gtgtacgcct gcgaagtgac ccaccagggc    600
ctgtccagcc ccgtgaccaa gtccttcaac cggggcgagt gc                      642

<210> SEQ ID NO 16
<211> LENGTH: 214
<212> TYPE: PRT
<213> ORGANISM: Mus musculus
<220> FEATURE:
<221> NAME/KEY: MISC_FEATURE
<223> OTHER INFORMATION: Ab 4382 LC

<400> SEQUENCE: 16

Asp Ile Val Met Thr Gln Ser Leu Lys Phe Met Ser Ala Ser Val Gly
 1               5                  10                  15

Asp Arg Val Ser Ile Thr Cys Lys Ala Ser Gln Asp Val Ser Ala Ala
                20                  25                  30

Val Ala Trp Tyr Gln Gln Lys Pro Gly Gln Ser Pro Glu Leu Leu Ile
            35                  40                  45

Tyr Trp Ala Ser Thr Arg His Thr Gly Val Pro Asp Arg Phe Thr Gly
     50                  55                  60

Ser Gly Ser Gly Thr Asp Tyr Thr Leu Thr Ile Ser Ser Val Gln Ala
 65                  70                  75                  80

Glu Asp Leu Ala Leu Tyr Tyr Cys Gln Gln His Tyr Thr Thr Pro Pro
                 85                  90                  95

Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
```

```
                115                 120                 125
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 17
<211> LENGTH: 351
<212> TYPE: DNA
<213> ORGANISM: Artificial Sequence
<220> FEATURE:
<223> OTHER INFORMATION: Ab 4383 VH coding sequence

<400> SEQUENCE: 17
cagatccagc tggtgcagtc tggccccgag cggaagaaac ccggcgagac agtgaagatc      60
tcctgcaagg cctccggcta caccttcacc gactactcca ccactgggt gaaacaggcc     120 cctggaaagg gctgaagtg atgggatgg atcaacaccg ccaccggcga gcctacccac     180
gtggacgact tcaagggcag attcgccttc tccctggaaa cctccgcctc caccgcctac     240
ctgcagatca ccaacctgaa gaacgaggat accgctacct acttctgcac cgcctgggcc     300
tacgagccct acttcgacta ctggggccag ggcaccaccc tgacagtctc g              351

<210> SEQ ID NO 18
<211> LENGTH: 117
<212> TYPE: PRT
<213> ORGANISM: Mus musculus
<220> FEATURE:
<221> NAME/KEY: MISC_FEATURE
<223> OTHER INFORMATION: Ab 4383 VH

<400> SEQUENCE: 18

Gln Ile Gln Leu Val Gln Ser Gly Pro Glu Arg Lys Lys Pro Gly Glu
1               5                   10                  15

Thr Val Lys Ile Ser Cys Lys Ala Ser Gly Tyr Thr Phe Thr Asp Tyr
                20                  25                  30

Ser Ile His Trp Val Lys Gln Ala Pro Gly Lys Gly Leu Lys Trp Met
            35                  40                  45

Gly Trp Ile Asn Thr Ala Thr Gly Glu Pro Thr His Val Asp Asp Phe
        50                  55                  60

Lys Gly Arg Phe Ala Phe Ser Leu Glu Thr Ser Ala Ser Thr Ala Tyr
65                  70                  75                  80

Leu Gln Ile Thr Asn Leu Lys Asn Glu Asp Thr Ala Thr Tyr Phe Cys
                85                  90                  95

Thr Ala Trp Ala Tyr Glu Pro Tyr Phe Asp Tyr Trp Gly Gln Gly Thr
            100                 105                 110

Thr Leu Thr Val Ser
        115

<210> SEQ ID NO 19
<211> LENGTH: 642
```

```
<212> TYPE: DNA
<213> ORGANISM: Artificial Sequence
<220> FEATURE:
<223> OTHER INFORMATION: Ab 4383 LC coding sequence

<400> SEQUENCE: 19
gatatcgtga tgacccagtc ccacaagttc atgtccacct ccgtgggcga ccgggtgtcc      60
atcacatgca aggcctccca ggacgtgttc accgccgtgg cctggtatca gcagaagccc     120
ggccagtccc ccaagctgct gatctactcc gcctcctccc ggtacaccgg cgtgcccgac     180
agattcaccg gctctggctc cggcaccgac ttcatcttca ccatctccag cgtgcaggcc     240
gaggacctgg ccatctacca ctgccagcag cacttcggca tcccttggac cttcggcgga     300
ggcaccaagc tggaaatcaa gcggaccgtg gccgctccct ccgtgttcat cttcccaccc     360
tccgacgagc agctgaagtc cggcaccgcc tccgtggtgt gcctgctgaa caacttctac     420
ccccgcgagg ccaaggtgca gtggaaggtg gacaacgccc tgcagtccgg caactcccag     480
gaatccgtga ccgagcagga ctccaaggac agcacctact ccctgtcctc caccctgacc     540
ctgtccaagg ccgactacga gaagcacaag gtgtacgcct gcgaagtgac ccaccagggc     600
ctgtccagcc ccgtgaccaa gtccttcaac cggggcgagt gc                        642

<210> SEQ ID NO 20
<211> LENGTH: 214
<212> TYPE: PRT
<213> ORGANISM: Mus musculus
<220> FEATURE:
<221> NAME/KEY: MISC_FEATURE
<223> OTHER INFORMATION: Ab 4383 LC

<400> SEQUENCE: 20

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Phe Thr Ala
            20                  25                  30

Val Ala Trp Tyr Gln Gln Lys Pro Gly Gln Ser Pro Lys Leu Leu Ile
        35                  40                  45

Tyr Ser Ala Ser Ser Arg Tyr Thr Gly Val Pro Asp Arg Phe Thr Gly
    50                  55                  60

Ser Gly Ser Gly Thr Asp Phe Ile Phe Thr Ile Ser Ser Val Gln Ala
65                  70                  75                  80

Glu Asp Leu Ala Ile Tyr His Cys Gln Gln His Phe Gly Ile Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

-continued

<210> SEQ ID NO 21
<211> LENGTH: 354
<212> TYPE: DNA
<213> ORGANISM: Artificial Sequence
<220> FEATURE:
<223> OTHER INFORMATION: Ab 4384 VH coding sequence

<400> SEQUENCE: 21

```
caggtgcagc tgcagcagcc tggcacagag ctggtgaaac ctggcgcctc cgtgaagctg      60
tcctgcaagg cctccggcta caccttcacc tcccactgga tgcactgggt gaaacagcgg     120
cctggacagg gcctggaatg gatcggcaac atcaacccct ccaacggcgg caccaactac     180
aacgagaagt tcaagtcccg ggccaccctg accgtggaca aggcctcctc caccgcctac     240
atgcagctgt cctccctgac ctccgaggac tccgccgtgt actactgcgc cagagcctac     300
tacgacttca gttggttcgt gtactggggc cagggcaccc tggtgacagt ctcg           354
```

<210> SEQ ID NO 22
<211> LENGTH: 118
<212> TYPE: PRT
<213> ORGANISM: Mus musculus
<220> FEATURE:
<221> NAME/KEY: MISC_FEATURE
<223> OTHER INFORMATION: Ab 4384 VH

<400> SEQUENCE: 22

```
Gln Val Gln Leu Gln Gln Pro Gly Thr Glu Leu Val Lys Pro Gly Ala
  1               5                  10                  15

Ser Val Lys Leu Ser Cys Lys Ala Ser Gly Tyr Thr Phe Thr Ser His
             20                  25                  30

Trp Met His Trp Val Lys Gln Arg Pro Gly Gln Gly Leu Glu Trp Ile
         35                  40                  45

Gly Asn Ile Asn Pro Ser Asn Gly Gly Thr Asn Tyr Asn Glu Lys Phe
     50                  55                  60

Lys Ser Arg Ala Thr Leu Thr Val Asp Lys Ala Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Ala Tyr Tyr Asp Phe Ser Trp Phe Val Tyr Trp Gly Gln Gly
            100                 105                 110

Thr Leu Val Thr Val Ser
        115
```

<210> SEQ ID NO 23
<211> LENGTH: 639
<212> TYPE: DNA
<213> ORGANISM: Artificial Sequence
<220> FEATURE:
<223> OTHER INFORMATION: Ab 4384 LC coding sequence

<400> SEQUENCE: 23

```
gatatccaga tgacccagac ctcctccagc ctgtccgcct ccctgggcga cagagtgacc      60
atctcctgcc ggtcctccca ggacatctcc aactacctga actggtatca gcagaaaccc     120
gacggcaccg tgaagctgct gatgtacatc tcccggctgc actccggcgt gcctccagga     180
ttctccggct ctggctccgg caccgagtac tccctgacca tcagcaacct ggaacaggaa     240
gatatcgcta cctacttctg tcagcagggc aacaccctgc cctgaccttc ggcgctggc     300 accaagctgg aactgaagcg gaccgtggcc gctcccctcg tgttcatctt cccaccctcc     360
```

```
gacgagcagc tgaagtccgg caccgcctcc gtggtgtgcc tgctgaacaa cttctacccc    420
cgcgaggcca aggtgcagtg aaggtggac aacgccctgc agtccggcaa ctcccaggaa     480
tccgtgaccg agcaggactc caaggacagc acctactccc tgtcctccac cctgaccctg    540
tccaaggccg actacgagaa gcacaaggtg tacgcctgcg aagtgaccca ccagggcctg    600
tccagccccg tgaccaagtc cttcaaccgg ggcgagtgc                            639
```

```
<210> SEQ ID NO 24
<211> LENGTH: 213
<212> TYPE: PRT
<213> ORGANISM: Mus musculus
<220> FEATURE:
<221> NAME/KEY: MISC_FEATURE
<223> OTHER INFORMATION: Ab 4384 LC

<400> SEQUENCE: 24
```

```
Asp Ile Gln Met Thr Gln Thr Ser Ser Leu Ser Ala Ser Leu Gly
1               5                   10                  15

Asp Arg Val Thr Ile Ser Cys Arg Ser Ser Gln Asp Ile Ser Asn Tyr
            20                  25                  30

Leu Asn Trp Tyr Gln Gln Lys Pro Asp Gly Thr Val Lys Leu Leu Met
        35                  40                  45

Tyr Ile Ser Arg Leu His Ser Gly Val Pro Ser Arg Phe Ser Gly Ser
    50                  55                  60

Gly Ser Gly Thr Glu Tyr Ser Leu Thr Ile Ser Asn Leu Glu Gln Glu
65                  70                  75                  80

Asp Ile Ala Thr Tyr Phe Cys Gln Gln Gly Asn Thr Leu Pro Leu Thr
                85                  90                  95

Phe Gly Ala Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

```
<210> SEQ ID NO 25
<211> LENGTH: 348
<212> TYPE: DNA
<213> ORGANISM: Artificial Sequence
<220> FEATURE:
<223> OTHER INFORMATION: Ab 4385 VH coding sequence

<400> SEQUENCE: 25
caggtgacac tgaaagagtc tggcgccgag ctgatgaagc tggcgcctc cgtgaagctg     60 tcctgcaagg ccaccggcta caccttcacc ggctactgga tcgagtgggt gaaacagcgg    120
cctggacacg gcctggaatg gatcggagag atcctgcctg ctccggctc caccaactac    180
```

```
aacgagaagt tcaagggcga ggccaccttt accgccgaca cctcctccaa caccgcctac    240
atgcacctgt cctccctgac caccgaggac tccgccatct actactgcgc cagatggggc    300
gacggctcct tcgcttattg gggccagggc accctggtga cagtctcg                 348
```

<210> SEQ ID NO 26
<211> LENGTH: 116
<212> TYPE: PRT
<213> ORGANISM: Mus musculus
<220> FEATURE:
<221> NAME/KEY: MISC_FEATURE
<223> OTHER INFORMATION: Ab 4385 VH

<400> SEQUENCE: 26

```
Gln Val Thr Leu Lys Glu Ser Gly Ala Glu Leu Met Lys Pro Gly Ala
1               5                   10                  15

Ser Val Lys Leu Ser Cys Lys Ala Thr Gly Tyr Thr Phe Thr Gly Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Ser Thr Asn Tyr Asn Glu Lys Phe
    50                  55                  60

Lys Gly Glu Ala Thr Phe Thr Ala Asp Thr Ser Ser Asn Thr Ala Tyr
65                  70                  75                  80

Met His Leu Ser Ser Leu Thr Thr Glu Asp Ser Ala Ile Tyr Tyr Cys
                85                  90                  95

Ala Arg Trp Gly Asp Gly Ser Phe Ala Tyr Trp Gly Gln Gly Thr Leu
            100                 105                 110

Val Thr Val Ser
        115
```

<210> SEQ ID NO 27
<211> LENGTH: 642
<212> TYPE: DNA
<213> ORGANISM: Artificial Sequence
<220> FEATURE:
<223> OTHER INFORMATION: Ab 4385 LC coding sequence

<400> SEQUENCE: 27

```
gatatcgtga tgacccagtc ccagaaattc atgtccacct ccgtgggcga ccgggtgtcc     60
atcacatgca aggcctccca gaacgtgggc accgccgtgt cctggtatca gcagaagccc    120
ggccagtccc ccaagctgct gatcttctcc acctccaacc ggtacaccgg cgtgcccgac    180
agattcaccg gctctggctc cggcaccgac ttcaccctga ccatctccaa catgcagtcc    240
gaggacctgg ccgactactt ctgccagcag taccggtcct accccttcac cttcggcagc    300
ggcaccaagc tggaaatcaa gcggaccgtg gccgctccct ccgtgttcat cttcccaccc    360
tccgacgagc agctgaagtc cggcaccgcc tccgtggtgt gcctgctgaa caacttctac    420
ccccgcgagg ccaaggtgca gtggaaggtg gacaacgccc tgcagtccgg caactcccag    480
gaatccgtga ccgagcagga ctccaaggac agcacctact ccctgtcctc caccctgacc    540
ctgtccaagg ccgactacga gaagcacaag gtgtacgcct gcgaagtgac ccaccagggc    600
ctgtccagcc ccgtgaccaa gtccttcaac cggggcgagt gc                       642
```

<210> SEQ ID NO 28
<211> LENGTH: 214
<212> TYPE: PRT
<213> ORGANISM: Mus musculus
<220> FEATURE:
<221> NAME/KEY: MISC_FEATURE
<223> OTHER INFORMATION: Ab 4385 LC

<400> SEQUENCE: 28

```
Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Gly Thr Ala
            20                  25                  30

Val Ser Trp Tyr Gln Gln Lys Pro Gly Gln Ser Pro Lys Leu Leu Ile
        35                  40                  45

Phe Ser Thr Ser Asn Arg Tyr Thr Gly Val Pro Asp Arg Phe Thr Gly
    50                  55                  60

Ser Gly Ser Gly Thr Asp Phe Thr Leu Thr Ile Ser Asn Met Gln Ser
65                  70                  75                  80

Glu Asp Leu Ala Asp Tyr Phe Cys Gln Gln Tyr Arg Ser Tyr Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 29
<211> LENGTH: 348
<212> TYPE: DNA
<213> ORGANISM: Artificial Sequence
<220> FEATURE:
<223> OTHER INFORMATION: Ab 4386 VH coding sequence

<400> SEQUENCE: 29

```
caggtgcagc tgcagcagcc tggagctgaa ctggtgaaac ctggcgcctc cgtgaaactg    60
tcctgcaagg cctccggcta caccttcacc agctactgga tgcactgggt gaaacagcgg   120
cctggacagg gcctggaatg gatcggcatg atccacccca ctccggctc catcaactac    180
aacgagaagt tcaagaacaa ggccaccctg accgtggtga tctcctcctc caccgcctac   240
atgcagctgt cctccctgac ctccgaggac tccgccgtgt actactgcgc cggctacggc   300
aacggcccca tggattattg gggccagggc acctccgtga ccgtctcg              348
```

<210> SEQ ID NO 30
<211> LENGTH: 116
<212> TYPE: PRT
<213> ORGANISM: Mus musculus
<220> FEATURE:
<221> NAME/KEY: MISC_FEATURE
<223> OTHER INFORMATION: Ab 4386 VH

<400> SEQUENCE: 30

```
Gln Val Gln Leu Gln Gln Pro Gly Ala Glu Leu Val Lys Pro Gly Ala
```

```
                  1               5                  10                 15
Ser Val Lys Leu Ser Cys Lys Ala Ser Gly Tyr Thr Phe Thr Ser Tyr
                20                  25                 30

Trp Met His Trp Val Lys Gln Arg Pro Gly Gln Gly Leu Glu Trp Ile
                35                  40                 45

Gly Met Ile His Pro Asn Ser Gly Ser Ile Asn Tyr Asn Glu Lys Phe
    50                  55                  60

Lys Asn Lys Ala Thr Leu Thr Val Val Ile Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Gly Tyr Gly Asn Gly Pro Met Asp Tyr Trp Gly Gln Gly Thr Ser
            100                 105                 110

Val Thr Val Ser
        115

<210> SEQ ID NO 31
<211> LENGTH: 639
<212> TYPE: DNA
<213> ORGANISM: Artificial Sequence
<220> FEATURE:
<223> OTHER INFORMATION: Ab 4386 LC coding sequence

<400> SEQUENCE: 31
cagatcgtgc tgacccagtc ccccgccatc atgtctgcca gccctggcga gaaagtgaca      60
atctcctgct ccgcctcctc cagcgtgtcc tacctgtact ggtatcagca gaagcccggc     120
tccagcccca agccctggat ctaccggacc tccaacctgg cctcggcgt gccagccaga     180
ttctccggct ccggcagcgg cacctcctac tccctgacca tctcctccat ggaagccgag    240
gacgccgcca cctactactg ccagcagtac acaaactacc ccctgacctt cggcgctggc    300
accaagctgg aactgaaacg gaccgtggcc gctccctccg tgttcatctt cccaccctcc    360
gacgagcagc tgaagtccgg caccgcctcc gtggtgtgcc tgctgaacaa cttctacccc    420
cgcgaggcca aggtgcagtg gaaggtggac aacgccctgc agtccggcaa ctcccaggaa    480
tccgtgaccg agcaggactc caaggacagc acctacagcc tgtcctccac cctgaccctg    540
tccaaggccg actacgagaa gcacaaggtg tacgcctgcg aagtgaccca ccagggcctg    600
tccagccccg tgaccaagtc cttcaaccgg ggcgagtgc                            639

<210> SEQ ID NO 32
<211> LENGTH: 213
<212> TYPE: PRT
<213> ORGANISM: Mus musculus
<220> FEATURE:
<221> NAME/KEY: MISC_FEATURE
<223> OTHER INFORMATION: Ab 4386 LC

<400> SEQUENCE: 32

Gln Ile Val Leu Thr Gln Ser Pro Ala Ile Met Ser Ala Ser Pro Gly
1               5                   10                  15

Glu Lys Val Thr Ile Ser Cys Ser Ala Ser Ser Ser Val Ser Tyr Leu
                20                  25                  30

Tyr Trp Tyr Gln Gln Lys Pro Gly Ser Ser Pro Lys Pro Trp Ile Tyr
            35                  40                  45

Arg Thr Ser Asn Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80
```

Asp Ala Ala Thr Tyr Tyr Cys Gln Gln Tyr His Asn Tyr Pro Leu Thr
            85                  90                  95

Phe Gly Ala Gly Thr Lys Leu Glu Leu Lys Arg Thr Val Ala Ala Pro
        100                 105                 110

Ser Val Phe Ile Phe Pro Pro Ser Asp Glu Gln Leu Lys Ser Gly Thr
    115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 33
<211> LENGTH: 357
<212> TYPE: DNA
<213> ORGANISM: Artificial Sequence
<220> FEATURE:
<223> OTHER INFORMATION: Ab 4387 VH coding sequence

<400> SEQUENCE: 33
caggtgcagc tgcagcagtc tggcgctgag ctggtgcgac ccggcacctc cgtgaagatg      60
tcctgcaagg cctccggcta caccttcacc aactactgga tcggctgggc caagcagcgg     120
cctggacacg gactggaatg gatcggagac atcctgcctg gcggcggata cacccactac     180
aacgagaagt tcaagggcaa ggccaccctg accgccgaca gtcctcctc caccgccttc      240 atgcagttct ccagcctgac ctccgaggac tccgccatct actactgcgc cagaggctcc     300
agcggctacc cctactactt cgactactgg ggccagggca ccaccctgac agtctcg        357

<210> SEQ ID NO 34
<211> LENGTH: 119
<212> TYPE: PRT
<213> ORGANISM: Mus musculus
<220> FEATURE:
<221> NAME/KEY: MISC_FEATURE
<223> OTHER INFORMATION: Ab 4387 VH

<400> SEQUENCE: 34

Gln Val Gln Leu Gln Gln Ser Gly Ala Glu Leu Val Arg Pro Gly Thr
1               5                   10                  15

Ser Val Lys Met Ser Cys Lys Ala Ser Gly Tyr Thr Phe Thr Asn Tyr
            20                  25                  30

Trp Ile Gly Trp Ala Lys Gln Arg Pro Gly His Gly Leu Glu Trp Ile
        35                  40                  45

Gly Asp Ile Leu Pro Gly Gly Gly Tyr Thr His Tyr Asn Glu Lys Phe
    50                  55                  60

Lys Gly Lys Ala Thr Leu Thr Ala Asp Lys Ser Ser Ser Thr Ala Phe
65                  70                  75                  80

Met Gln Phe Ser Ser Leu Thr Ser Glu Asp Ser Ala Ile Tyr Tyr Cys
                85                  90                  95

Ala Arg Gly Ser Ser Gly Tyr Pro Tyr Tyr Phe Asp Tyr Trp Gly Gln

Gly Thr Thr Leu Thr Val Ser
                115

<210> SEQ ID NO 35
<211> LENGTH: 648
<212> TYPE: DNA
<213> ORGANISM: Artificial Sequence
<220> FEATURE:
<223> OTHER INFORMATION: Ab 4387 LC coding sequence

<400> SEQUENCE: 35
cagatcgtga tgacccagtc ccacaagttc atgtccacct ccgtgggcga ccgggtgtcc      60
atcacatgca aggcctccca ggacgtgggc accgccgtgg cctggtatca gcagaagccc     120
ggccagtccc ccaagctgct gatctactgg gcctccaccc ggcacaccgg cgtgccagac     180
agattcaccg gctccggcag cggcaccgac ttcaccctga ccatctccaa cgtgcagtcc     240
gaggacctgg ccgactactt ctgccagcag tactcctcct accctacat gtacaccttc      300 ggcggaggca ccaagctgga aatcaagcgg accgtggccg ctccctccgt gttcatcttc     360
ccaccctccg acgagcagct gaagtccggc accgcctccg tggtgtgcct gctgaacaac     420
ttctaccccc gcgaggccaa ggtgcagtgg aaggtggaca acgccctgca gtccggcaac     480
tcccaggaat ccgtgaccga gcaggactcc aaggacagca cctactccct gtcctccacc     540
ctgaccctgt ccaaggccga ctacgagaag cacaaggtgt acgcctgcga agtgacccac     600
cagggcctgt ccagccccgt gaccaagtcc ttcaaccggg gcgagtgc                  648

<210> SEQ ID NO 36
<211> LENGTH: 216
<212> TYPE: PRT
<213> ORGANISM: Mus musculus
<220> FEATURE:
<221> NAME/KEY: MISC_FEATURE
<223> OTHER INFORMATION: Ab 4387 LC

<400> SEQUENCE: 36

Gln Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Tyr
                85                  90                  95

Met Tyr Thr Phe Gly Gly Gly Thr Lys Leu Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

```
Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 37
<211> LENGTH: 348
<212> TYPE: DNA
<213> ORGANISM: Artificial Sequence
<220> FEATURE:
<223> OTHER INFORMATION: Ab 4519 VH coding sequence

<400> SEQUENCE: 37
gagatccagc tgcagcagtc tggccccgag ctggtgaaac ctggcgcctc cgtgaaggtg      60
tcctgcaagg cctccggcta ctccttcacc gactacaaca tctactgggt gaaacagtcc     120
cacggaaagt ccctggaatg gatcggatac atcgacccct acaacggcgg cacctcctac     180
aaccagaagt tcaagggcaa ggccaccctg accgtggaca gtcctcctc caccgccttc      240 atgcacctga actccctgac ctccgaggac tccgccgtgt actactgcgc cagaggcgct     300
ggctacgccc tggattattg gggccagggc acctccgtga cagtctcg                  348

<210> SEQ ID NO 38
<211> LENGTH: 116
<212> TYPE: PRT
<213> ORGANISM: Mus musculus
<220> FEATURE:
<221> NAME/KEY: MISC_FEATURE
<223> OTHER INFORMATION: Ab 4519 VH

<400> SEQUENCE: 38

Glu Ile Gln Leu Gln Gln Ser Gly Pro Glu Leu Val Lys Pro Gly Ala
1               5                   10                  15

Ser Val Lys Val Ser Cys Lys Ala Ser Gly Tyr Ser Phe Thr Asp Tyr
            20                  25                  30

Asn Ile Tyr Trp Val Lys Gln Ser His Gly Lys Ser Leu Glu Trp Ile
        35                  40                  45

Gly Tyr Ile Asp Pro Tyr Asn Gly Gly Thr Ser Tyr Asn Gln Lys Phe
    50                  55                  60

Lys Gly Lys Ala Thr Leu Thr Val Asp Lys Ser Ser Ser Thr Ala Phe
65                  70                  75                  80

Met His Leu Asn Ser Leu Thr Ser Glu Asp Ser Ala Val Tyr Tyr Cys
                85                  90                  95

Ala Arg Gly Ala Gly Tyr Ala Leu Asp Tyr Trp Gly Gln Gly Thr Ser
            100                 105                 110

Val Thr Val Ser
        115

<210> SEQ ID NO 39
<211> LENGTH: 639
<212> TYPE: DNA
<213> ORGANISM: Artificial Sequence
<220> FEATURE:
<223> OTHER INFORMATION: Ab 4519 LC coding sequence

<400> SEQUENCE: 39
cagatcgtgc tgacccagtc ccctgccctg atgtccgcct cccctggcga aaagtgaca      60 atgacctgct ccgcctcctc ctccgtgtcc tacatgtact ggtatcagca gaagccccgg    120
```

| | |
|---|---|
| tccagcccca agccctggat ctacctgacc tccaacctgg cctccggcgt gcccgccaga | 180 |
| ttctctggct ccggctccgg cacctcctac accctgacca tctccagcat ggaagccgag | 240 |
| gacgccgcca cctactactg ccagcagtgg tcctccaccc cctacacctt cggcggaggc | 300 |
| accaagctgg aactgaagcg gaccgtggcc gctccctccg tgttcatctt cccaccctcc | 360 |
| gacgagcagc tgaagtccgg caccgcctcc gtggtgtgcc tgctgaacaa cttctacccc | 420 |
| cgcgaggcca aggtgcagtg gaaggtggac aacgccctgc agtccggcaa ctcccaggaa | 480 |
| tccgtgaccg agcaggactc caaggacagc acctactccc tgtccagcac cctgaccctg | 540 |
| tccaaggccg actacgagaa gcacaaggtg tacgcctgcg aagtgaccca ccagggcctg | 600 |
| tccagccctg tgaccaagtc cttcaaccgg ggcgagtgc | 639 |

```
<210> SEQ ID NO 40
<211> LENGTH: 213
<212> TYPE: PRT
<213> ORGANISM: Mus musculus
<220> FEATURE:
<221> NAME/KEY: MISC_FEATURE
<223> OTHER INFORMATION: Ab 4519 LC

<400> SEQUENCE: 40

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Thr Leu Thr Ile Ser Ser Met Glu Ala Glu
65                  70                  75                  80

Asp Ala Ala Thr Tyr Tyr Cys Gln Gln Trp Ser Ser Thr Pro Tyr Thr
                85                  90                  95

Phe Gly Gly Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 41
<211> LENGTH: 320
<212> TYPE: DNA
<213> ORGANISM: Homo sapiens
<220> FEATURE:
<221> NAME/KEY: misc_feature
<223> OTHER INFORMATION: Human Ig kappa DNA
```

```
<220> FEATURE:
<221> NAME/KEY: exon
<222> LOCATION: (3)..(320)

<400> SEQUENCE: 41 ga act gtg gct gca cca tct gtc ttc atc ttc ccg cca tct gat gag      47
   Thr Val Ala Ala Pro Ser Val Phe Ile Phe Pro Pro Ser Asp Glu
   1               5                   10                  15 cag ttg aaa tct gga act gcc tct gtt gtg tgc ctg ctg aat aac ttc     95
Gln Leu Lys Ser Gly Thr Ala Ser Val Val Cys Leu Leu Asn Asn Phe
            20                  25                  30 tat ccc aga gag gcc aaa gta cag tgg aag gtg gat aac gcc ctc caa    143
Tyr Pro Arg Glu Ala Lys Val Gln Trp Lys Val Asp Asn Ala Leu Gln
        35                  40                  45 tcg ggt aac tcc cag gag agt gtc aca gag cag gac agc aag gac agc    191
Ser Gly Asn Ser Gln Glu Ser Val Thr Glu Gln Asp Ser Lys Asp Ser
    50                  55                  60 acc tac agc ctc agc agc acc ctg acg ctg agc aaa gca gac tac gag    239
Thr Tyr Ser Leu Ser Ser Thr Leu Thr Leu Ser Lys Ala Asp Tyr Glu
65                  70                  75 aaa cac aaa gtc tac gcc tgc gaa gtc acc cat cag ggc ctg agc tcg    287
Lys His Lys Val Tyr Ala Cys Glu Val Thr His Gln Gly Leu Ser Ser
80                  85                  90                  95 ccc gtc aca aag agc ttc aac agg gga gag tgt                        320
Pro Val Thr Lys Ser Phe Asn Arg Gly Glu Cys
                100                 105

<210> SEQ ID NO 42
<211> LENGTH: 106
<212> TYPE: PRT
<213> ORGANISM: Homo sapiens
<220> FEATURE:
<221> NAME/KEY: misc_feature
<223> OTHER INFORMATION: Human Ig kappa constant region

<400> SEQUENCE: 42

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 43
<211> LENGTH: 1602
<212> TYPE: DNA
<213> ORGANISM: Homo sapiens
<220> FEATURE:
<221> NAME/KEY: misc_feature
<223> OTHER INFORMATION: Human IGHG1 constant domain genomic sequence
<220> FEATURE:
<221> NAME/KEY: exon
<222> LOCATION: (1)..(298)
<220> FEATURE:
<221> NAME/KEY: exon
<222> LOCATION: (690)..(734)
```

-continued

```
<220> FEATURE:
<221> NAME/KEY: exon
<222> LOCATION: (853)..(1182)
<220> FEATURE:
<221> NAME/KEY: exon
<222> LOCATION: (1280)..(1602)

<400> SEQUENCE: 43
```

| | | | | | | | | | | | | | | | | |
|---|---|---|---|---|---|---|---|---|---|---|---|---|---|---|---|---|
| agt | gcc | tcc | acc | aag | ggc | cca | tcg | gtc | ttc | ccc | ctg | gca | ccc | tcc | tcc | 48 |
| Ser | Ala | Ser | Thr | Lys | Gly | Pro | Ser | Val | Phe | Pro | Leu | Ala | Pro | Ser | Ser | |
| 1 | | | | 5 | | | | | 10 | | | | | 15 | | |
| aag | agc | acc | tct | ggg | ggc | aca | gcg | gcc | ctg | ggc | tgc | ctg | gtc | aag | gac | 96 |
| Lys | Ser | Thr | Ser | Gly | Gly | Thr | Ala | Ala | Leu | Gly | Cys | Leu | Val | Lys | Asp | |
| | | | 20 | | | | | 25 | | | | | 30 | | | |
| tac | ttc | ccc | gaa | ccg | gtg | acg | gtg | tcg | tgg | aac | tca | ggc | gcc | ctg | acc | 144 |
| Tyr | Phe | Pro | Glu | Pro | Val | Thr | Val | Ser | Trp | Asn | Ser | Gly | Ala | Leu | Thr | |
| | | | | 35 | | | | | 40 | | | | | 45 | | |
| agc | ggc | gtg | cac | acc | ttc | ccg | gct | gtc | cta | cag | tcc | tca | gga | ctc | tac | 192 |
| Ser | Gly | Val | His | Thr | Phe | Pro | Ala | Val | Leu | Gln | Ser | Ser | Gly | Leu | Tyr | |
| | 50 | | | | | 55 | | | | | 60 | | | | | |
| tcc | ctc | agc | agc | gtg | gtg | acc | gtg | ccc | tcc | agc | agc | ttg | ggc | acc | cag | 240 |
| Ser | Leu | Ser | Ser | Val | Val | Thr | Val | Pro | Ser | Ser | Ser | Leu | Gly | Thr | Gln | |
| 65 | | | | | 70 | | | | | 75 | | | | | 80 | |
| acc | tac | atc | tgc | aac | gtg | aat | cac | aag | ccc | agc | aac | acc | aag | gtg | gac | 288 |
| Thr | Tyr | Ile | Cys | Asn | Val | Asn | His | Lys | Pro | Ser | Asn | Thr | Lys | Val | Asp | |
| | | | | 85 | | | | | 90 | | | | | 95 | | |
| aag | aga | gtt | g | gtgagaggcc | agcacaggga | gggagggtgt | ctgctggaag | | | | | | | | | 338 |
| Lys | Arg | Val | | | | | | | | | | | | | | |

| | | |
|---|---|---|
| ccaggctcag cgctcctgcc tggacgcatc ccggctatgc agtcccagtc cagggcagca | 398 |
| aggcaggccc cgtctgcctc ttcacccgga ggcctctgcc cgccccactc atgctcaggg | 458 |
| agagggtctt ctggcttttt ccccaggctc tgggcaggca caggctaggt gcccctaacc | 518 |
| caggccctgc acacaaaggg gcaggtgctg ggctcagacc tgccaagagc catatccggg | 578 |
| aggaccctgc cctgaccta agcccacccc aaaggccaaa ctctccactc cctcagctcg | 638 |
| gacaccttct ctcctcccag attccagtaa ctcccaatct tctctctgca g ag ccc | 694 |
| | Glu Pro | |

| | | | | | | | | | | | | | | | | |
|---|---|---|---|---|---|---|---|---|---|---|---|---|---|---|---|---|
| aaa | tct | tgt | gac | aaa | act | cac | aca | tgc | cca | ccg | tgc | cca | g | gtaagccagc | | 744 |
| Lys | Ser | Cys | Asp | Lys | Thr | His | Thr | Cys | Pro | Pro | Cys | Pro | | | | |
| 105 | | | | | 110 | | | | | | | | | | | |

| | |
|---|---|
| ccaggcctcg ccctccagct caaggcggga caggtgccct agagtagcct gcatccaggg | 804 |
| acaggcccca gccgggtgct gacacgtcca cctccatctc ttcctcag ca cct gaa | 860 |
| | Ala Pro Glu |

| | | | | | | | | | | | | | | | | |
|---|---|---|---|---|---|---|---|---|---|---|---|---|---|---|---|---|
| ctc | ctg | ggg | gga | ccg | tca | gtc | ttc | ctc | ttc | ccc | cca | aaa | ccc | aag | gac | 908 |
| Leu | Leu | Gly | Gly | Pro | Ser | Val | Phe | Leu | Phe | Pro | Pro | Lys | Pro | Lys | Asp | |
| | | | 120 | | | | | 125 | | | | | 130 | | | |
| acc | ctc | atg | atc | tcc | cgg | acc | cct | gag | gtc | aca | tgc | gtg | gtg | gtg | gac | 956 |
| Thr | Leu | Met | Ile | Ser | Arg | Thr | Pro | Glu | Val | Thr | Cys | Val | Val | Val | Asp | |
| | | 135 | | | | | 140 | | | | | 145 | | | | |
| gtg | agc | cac | gaa | gac | cct | gag | gtc | aag | ttc | aac | tgg | tac | gtg | gac | ggc | 1004 |
| Val | Ser | His | Glu | Asp | Pro | Glu | Val | Lys | Phe | Asn | Trp | Tyr | Val | Asp | Gly | |
| 150 | | | | | 155 | | | | | 160 | | | | | 165 | |
| gtg | gag | gtg | cat | aat | gcc | aag | aca | aag | ccg | cgg | gag | gag | cag | tac | aac | 1052 |
| Val | Glu | Val | His | Asn | Ala | Lys | Thr | Lys | Pro | Arg | Glu | Glu | Gln | Tyr | Asn | |
| | | | 170 | | | | | 175 | | | | | 180 | | | |
| agc | acg | tac | cgt | gtg | gtc | agc | gtc | ctc | acc | gtc | ctg | cac | cag | gac | tgg | 1100 |
| Ser | Thr | Tyr | Arg | Val | Val | Ser | Val | Leu | Thr | Val | Leu | His | Gln | Asp | Trp | |
| | | | 185 | | | | | 190 | | | | | 195 | | | |
| ctg | aat | ggc | aag | gag | tac | aag | tgc | aag | gtc | tcc | aac | aaa | gcc | ctc | cca | 1148 |
| Leu | Asn | Gly | Lys | Glu | Tyr | Lys | Cys | Lys | Val | Ser | Asn | Lys | Ala | Leu | Pro | |

```
                200               205              210
gcc ccc atc gag aaa acc atc tcc aaa gcc aaa g gtgggacccg                 1192
Ala Pro Ile Glu Lys Thr Ile Ser Lys Ala Lys
        215                 220 tggggtgcga gggccacatg gacagaggcc ggctcggccc accctctgcc ctgagagtga       1252
ccgctgtacc aacctctgtc cctacag gg  cag ccc cga gaa cca cag gtg tac        1305
                                Gly Gln Pro Arg Glu Pro Gln Val Tyr
                                                     230 acc ctg ccc cca tcc cgg gag gag atg acc aag aac cag gtc agc ctg         1353
Thr Leu Pro Pro Ser Arg Glu Glu Met Thr Lys Asn Gln Val Ser Leu
        235                 240                 245 acc tgc ctg gtc aaa ggc ttc tat ccc agc gac atc gcc gtg gag tgg         1401
Thr Cys Leu Val Lys Gly Phe Tyr Pro Ser Asp Ile Ala Val Glu Trp
250                 255                 260                 265 gag agc aat ggg cag ccg gag aac aac tac aag acc acg cct ccc gtg         1449
Glu Ser Asn Gly Gln Pro Glu Asn Asn Tyr Lys Thr Thr Pro Pro Val
                    270                 275                 280 ctg gac tcc gac ggc tcc ttc ttc ctc tat agc aag ctc acc gtg gac         1497
Leu Asp Ser Asp Gly Ser Phe Phe Leu Tyr Ser Lys Leu Thr Val Asp
                285                 290                 295 aag agc agg tgg cag cag ggg aac gtc ttc tca tgc tcc gtg atg cat         1545
Lys Ser Arg Trp Gln Gln Gly Asn Val Phe Ser Cys Ser Val Met His
            300                 305                 310 gag gct ctg cac aac cac tac acg cag aag agc ctc tcc ctg tcc ccg         1593
Glu Ala Leu His Asn His Tyr Thr Gln Lys Ser Leu Ser Leu Ser Pro
        315                 320                 325 ggt aaa tga                                                              1602
Gly Lys
330

<210> SEQ ID NO 44
<211> LENGTH: 331
<212> TYPE: PRT
<213> ORGANISM: Homo sapiens
<220> FEATURE:
<221> NAME/KEY: misc_feature
<223> OTHER INFORMATION: Human IGHG1 constant region

<400> SEQUENCE: 44

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
                20                  25                  30

Tyr Phe Pro Glu Pro Val Thr Val Ser Trp Asn Ser Gly Ala Leu Thr
            35                  40                  45

Ser Gly Val His Thr Phe Pro Ala Val Leu Gln Ser Ser Gly Leu Tyr
        50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Arg Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160
```

```
Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 45
<211> LENGTH: 8
<212> TYPE: PRT
<213> ORGANISM: Mus musculus
<220> FEATURE:
<221> NAME/KEY: misc_feature
<223> OTHER INFORMATION: Ab 4517 HCDR1

<400> SEQUENCE: 45

Gly Phe Thr Phe Ser Ser Tyr Gly
1               5

<210> SEQ ID NO 46
<211> LENGTH: 8
<212> TYPE: PRT
<213> ORGANISM: Mus musculus
<220> FEATURE:
<221> NAME/KEY: misc_feature
<223> OTHER INFORMATION: Ab 4517 HCDR2

<400> SEQUENCE: 46

Ile Ser Gly Gly Gly Ser Tyr Thr
1               5

<210> SEQ ID NO 47
<211> LENGTH: 16
<212> TYPE: PRT
<213> ORGANISM: Mus musculus
<220> FEATURE:
<221> NAME/KEY: misc_feature
<223> OTHER INFORMATION: Ab 4517 HCDR3

<400> SEQUENCE: 47

Cys Ala Arg Lys Gly Asn Tyr Gly Asn Tyr Gly Lys Leu Ala Tyr Trp
1               5                   10                  15

<210> SEQ ID NO 48
<211> LENGTH: 8
<212> TYPE: PRT
```

```
<213> ORGANISM: Mus musculus
<220> FEATURE:
<221> NAME/KEY: misc_feature
<223> OTHER INFORMATION: Ab 4518 HCDR1

<400> SEQUENCE: 48

Gly Phe Asn Ile Lys Asp Ile Phe
1               5

<210> SEQ ID NO 49
<211> LENGTH: 8
<212> TYPE: PRT
<213> ORGANISM: Mus musculus
<220> FEATURE:
<221> NAME/KEY: misc_feature
<223> OTHER INFORMATION: Ab 4518 HCDR2

<400> SEQUENCE: 49

Ile Asp Pro Ala Asn Asp Asn Pro
1               5

<210> SEQ ID NO 50
<211> LENGTH: 11
<212> TYPE: PRT
<213> ORGANISM: Mus musculus
<220> FEATURE:
<221> NAME/KEY: misc_feature
<223> OTHER INFORMATION: Ab 4518 HCDR3

<400> SEQUENCE: 50

Cys Ala Gly Gly Pro Ala Tyr Phe Asp Tyr Trp
1               5                   10

<210> SEQ ID NO 51
<211> LENGTH: 8
<212> TYPE: PRT
<213> ORGANISM: Mus musculus
<220> FEATURE:
<221> NAME/KEY: misc_feature
<223> OTHER INFORMATION: Ab 4380/4381 HCDR1

<400> SEQUENCE: 51

Gly Tyr Thr Phe Thr Asn Tyr Trp
1               5

<210> SEQ ID NO 52
<211> LENGTH: 8
<212> TYPE: PRT
<213> ORGANISM: Mus musculus
<220> FEATURE:
<221> NAME/KEY: misc_feature
<223> OTHER INFORMATION: Ab 4380/4381 HCDR2

<400> SEQUENCE: 52

Ile His Pro Ser Asp Ser Asp Val
1               5

<210> SEQ ID NO 53
<211> LENGTH: 13
<212> TYPE: PRT
<213> ORGANISM: Mus musculus
<220> FEATURE:
<221> NAME/KEY: misc_feature
<223> OTHER INFORMATION: Ab 4380/4381 HCDR3

<400> SEQUENCE: 53

Cys Ala Lys Ser Tyr Tyr Asp Ser Ala Met Asp Tyr Trp
1               5                   10
```

```
<210> SEQ ID NO 54
<211> LENGTH: 8
<212> TYPE: PRT
<213> ORGANISM: Mus musculus
<220> FEATURE:
<221> NAME/KEY: misc_feature
<223> OTHER INFORMATION: Ab 4382 HCDR1

<400> SEQUENCE: 54

Gly Tyr Thr Phe Thr Asp Tyr Tyr
1               5

<210> SEQ ID NO 55
<211> LENGTH: 8
<212> TYPE: PRT
<213> ORGANISM: Mus musculus
<220> FEATURE:
<221> NAME/KEY: misc_feature
<223> OTHER INFORMATION: Ab 4382 HCDR2

<400> SEQUENCE: 55

Ile Asn Pro Asn Asn Gly Gly Thr
1               5

<210> SEQ ID NO 56
<211> LENGTH: 13
<212> TYPE: PRT
<213> ORGANISM: Mus musculus
<220> FEATURE:
<221> NAME/KEY: misc_feature
<223> OTHER INFORMATION: Ab 4382 HCDR3

<400> SEQUENCE: 56

Cys Val Pro Gly Gly Leu Arg Ser Tyr Phe Asp Tyr Trp
1               5                   10

<210> SEQ ID NO 57
<211> LENGTH: 8
<212> TYPE: PRT
<213> ORGANISM: Mus musculus
<220> FEATURE:
<221> NAME/KEY: misc_feature
<223> OTHER INFORMATION: Ab 4383 HCDR1

<400> SEQUENCE: 57

Gly Tyr Thr Phe Thr Asp Tyr Ser
1               5

<210> SEQ ID NO 58
<211> LENGTH: 8
<212> TYPE: PRT
<213> ORGANISM: Mus musculus
<220> FEATURE:
<221> NAME/KEY: misc_feature
<223> OTHER INFORMATION: Ab 4383 HCDR2

<400> SEQUENCE: 58

Ile Asn Thr Ala Thr Gly Glu Pro
1               5

<210> SEQ ID NO 59
<211> LENGTH: 13
<212> TYPE: PRT
<213> ORGANISM: Mus musculus
<220> FEATURE:
<221> NAME/KEY: misc_feature
<223> OTHER INFORMATION: Ab 4383 HCDR3

<400> SEQUENCE: 59
```

```
Cys Thr Ala Trp Ala Tyr Glu Pro Tyr Phe Asp Tyr Trp
1               5                   10
```

<210> SEQ ID NO 60
<211> LENGTH: 8
<212> TYPE: PRT
<213> ORGANISM: Mus musculus
<220> FEATURE:
<221> NAME/KEY: misc_feature
<223> OTHER INFORMATION: Ab 4384 HCDR1

<400> SEQUENCE: 60

```
Gly Tyr Thr Phe Thr Ser His Trp
1               5
```

<210> SEQ ID NO 61
<211> LENGTH: 8
<212> TYPE: PRT
<213> ORGANISM: Mus musculus
<220> FEATURE:
<221> NAME/KEY: misc_feature
<223> OTHER INFORMATION: Ab 4384 HCDR2

<400> SEQUENCE: 61

```
Ile Asn Pro Ser Asn Gly Gly Thr
1               5
```

<210> SEQ ID NO 62
<211> LENGTH: 14
<212> TYPE: PRT
<213> ORGANISM: Mus musculus
<220> FEATURE:
<221> NAME/KEY: misc_feature
<223> OTHER INFORMATION: Ab 4384 HCDR3

<400> SEQUENCE: 62

```
Cys Ala Arg Ala Tyr Tyr Asp Phe Ser Trp Phe Val Tyr Trp
1               5                   10
```

<210> SEQ ID NO 63
<211> LENGTH: 8
<212> TYPE: PRT
<213> ORGANISM: Mus musculus
<220> FEATURE:
<221> NAME/KEY: misc_feature
<223> OTHER INFORMATION: Ab 4385 HCDR1

<400> SEQUENCE: 63

```
Gly Tyr Thr Phe Thr Gly Tyr Trp
1               5
```

<210> SEQ ID NO 64
<211> LENGTH: 8
<212> TYPE: PRT
<213> ORGANISM: Mus musculus
<220> FEATURE:
<221> NAME/KEY: misc_feature
<223> OTHER INFORMATION: Ab 4385 HCDR2

<400> SEQUENCE: 64

```
Ile Leu Pro Gly Ser Gly Ser Thr
1               5
```

<210> SEQ ID NO 65
<211> LENGTH: 12
<212> TYPE: PRT
<213> ORGANISM: Mus musculus
<220> FEATURE:

<221> NAME/KEY: misc_feature
<223> OTHER INFORMATION: Ab 4385 HCDR3

<400> SEQUENCE: 65

Cys Ala Arg Trp Gly Asp Gly Ser Phe Ala Tyr Trp
1               5                   10

<210> SEQ ID NO 66
<211> LENGTH: 8
<212> TYPE: PRT
<213> ORGANISM: Mus musculus
<220> FEATURE:
<221> NAME/KEY: misc_feature
<223> OTHER INFORMATION: Ab 4386 HCDR1

<400> SEQUENCE: 66

Gly Tyr Thr Phe Thr Ser Tyr Trp
1               5

<210> SEQ ID NO 67
<211> LENGTH: 8
<212> TYPE: PRT
<213> ORGANISM: Mus musculus
<220> FEATURE:
<221> NAME/KEY: misc_feature
<223> OTHER INFORMATION: Ab 4386 HCDR2

<400> SEQUENCE: 67

Ile His Pro Asn Ser Gly Ser Ile
1               5

<210> SEQ ID NO 68
<211> LENGTH: 12
<212> TYPE: PRT
<213> ORGANISM: Mus musculus
<220> FEATURE:
<221> NAME/KEY: misc_feature
<223> OTHER INFORMATION: Ab 4386 HCDR3

<400> SEQUENCE: 68

Cys Ala Gly Tyr Gly Asn Gly Pro Met Asp Tyr Trp
1               5                   10

<210> SEQ ID NO 69
<211> LENGTH: 8
<212> TYPE: PRT
<213> ORGANISM: Mus musculus
<220> FEATURE:
<221> NAME/KEY: misc_feature
<223> OTHER INFORMATION: Ab 4387 HCDR1

<400> SEQUENCE: 69

Gly Tyr Thr Phe Thr Asn Tyr Trp
1               5

<210> SEQ ID NO 70
<211> LENGTH: 8
<212> TYPE: PRT
<213> ORGANISM: Mus musculus
<220> FEATURE:
<221> NAME/KEY: misc_feature
<223> OTHER INFORMATION: Ab 4387 HCDR2

<400> SEQUENCE: 70

Ile Leu Pro Gly Gly Gly Tyr Thr
1               5

<210> SEQ ID NO 71

```
<211> LENGTH: 15
<212> TYPE: PRT
<213> ORGANISM: Mus musculus
<220> FEATURE:
<221> NAME/KEY: misc_feature
<223> OTHER INFORMATION: Ab 4387 HCDR3

<400> SEQUENCE: 71

Cys Ala Arg Gly Ser Ser Gly Tyr Pro Tyr Tyr Phe Asp Tyr Trp
1               5                   10                  15

<210> SEQ ID NO 72
<211> LENGTH: 8
<212> TYPE: PRT
<213> ORGANISM: Mus musculus
<220> FEATURE:
<221> NAME/KEY: misc_feature
<223> OTHER INFORMATION: Ab 4519 HCDR1

<400> SEQUENCE: 72

Gly Tyr Ser Phe Thr Asp Tyr Asn
1               5

<210> SEQ ID NO 73
<211> LENGTH: 8
<212> TYPE: PRT
<213> ORGANISM: Mus musculus
<220> FEATURE:
<221> NAME/KEY: misc_feature
<223> OTHER INFORMATION: Ab 4519 HCDR2

<400> SEQUENCE: 73

Ile Asp Pro Tyr Asn Gly Gly Thr
1               5

<210> SEQ ID NO 74
<211> LENGTH: 12
<212> TYPE: PRT
<213> ORGANISM: Mus musculus
<220> FEATURE:
<221> NAME/KEY: misc_feature
<223> OTHER INFORMATION: Ab 4519 HCDR3

<400> SEQUENCE: 74

Cys Ala Arg Gly Ala Gly Tyr Ala Leu Asp Tyr Trp
1               5                   10

<210> SEQ ID NO 75
<211> LENGTH: 6
<212> TYPE: PRT
<213> ORGANISM: Mus musculus
<220> FEATURE:
<221> NAME/KEY: misc_feature
<223> OTHER INFORMATION: Ab 4517 LCDR1

<400> SEQUENCE: 75

Glu Asn Ile Tyr Ser Asn
1               5

<210> SEQ ID NO 76
<211> LENGTH: 11
<212> TYPE: PRT
<213> ORGANISM: Mus musculus
<220> FEATURE:
<221> NAME/KEY: misc_feature
<223> OTHER INFORMATION: Ab 4517 LCDR3

<400> SEQUENCE: 76

Cys Gln His Phe Trp Gly Thr Pro Trp Thr Phe
```

<210> SEQ ID NO 77
<211> LENGTH: 6
<212> TYPE: PRT
<213> ORGANISM: Mus musculus
<220> FEATURE:
<221> NAME/KEY: misc_feature
<223> OTHER INFORMATION: Ab 4518 LCDR1

<400> SEQUENCE: 77

Gln Asp Val Ile Ala Ala
1               5

<210> SEQ ID NO 78
<211> LENGTH: 11
<212> TYPE: PRT
<213> ORGANISM: Mus musculus
<220> FEATURE:
<221> NAME/KEY: misc_feature
<223> OTHER INFORMATION: Ab 4518 LCDR3

<400> SEQUENCE: 78

Cys Gln Gln His Tyr Ser Thr Pro Trp Thr Phe
1               5                   10

<210> SEQ ID NO 79
<211> LENGTH: 10
<212> TYPE: PRT
<213> ORGANISM: Mus musculus
<220> FEATURE:
<221> NAME/KEY: misc_feature
<223> OTHER INFORMATION: Ab 4380/4381 LCDR1

<400> SEQUENCE: 79

Lys Ser Val Thr Thr Ser Gly Tyr Ser Tyr
1               5                   10

<210> SEQ ID NO 80
<211> LENGTH: 11
<212> TYPE: PRT
<213> ORGANISM: Mus musculus
<220> FEATURE:
<221> NAME/KEY: misc_feature
<223> OTHER INFORMATION: Ab 4380/4381 LCDR3

<400> SEQUENCE: 80

Cys His His Ser Arg Glu Leu Pro Trp Thr Phe
1               5                   10

<210> SEQ ID NO 81
<211> LENGTH: 6
<212> TYPE: PRT
<213> ORGANISM: Mus musculus
<220> FEATURE:
<221> NAME/KEY: misc_feature
<223> OTHER INFORMATION: Ab 4382 LCDR1

<400> SEQUENCE: 81

Gln Asp Val Ser Ala Ala
1               5

<210> SEQ ID NO 82
<211> LENGTH: 11
<212> TYPE: PRT
<213> ORGANISM: Mus musculus
<220> FEATURE:
<221> NAME/KEY: misc_feature
<223> OTHER INFORMATION: Ab 4382 LCDR3

<400> SEQUENCE: 82

Cys Gln Gln His Tyr Thr Thr Pro Pro Thr Phe
1               5                   10

<210> SEQ ID NO 83
<211> LENGTH: 6
<212> TYPE: PRT
<213> ORGANISM: Mus musculus
<220> FEATURE:
<221> NAME/KEY: misc_feature
<223> OTHER INFORMATION: Ab 4383 LCDR1

<400> SEQUENCE: 83

Gln Asp Val Phe Thr Ala
1               5

<210> SEQ ID NO 84
<211> LENGTH: 11
<212> TYPE: PRT
<213> ORGANISM: Mus musculus
<220> FEATURE:
<221> NAME/KEY: misc_feature
<223> OTHER INFORMATION: Ab 4383 LCDR3

<400> SEQUENCE: 84

Cys Gln Gln His Phe Gly Ile Pro Trp Thr Phe
1               5                   10

<210> SEQ ID NO 85
<211> LENGTH: 6
<212> TYPE: PRT
<213> ORGANISM: Mus musculus
<220> FEATURE:
<221> NAME/KEY: misc_feature
<223> OTHER INFORMATION: Ab 4384 LCDR1

<400> SEQUENCE: 85

Gln Asp Ile Ser Asn Tyr
1               5

<210> SEQ ID NO 86
<211> LENGTH: 11
<212> TYPE: PRT
<213> ORGANISM: Mus musculus
<220> FEATURE:
<221> NAME/KEY: misc_feature
<223> OTHER INFORMATION: Ab 4384 LCDR3

<400> SEQUENCE: 86

Cys Gln Gln Gly Asn Thr Leu Pro Leu Thr Phe
1               5                   10

<210> SEQ ID NO 87
<211> LENGTH: 6
<212> TYPE: PRT
<213> ORGANISM: Mus musculus
<220> FEATURE:
<221> NAME/KEY: misc_feature
<223> OTHER INFORMATION: Ab 4385 LCDR1

<400> SEQUENCE: 87

Gln Asn Val Gly Thr Ala
1               5

<210> SEQ ID NO 88
<211> LENGTH: 11
<212> TYPE: PRT

```
<213> ORGANISM: Mus musculus
<220> FEATURE:
<221> NAME/KEY: misc_feature
<223> OTHER INFORMATION: Ab 4385 LCDR3

<400> SEQUENCE: 88

Cys Gln Gln Tyr Arg Ser Tyr Pro Phe Thr Phe
1               5                   10

<210> SEQ ID NO 89
<211> LENGTH: 5
<212> TYPE: PRT
<213> ORGANISM: Mus musculus
<220> FEATURE:
<221> NAME/KEY: misc_feature
<223> OTHER INFORMATION: Ab 4386 + Ab 4519 LCDR1

<400> SEQUENCE: 89

Ser Ser Val Ser Tyr
1               5

<210> SEQ ID NO 90
<211> LENGTH: 11
<212> TYPE: PRT
<213> ORGANISM: Mus musculus
<220> FEATURE:
<221> NAME/KEY: misc_feature
<223> OTHER INFORMATION: Ab 4386 LCDR3

<400> SEQUENCE: 90

Cys Gln Gln Tyr His Asn Tyr Pro Leu Thr Phe
1               5                   10

<210> SEQ ID NO 91
<211> LENGTH: 6
<212> TYPE: PRT
<213> ORGANISM: Mus musculus
<220> FEATURE:
<221> NAME/KEY: misc_feature
<223> OTHER INFORMATION: Ab 4387 LCDR1

<400> SEQUENCE: 91

Gln Asp Val Gly Thr Ala
1               5

<210> SEQ ID NO 92
<211> LENGTH: 13
<212> TYPE: PRT
<213> ORGANISM: Mus musculus
<220> FEATURE:
<221> NAME/KEY: misc_feature
<223> OTHER INFORMATION: Ab 4387 LCDR3

<400> SEQUENCE: 92

Cys Gln Gln Tyr Ser Ser Tyr Pro Tyr Met Tyr Thr Phe
1               5                   10

<210> SEQ ID NO 93
<211> LENGTH: 11
<212> TYPE: PRT
<213> ORGANISM: Mus musculus
<220> FEATURE:
<221> NAME/KEY: misc_feature
<223> OTHER INFORMATION: Ab 4519 LCDR3

<400> SEQUENCE: 93

Cys Gln Gln Trp Ser Ser Thr Pro Tyr Thr Phe
1               5                   10
```

```
<210> SEQ ID NO 94
<211> LENGTH: 20
<212> TYPE: DNA
<213> ORGANISM: Artificial Sequence
<220> FEATURE:
<223> OTHER INFORMATION: Primer

<400> SEQUENCE: 94
gacsgatggg cccttggtgg                                              20

<210> SEQ ID NO 95
<211> LENGTH: 20
<212> TYPE: DNA
<213> ORGANISM: Artificial Sequence
<220> FEATURE:
<223> OTHER INFORMATION: Primer

<400> SEQUENCE: 95
gctgtaggtg ctgtctttgc                                              20

<210> SEQ ID NO 96
<211> LENGTH: 39
<212> TYPE: DNA
<213> ORGANISM: Artificial Sequence
<220> FEATURE:
<223> OTHER INFORMATION: Primer

<400> SEQUENCE: 96
tattcccatg gcgcgccsag gtccarctgc arcagyctg                         39

<210> SEQ ID NO 97
<211> LENGTH: 37
<212> TYPE: DNA
<213> ORGANISM: Artificial Sequence
<220> FEATURE:
<223> OTHER INFORMATION: Primer

<400> SEQUENCE: 97
tattcccatg gcgcgccgar gtgmagctkg tkgagtc                           37

<210> SEQ ID NO 98
<211> LENGTH: 37
<212> TYPE: DNA
<213> ORGANISM: Artificial Sequence
<220> FEATURE:
<223> OTHER INFORMATION: Primer

<400> SEQUENCE: 98
tattcccatg gcgcgccsag gtgcagctkm aggagtc                           37

<210> SEQ ID NO 99
<211> LENGTH: 37
<212> TYPE: DNA
<213> ORGANISM: Artificial Sequence
<220> FEATURE:
<223> OTHER INFORMATION: Primer

<400> SEQUENCE: 99
tattcccatg gcgcgcccag gttactctga aagagtc                           37

<210> SEQ ID NO 100
<211> LENGTH: 39
<212> TYPE: DNA
<213> ORGANISM: Artificial Sequence
<220> FEATURE:
<223> OTHER INFORMATION: Primer
```

-continued

<400> SEQUENCE: 100
tattcccatg gcgcgcccag atccagttgg tgcagtctg          39

<210> SEQ ID NO 101
<211> LENGTH: 45
<212> TYPE: DNA
<213> ORGANISM: Artificial Sequence
<220> FEATURE:
<223> OTHER INFORMATION: Primer

<400> SEQUENCE: 101
ggcgcgccat gggaatagct agccgayatc cagatgachc arwct      45

<210> SEQ ID NO 102
<211> LENGTH: 44
<212> TYPE: DNA
<213> ORGANISM: Artificial Sequence
<220> FEATURE:
<223> OTHER INFORMATION: Primer

<400> SEQUENCE: 102
ggcgcgccat gggaatagct agccracatt gtgmtgachc agtc       44

<210> SEQ ID NO 103
<211> LENGTH: 46
<212> TYPE: DNA
<213> ORGANISM: Artificial Sequence
<220> FEATURE:
<223> OTHER INFORMATION: Primer

<400> SEQUENCE: 103
ggcgcgccat gggaatagct agccsamatt gtkctsaccc artctc     46

<210> SEQ ID NO 104
<211> LENGTH: 45
<212> TYPE: DNA
<213> ORGANISM: Artificial Sequence
<220> FEATURE:
<223> OTHER INFORMATION: Primer

<400> SEQUENCE: 104
ggcgcgccat gggaatagct agccgatrtt gtgatgacbc arrct      45

<210> SEQ ID NO 105
<211> LENGTH: 24
<212> TYPE: DNA
<213> ORGANISM: Artificial Sequence
<220> FEATURE:
<223> OTHER INFORMATION: Primer

<400> SEQUENCE: 105
ggacagggmt ccakagttcc adkt                            24

<210> SEQ ID NO 106
<211> LENGTH: 43
<212> TYPE: DNA
<213> ORGANISM: Artificial Sequence
<220> FEATURE:
<223> OTHER INFORMATION: Primer

<400> SEQUENCE: 106
gacagatggt gcagccacag ttcgtttgat ttccagcttg gtg       43

<210> SEQ ID NO 107
<211> LENGTH: 43
<212> TYPE: DNA

-continued

<213> ORGANISM: Artificial Sequence
<220> FEATURE:
<223> OTHER INFORMATION: Primer

<400> SEQUENCE: 107
gacagatggt gcagccacag ttcgttttat ttccagcttg gtc     43

<210> SEQ ID NO 108
<211> LENGTH: 43
<212> TYPE: DNA
<213> ORGANISM: Artificial Sequence
<220> FEATURE:
<223> OTHER INFORMATION: Primer

<400> SEQUENCE: 108
gacagatggt gcagccacag ttcgttttat ttccaacttt gtc     43

<210> SEQ ID NO 109
<211> LENGTH: 43
<212> TYPE: DNA
<213> ORGANISM: Artificial Sequence
<220> FEATURE:
<223> OTHER INFORMATION: Primer

<400> SEQUENCE: 109
gacagatggt gcagccacag ttcgtttcag ctccagcttg gtc     43

<210> SEQ ID NO 110
<211> LENGTH: 23
<212> TYPE: DNA
<213> ORGANISM: Artificial Sequence
<220> FEATURE:
<223> OTHER INFORMATION: Primer

<400> SEQUENCE: 110
gaactgtggc tgcaccatct gtc     23

<210> SEQ ID NO 111
<211> LENGTH: 43
<212> TYPE: DNA
<213> ORGANISM: Artificial Sequence
<220> FEATURE:
<223> OTHER INFORMATION: Primer

<400> SEQUENCE: 111
accgcctcca ccggcggccg cttattaaca ctctcccctg ttg     43

<210> SEQ ID NO 112
<211> LENGTH: 51
<212> TYPE: DNA
<213> ORGANISM: Artificial Sequence
<220> FEATURE:
<223> OTHER INFORMATION: Primer

<400> SEQUENCE: 112
accgcctcca ccggcggccg cttattaaca ctctcccctg ttgaagctct t     51

<210> SEQ ID NO 113
<211> LENGTH: 30
<212> TYPE: DNA
<213> ORGANISM: Artificial Sequence
<220> FEATURE:
<223> OTHER INFORMATION: Primer

<400> SEQUENCE: 113
ggaggcgctc gagacggtga ccgtggtccc     30

```
<210> SEQ ID NO 114
<211> LENGTH: 30
<212> TYPE: DNA
<213> ORGANISM: Artificial Sequence
<220> FEATURE:
<223> OTHER INFORMATION: Primer

<400> SEQUENCE: 114
ggaggcgctc gagactgtga gagtggtgcc                                          30

<210> SEQ ID NO 115
<211> LENGTH: 30
<212> TYPE: DNA
<213> ORGANISM: Artificial Sequence
<220> FEATURE:
<223> OTHER INFORMATION: Primer

<400> SEQUENCE: 115
ggaggcgctc gagacagtga ccagagtccc                                          30

<210> SEQ ID NO 116
<211> LENGTH: 30
<212> TYPE: DNA
<213> ORGANISM: Artificial Sequence
<220> FEATURE:
<223> OTHER INFORMATION: Primer

<400> SEQUENCE: 116
ggaggcgctc gagacggtga ctgaggttcc                                          30
```